(12) United States Patent
Ni et al.

(10) Patent No.: US 6,509,173 B1
(45) Date of Patent: Jan. 21, 2003

(54) HUMAN TUMOR NECROSIS FACTOR RECEPTOR-LIKE PROTEINS TR11, TR11SV1, AND TR11SV2

(75) Inventors: Jian Ni, Rockville, MD (US); Steven M. Ruben, Olney, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/176,200

(22) Filed: Oct. 21, 1998

Related U.S. Application Data

(60) Provisional application No. 60/063,212, filed on Oct. 21, 1997.

(51) Int. Cl.[7] .......................... C12P 21/06; C12N 15/00; C12N 15/09; C12N 15/63; C12N 15/70

(52) U.S. Cl. .................. 435/69.1; 435/320.1; 435/325; 435/395; 530/300; 530/350; 530/395; 436/1.11; 436/18.7; 436/22.1; 436/23.1; 436/23.5

(58) Field of Search ................................ 536/23.5, 1.11, 536/18.7, 22.1, 23.1; 435/69.1, 320.1, 325; 530/395, 300, 350

(56) References Cited

U.S. PATENT DOCUMENTS 5,116,964 A * 5/1992 Capon et al.
6,111,090 A * 8/2000 Gorman et al.

FOREIGN PATENT DOCUMENTS

| WO | WO96/09386 | 3/1996 |
| WO | 98/06842 | 2/1998 |
| WO | 99/20758 | 4/1999 |

OTHER PUBLICATIONS

Lazar et al. Transforming Growth Factor Alpha: Mutation of Aspartic Acid 47 and Leucine 48 Results in Different Biological Activities, Molecular and Cellular Biology 8(3):1247–1252, Mar. 1988.*

Beutler et al, Science, 264: 667–668, 1994.*

International Search Report, mailed Jul. 31, 2000, in copending international application No. PCT/US00/04572.

Nocentini, et al.—A new member of the tumor necrosis factor/nerve growth factor receptor family inhibits T cell receptor–induced apoptosis, *Proc. Natl. Acad. Sci. USA*, vol. 94, pp. 6216–6221, Jun. 1997 Cell Biology.

Gurney, et al.—Identification of a new member of the tumor necrosis factor family and its receptor, a human ortholog of mouse GITR, *Current Biology*, 1999, 9:215–218.

Baens et al., *Genomics* 16:214–218 (1993).

Gurney et al., *Curr. Biol.*, "Identification of a new member of the tumor necrosis factor family and its receptor, a human ortholog of mouse GITR" (In press)(abstract only)—Genbank Accession No. AF125304.

Kwon et al., *J. Biol. Chem.* 274:6056–6061 (1999).

* cited by examiner

*Primary Examiner*—Anthony C. Caputa
*Assistant Examiner*—Alana M. Harris
(74) *Attorney, Agent, or Firm*—Human Genome Sciences, Inc.

(57) ABSTRACT

The present invention relates to novel members of the Tumor Necrosis Factor family of receptors. The invention provides isolated nucleic acid molecules encoding human TR11, TR11SV1, and TR11SV2 receptors. TR11, TR11SV1, and TR11SV2 polypeptides are also provided, as are vectors, host cells and recombinant methods for producing the same. The invention further relates to screening methods for identifying agonists and antagonists of TR11, TR11SV1, and TR11SV2 receptor activity. Also provided are diagnostic methods for detecting disease states related to the aberrant expression of TR11, TR11SV1, and TR11SV2 receptors. Further provided are therapeutic methods for treating disease states related to aberrant proliferation and differentiation of cells which express the TR11, TR11SV1, and TR11SV2 receptors.

41 Claims, 11 Drawing Sheets

Figure 1A

```
  1  GCACTTCACCTGGGTCGGGATTCTCAGGTCATGAACGGTCCCAGCCACCT   50

51  CCGGGCAGGGCGGGTGAGGACGGGGACGGGGCGTGTCCAACTGGCTGTGG  100

101  GCTCTTGAAACCCGAGCATGGCACAGCACGGGGCGATGGGCGCGTTTCGG  150
  1               M  A  Q  H  G  A  M  G  A  F  R        11

151  GCCCTGTGCGGCCTGGCGCTGCTGTGCGCGCTCAGCCTGGGTCAGCGCCC  200
 12    A  L  C  G  L  A  L  L  C  A  L  S  L  G  Q  R    27

201  CACCGGGGGTCCCGGGTGCGGCCCTGGGCGCCTCCTGCTTGGGACGGGAA  250
 28   P  T  G  G  P  G  C  G  P  G  R  L  L  L  G  T  G  44

251  CGGACGCGCGCTGCTGCCGGGTTCACACGACGCGCTGCTGCCGCGATTAC  300
 45    T  D  A  R  C  C  R  V  H  T  T  R  C  C  R  D  Y 61

301  CCGGGCGAGGAGTGCTGTTCCGAGTGGGACTGCATGTGTGTCCAGCCTGA  350
 62     P  G  E  E  C  C  S  E  W  D  C  M  C  V  Q  P    77
                                          CD-II

351  ATTCCACTGCGGAGACCCTTGCTGCACGACCTGCCGGCACCACCCTTGTC  400
 78   E  F  H  C  G  D  P  C  C  T  T  C  R  H  H  P  C   94
        CD-II                    CD-III

401  CCCCAGGCCAGGGGGTACAGTCCCAGGGGAAATTCAGTTTTGGCTTCCAG  450
 95    P  P  G  Q  G  V  Q  S  Q  G  K  F  S  F  G  F  Q 111
                                              CD-IV

451  TGTATCGACTGTGCCTCGGGGACCTTCTCCGGGGGCCACGAAGGCCACTG  500
112    C  I  D  C  A  S  G  T  F  S  G  G  H  E  G  H    127
        CD-IV

501  CAAACCTTGGACAGACTGCACCCAGTTCGGGTTTCTCACTGTGTTCCCTG  550
128   C  K  P  W  T  D  C  T  Q  F  G  F  L  T  V  F  P  144
        CD-V
```

Figure 1B

```
       #
551  GGAACAAGACCCACAACGCTGTGTGCGTCCCAGGGTCCCCGCCGGCAGAG  600
145    G  N  K  T  H  N  A  V  C  V  P  G  S  P  P  A  E  161
                                  CD-VI

601  CCGCTTGGGTGGCTGACCGTCGTCCTCCTGGCCGTGGCCGCCTGCGTCCT  650
162    P  L  G  W  L  T  V  V  L  L  A  V  A  A  C  V    177
                                                  CD-VII

651  CCTCCTGACCTCGGCCCAGCTTGGACTGCACATCTGGCAGCTGAGGAAGA  700
178    L  L  L  T  S  A  Q  L  G  L  H  I  W  Q  L  R  K  194
              CD-VII

701  CCCAGCTGCTGCTGGAGGTGCCGCCGTCGACCGAAGACGCCAGAAGCTGC  750
195    T  Q  L  L  L  E  V  P  P  S  T  E  D  A  R  S  C  211
                                      CD-IX

751  CAGTTCCCCGAGGAAGAGCGGGGCGAGCGATCGGCAGAGGAGAAGGGGCG  800
212    Q  F  P  E  E  E  R  G  E  R  S  A  E  E  K  G     227
                                              CD-X

801  GCTGGGAGACCTGTGGGTGTGAGCCTGGCCGTCCTCCGGGGCCACCGACC  850
228    R  L  G  D  L  W  V                                234
           CD-X

851  GCAGCCAGCCCCTCCCCAGGAGCTCCCCAGGCCGCAGGGGCTCTGCGTTC  900

901  TGCTCTGGGCCGGGCCCTGCTCCCCTGGCAGCAGAAGTGGGTGCAGGAAG  950

951  GTGGCAGTGACCAGCGCCCTGGACCATGCAGTT  983
```

Figure 2A

```
  1 GTCGACCCACGCGTCCGGGGGGCCACCCCTGGGTCCTGCAGGGGCAGCTC   50

51 CTGGTTGCATATGGAGTTAGCACCTGGGCAGGGGCAGCTGTGGGCGCAA   100

101 AGGGGGAGTAGCCAGGCCACATGGCCCCAGGAGAAAGAGACAGCTGGATA   150
  1                         M  A  P  G  E  R  D  S  W  I    10

151 AACCCAGGTCCAGACTCCCAGCCAGGAGCCCTCTGCTCCCTGGAGCCAAC   200
 11  N  P  G  P  D  S  Q  P  G  A  L  C  S  L  E  P      26

201 TGTGGGTGGAGAACGGACAACCTCACTCCCCTGGAGGGCCGAGGGGAGGC   250
 27  T  V  G  G  E  R  T  T  S  L  P  W  R  A  E  G  R   43

251 CTGGGGAGGAGGGGGCCTCAGCCCAGCTGCTGGGGGGCTGGCCTGTCTCC   300
 44  P  G  E  E  G  A  S  A  Q  L  L  G  G  W  P  V  S   60
                              ─────────────────────────
                                        CD-I

301 TGCCCAGGCGAGGAGTGCTGTTCCGAGTGGGACTGCATGTGTGTCCAGCC   350
 61  C  P  G  E  E  C  C  S  E  W  D  C  M  C  V  Q     76
     ─                            ─────────────
     CD-I                              CD-II

351 TGAATTCCACTGCGGAGACCCTTGCTGCACGACCTGCCGGCACCACCCTT   400
 77  P  E  F  H  C  G  D  P  C  C  T  T  C  R  H  H  P   93
     ──────────────         ───────────────────────────
         CD-II                        CD-III

401 GTCCCCCAGGCCAGGGGGTACAGTCCCAGGGGAAATTCAGTTTTGGCTTC   450
 94  C  P  P  G  Q  G  V  Q  S  Q  G  K  F  S  F  G  F  110
     ─                                         ─────────
     CD-III                                       CD-IV

451 CAGTGTATCGACTGTGCCTCGGGGACCTTCTCCGGGGCCACGAAGGCCA    500
111  Q  C  I  D  C  A  S  G  T  F  S  G  G  H  E  G     126
     ──────────────
         CD-IV

501 CTGCAAACCTTGGACAGACTGCACCCAGTTCGGGTTTCTCACTGTGTTCC   550
127  H  C  K  P  W  T  D  C  T  Q  F  G  F  L  T  V  F  143
        ──────────────
            CD-V
```

Figure 2B

```
         #    .              .              .              .              .
551 CTGGGAACAAGACCCACAACGCTGTGTGCGTCCCAGGGTCCCCGCCGGCA    600
144 P  G  N  K  T  H  N  A  V  C  V  P  G  S  P  P  A    160
                                  ─────────────────────
                                         CD-VI

.              .              .              .              .
601 GAGCCGCTTGGGTGGCTGACCGTCGTCCTCCTGGCCGTGGCCGCCTGCGT    650
161 E  P  L  G  W  L  T  V  V  L  L  A  V  A  A  C  V    177
                                                 ──────
                                                 CD-VII

.              .              .              .              .
651 CCTCCTCCTGACCTCGGCCCAGCTTGGACTGCACATCTGGCAGCTGAGGA    700
178 L  L  L  T  S  A  Q  L  G  L  H  I  W  Q  L  R       193
    ───────────────────────
           CD-VII

.              .              .              .              .
701 GTCAGTGCATGTGGCCCCGAGAGACCCAGCTGCTGCTGGAGGTGCCGCCG    750
194 S  Q  C  M  W  P  R  E  T  Q  L  L  L  E  V  P  P    210
       ────────────────────
            CD-VIII

.              .              .              .              .
751 TCGACCGAAGACGCCAGAAGCTGCCAGTTCCCCGAGGAAGAGCGGGGCGA    800
211 S  T  E  D  A  R  S  C  Q  F  P  E  E  E  R  G  E    227
    ────────────────
        CD-IX

.              .              .              .              .
801 GCGATCGGCAGAGGAGAAGGGGCGGCTGGGAGACCTGTGGGTGTGAGCCT    850
228 R  S  A  E  E  K  G  R  L  G  D  L  W  V             241
             ──────────────────────────────
                         CD-X

.              .              .              .              .
851 GGCCGTCCTCCGGGGCCACCGACCGCAGCCAGCCCCTCCCCAGGAGCTCC    900

.              .              .              .              .
901 CCAGGCCGCAGGGGCTCTGCGTTCTGCTCTGGGCCGGGCCCTGCTCCCCT    950

.              .              .              .              .
951 GGCAGCAGAAGTGGGTGCAGGAAGGTGGCAGTGACCAGCGCCCTGGACCA    1000

1001 TGCAGTT    1007
```

Figure 3A

```
  1 ATGGGCGCGTTTCGGGCCCTGTGCGGCCTGGCGCTGCTGTGCGCGCTCAG    50
  1   M  G  A  F  R  A  L  C  G  L  A  L  L  C  A  L      16

51 CCTGGGTCAGCGCCCCACCGGGGGTCCCGGGTGCGGCCCTGGGCGCCTCC   100
 17  S  L  G  Q  R  P  T  G  G  P  G  C  G  P  G  R  L    33

101 TGCTTGGGACGGGAACGGACGCGCGCTGCTGCCGGGTTCACACGACGCGC   150
 34  L  L  G  T  G  T  D  A  R  C  C  R  V  H  T  T  R    50

151 TGCTGCCGCGATTACCCGGCCCAGCTGCTGGGGGGCTGGCCTGTCTCCTG   200
 51   C  C  R  D  Y  P  A  Q  L  L  G  G  W  P  V  S      66
                         CD-I

201 CCCAGGCGAGGAGTGCTGTTCCGAGTGGGACTGCATGTGTGTCCAGCCTG   250
 67  C  P  G  E  E  C  C  S  E  W  D  C  M  C  V  Q  P    83
    CD-I                               CD-II

251 AATTCCACTGCGGAGACCCTTGCTGCACGACCTGCCGGCACCACCCTTGT   300
 84  E  F  H  C  G  D  P  C  C  T  T  C  R  H  H  P  C   100
        CD-II                CD-III

301 CCCCCAGGCCAGGGGGTACAGTCCCAGGGGAAATTCAGTTTTGGCTTCCA   350
101    P  P  G  Q  G  V  Q  S  Q  G  K  F  S  F  G  F    116
                                           CD-IV

351 GTGTATCGACTGTGCCTCGGGGACCTTCTCCGGGGGCCACGAAGGCCACT   400
117  Q  C  I  D  C  A  S  G  T  F  S  G  G  H  E  G  H   133
       CD-IV

401 GCAAACCTTGGACAGACTGCACCCAGTTCGGGTTTCTCACTGTGTTCCCT   450
134   C  K  P  W  T  D  C  T  Q  F  G  F  L  T  V  F  P   150
          CD-V

451 GGGAACAAGACCCACAACGCTGTGTGCGTCCCAGGGTCCCCGCCGGCAGA   500
151   G  N  K  T  H  N  A  V  C  V  P  G  S  P  P  A    166
                                  CD-VI
```

Figure 3B

```
 501 GCCGCTTGGGTGGCTGACCGTCGTCCTCCTGGCCGTGGCCGCCTGCGTCC  550
 167  E  P  L  G  W  L  T  V  V  L  L  A  V  A  A  C  V   183
                                                  CD-VII

551 TCCTCCTGACCTCGGCCCAGCTTGGACTGCACATCTGGCAGCTGAGGAAG  600
 184  L  L  L  T  S  A  Q  L  G  L  H  I  W  Q  L  R  K   200
           CD-VII

601 ACCCAGCTGCTGCTGGAGGTGCCGCCGTCGACCGAAGACGCCAGAAGCTG  650
 201  T  Q  L  L  L  E  V  P  P  S  T  E  D  A  R  S      216
                                    CD-IX

651 CCAGTTCCCCGAGGAAGAGCGGGGCGAGCGATCGGCAGAGGAGAAGGGGC  700
 217  C  Q  F  P  E  E  E  R  G  E  R  S  A  E  E  K  G   233
                                            CD-X

701 GGCTGGGAGACCTGTGGGTGTGAGCCTGGCCGTCCTCCGGGGCCACCGAC  750
 234  R  L  G  D  L  W  V                                 240
         CD-X

751 CGCAGCCAGCCCCTCCCCAGGAGCTCCCCAGGCCGCAGGGGCTCTGCGTT  800

801 CTGCTCTGGGCCGGGCCCTGCTCCCCTGGCAGCAGAAGTGGGTGCAGGAA  850

851 GGTGGCAGTGACCAGCGCCCTGGACCATGCAGTTCGGCGGCCGCGGCTGG  900

901 GCCCTGCAGGAGGGAGAGAGAGACACAGTCATGGCCCCCTTCCTCCCTTG  950

951 CTGGCCCTGATGGGGTGGGGTCTTAGGACGGGAGGCTGTGTCCGTGGGTG 1000

1001 TGCAGTGCCCAGCACGGGACCCGGCTGCAGGGGACCTTCAATAAACACTT 1050

1051 GTCCAGTAAAAAAAAAAAAAAAAAA 1074
```

Figure 4A

```
                                                                          mGITR.aa
                                                                          TR11.aa
                                                                          TR11sv1.aa
                                                                          TR11sv2.aa 10              20              30              40           50
  |       |        |       |        |       |        |       |        |
1 H I W Q L R R Q H M C P R E T Q P F A E V Q L S A E D A C S F Q F P E E E R G E Q T - E E K C H L G
1 H I W Q L R K - - - - - - - T Q L L L E V P P S T E D A R S C Q F P E E E R G E R S A E E K G R L G
1 H I W Q L R S Q C M W P R E T Q L L L E V P P S T E D A R S C Q F P E E E R G E R S A E E K G R L G
1 H I W Q L R K - - - - - - - T Q L L L E V P P S T E D A R S C Q F P E E E R G E R S A E E K G R L G mGITR.aa
                                                                          TR11.aa
                                                                          TR11sv1.aa
                                                                          TR11sv2.aa
50 G R W P
44 D L W V
51 D L W V
44 D L W V

Decoration 'Decoration #1': Shade (with black at 50% fill) residues that differ from TR11.aa.⌐
```

Figure 4B

SEQUENCE LISTING

```
<160> NUMBER OF SEQ ID NOS: 27

<210> SEQ ID NO 1
<211> LENGTH: 983
<212> TYPE: DNA
<213> ORGANISM: Homo sapiens
<220> FEATURE:
<221> NAME/KEY: CDS
<222> LOCATION: (118)..(819)
<220> FEATURE:
<221> NAME/KEY: mat_peptide
<222> LOCATION: (193)..(819)
<220> FEATURE:
<221> NAME/KEY: scRNA
<222> LOCATION: (118)..(192)

<400> SEQUENCE: 1
gcacttcacc tgggtcggga ttctcaggtc atgaacggtc ccagccacct ccgggcaggg        60
cgggtgagga cggggacggg gcgtgtccaa ctggctgtgg gctcttgaaa cccgagc          117 atg gca cag cac ggg gcg atg ggc gcg ttt cgg gcc ctg tgc ggc ctg        165
Met Ala Gln His Gly Ala Met Gly Ala Phe Arg Ala Leu Cys Gly Leu
-25                 -20                 -15                 -10 gcg ctg ctg tgc gcg ctc agc ctg ggt cag cgc ccc acc ggg ggt ccc        213
Ala Leu Leu Cys Ala Leu Ser Leu Gly Gln Arg Pro Thr Gly Gly Pro
```

```
            -5              -1  1               5
ggg tgc ggc cct ggg cgc ctc ctg ctt ggg acg gga acg gac gcg cgc      261
Gly Cys Gly Pro Gly Arg Leu Leu Leu Gly Thr Gly Thr Asp Ala Arg
            10              15              20 tgc tgc cgg gtt cac acg acg cgc tgc tgc cgc gat tac ccg ggc gag      309
Cys Cys Arg Val His Thr Thr Arg Cys Cys Arg Asp Tyr Pro Gly Glu
        25              30              35 gag tgc tgt tcc gag tgg gac tgc atg tgt gtc cag cct gaa ttc cac      357
Glu Cys Cys Ser Glu Trp Asp Cys Met Cys Val Gln Pro Glu Phe His
    40              45              50              55 tgc gga gac cct tgc tgc acg acc tgc cgg cac cac cct tgt ccc cca      405
Cys Gly Asp Pro Cys Cys Thr Thr Cys Arg His His Pro Cys Pro Pro
                60              65              70 ggc cag ggg gta cag tcc cag ggg aaa ttc agt ttt ggc ttc cag tgt      453
Gly Gln Gly Val Gln Ser Gln Gly Lys Phe Ser Phe Gly Phe Gln Cys
            75              80              85 atc gac tgt gcc tcg ggg acc ttc tcc ggg ggc cac gaa ggc cac tgc      501
Ile Asp Cys Ala Ser Gly Thr Phe Ser Gly Gly His Glu Gly His Cys
        90              95              100 aaa cct tgg aca gac tgc acc cag ttc ggg ttt ctc act gtg ttc cct      549
Lys Pro Trp Thr Asp Cys Thr Gln Phe Gly Phe Leu Thr Val Phe Pro
    105             110             115 ggg aac aag acc cac aac gct gtg tgc gtc cca ggg tcc ccg ccg gca      597
Gly Asn Lys Thr His Asn Ala Val Cys Val Pro Gly Ser Pro Pro Ala
120             125             130             135 gag ccg ctt ggg tgg ctg acc gtc gtc ctc ctg gcc gtg gcc gcc tgc      645
Glu Pro Leu Gly Trp Leu Thr Val Val Leu Leu Ala Val Ala Ala Cys
            140             145             150 gtc ctc ctc ctg acc tcg gcc cag ctt gga ctg cac atc tgg cag ctg      693
Val Leu Leu Leu Thr Ser Ala Gln Leu Gly Leu His Ile Trp Gln Leu
        155             160             165 agg aag acc cag ctg ctg ctg gag gtg ccg ccg tcg acc gaa gac gcc      741
Arg Lys Thr Gln Leu Leu Leu Glu Val Pro Pro Ser Thr Glu Asp Ala
    170             175             180 aga agc tgc cag ttc ccc gag gaa gag cgg ggc gag cga tcg gca gag      789
Arg Ser Cys Gln Phe Pro Glu Glu Glu Arg Gly Glu Arg Ser Ala Glu
185             190             195 gag aag ggg cgg ctg gga gac ctg tgg gtg tgagcctggc cgtcctccgg       839
Glu Lys Gly Arg Leu Gly Asp Leu Trp Val
200             205 ggccaccgac cgcagccagc ccctccccag gagctcccca ggccgcaggg gctctgcgtt   899
ctgctctggg ccgggccctg ctcccctggc agcagaagtg ggtgcaggaa ggtggcagtg   959
accagcgccc tggaccatgc agtt                                          983

<210> SEQ ID NO 2
<211> LENGTH: 234
<212> TYPE: PRT
<213> ORGANISM: Homo sapiens

<400> SEQUENCE: 2

Met Ala Gln His Gly Ala Met Gly Ala Phe Arg Ala Leu Cys Gly Leu
-25             -20             -15             -10

Ala Leu Leu Cys Ala Leu Ser Leu Gly Gln Arg Pro Thr Gly Gly Pro
            -5              -1  1               5

Gly Cys Gly Pro Gly Arg Leu Leu Leu Gly Thr Gly Thr Asp Ala Arg
        10              15              20

Cys Cys Arg Val His Thr Thr Arg Cys Cys Arg Asp Tyr Pro Gly Glu
    25              30              35
```

```
Glu Cys Cys Ser Glu Trp Asp Cys Met Cys Val Gln Pro Glu Phe His
 40                  45                  50                  55

Cys Gly Asp Pro Cys Cys Thr Thr Cys Arg His His Pro Cys Pro Pro
                 60                  65                  70

Gly Gln Gly Val Gln Ser Gln Gly Lys Phe Ser Phe Gly Phe Gln Cys
             75                  80                  85

Ile Asp Cys Ala Ser Gly Thr Phe Ser Gly Gly His Glu Gly His Cys
         90                  95                 100

Lys Pro Trp Thr Asp Cys Thr Gln Phe Gly Phe Leu Thr Val Phe Pro
    105                 110                 115

Gly Asn Lys Thr His Asn Ala Val Cys Val Pro Gly Ser Pro Pro Ala
120                 125                 130                 135

Glu Pro Leu Gly Trp Leu Thr Val Val Leu Ala Val Ala Ala Cys
                140                 145                 150

Val Leu Leu Leu Thr Ser Ala Gln Leu Gly Leu His Ile Trp Gln Leu
            155                 160                 165

Arg Lys Thr Gln Leu Leu Leu Glu Val Pro Pro Ser Thr Glu Asp Ala
            170                 175                 180

Arg Ser Cys Gln Phe Pro Glu Glu Arg Gly Glu Arg Ser Ala Glu
            185                 190                 195

Glu Lys Gly Arg Leu Gly Asp Leu Trp Val
200                 205

<210> SEQ ID NO 3
<211> LENGTH: 1007
<212> TYPE: DNA
<213> ORGANISM: Homo sapiens
<220> FEATURE:
<221> NAME/KEY: CDS
<222> LOCATION: (121)..(843)

<400> SEQUENCE: 3
gtcgacccac gcgtccgggg ggccacccct gggtcctgca ggggcagctc ctggttgcat     60
atggagttag cacctgggca ggggcagctg tggggcgcaa aggggagta gccaggccac    120 atg gcc cca gga gaa aga gac agc tgg ata aac cca ggt cca gac tcc     168
Met Ala Pro Gly Glu Arg Asp Ser Trp Ile Asn Pro Gly Pro Asp Ser
  1               5                  10                  15 cag cca gga gcc ctc tgc tcc ctg gag cca act gtg ggt gga gaa cgg     216
Gln Pro Gly Ala Leu Cys Ser Leu Glu Pro Thr Val Gly Gly Glu Arg
                 20                  25                  30 aca acc tca ctc ccc tgg agg gcc gag ggg agg cct ggg gag gag ggg     264
Thr Thr Ser Leu Pro Trp Arg Ala Glu Gly Arg Pro Gly Glu Glu Gly
             35                  40                  45 gcc tca gcc cag ctg ctg ggg ggc tgg cct gtc tcc tgc cca ggc gag     312
Ala Ser Ala Gln Leu Leu Gly Gly Trp Pro Val Ser Cys Pro Gly Glu
         50                  55                  60 gag tgc tgt tcc gag tgg gac tgc atg tgt gtc cag cct gaa ttc cac     360
Glu Cys Cys Ser Glu Trp Asp Cys Met Cys Val Gln Pro Glu Phe His
 65                  70                  75                  80 tgc gga gac cct tgc tgc acg acc tgc cgg cac cac cct tgt ccc cca     408
Cys Gly Asp Pro Cys Cys Thr Thr Cys Arg His His Pro Cys Pro Pro
                 85                  90                  95 ggc cag ggg gta cag tcc cag ggg aaa ttc agt ttt ggc ttc cag tgt     456
Gly Gln Gly Val Gln Ser Gln Gly Lys Phe Ser Phe Gly Phe Gln Cys
             100                 105                 110 atc gac tgt gcc tcg ggg acc ttc tcc ggg ggc cac gaa ggc cac tgc     504
Ile Asp Cys Ala Ser Gly Thr Phe Ser Gly Gly His Glu Gly His Cys
```

-continued

```
             115                 120                 125
aaa cct tgg aca gac tgc acc cag ttc ggg ttt ctc act gtg ttc cct      552
Lys Pro Trp Thr Asp Cys Thr Gln Phe Gly Phe Leu Thr Val Phe Pro
    130                 135                 140 ggg aac aag acc cac aac gct gtg tgc gtc cca ggg tcc ccg ccg gca      600
Gly Asn Lys Thr His Asn Ala Val Cys Val Pro Gly Ser Pro Pro Ala
145                 150                 155                 160 gag ccg ctt ggg tgg ctg acc gtc gtc ctg gcc gtg gcc gcc tgc          648
Glu Pro Leu Gly Trp Leu Thr Val Val Leu Ala Val Ala Ala Cys
                165                 170                 175 gtc ctc ctc ctg acc tcg gcc cag ctt gga ctg cac atc tgg cag ctg      696
Val Leu Leu Leu Thr Ser Ala Gln Leu Gly Leu His Ile Trp Gln Leu
            180                 185                 190 agg agt cag tgc atg tgg ccc cga gag acc cag ctg ctg ctg gag gtg      744
Arg Ser Gln Cys Met Trp Pro Arg Glu Thr Gln Leu Leu Leu Glu Val
        195                 200                 205 ccg ccg tcg acc gaa gac gcc aga agc tgc cag ttc ccc gag gaa gag      792
Pro Pro Ser Thr Glu Asp Ala Arg Ser Cys Gln Phe Pro Glu Glu Glu
    210                 215                 220 cgg ggc gag cga tcg gca gag gag aag ggg cgg ctg gga gac ctg tgg      840
Arg Gly Glu Arg Ser Ala Glu Glu Lys Gly Arg Leu Gly Asp Leu Trp
225                 230                 235                 240 gtg tgagcctggc cgtcctccgg ggccaccgac cgcagccagc ccctccccag           893
Val gagctcccca ggccgcaggg gctctgcgtt ctgctctggg ccgggccctg ctccctggc     953 agcagaagtg ggtgcaggaa ggtggcagtg accagcgccc tggaccatgc agtt         1007
```

<210> SEQ ID NO 4
<211> LENGTH: 241
<212> TYPE: PRT
<213> ORGANISM: Homo sapiens

<400> SEQUENCE: 4

```
Met Ala Pro Gly Glu Arg Asp Ser Trp Ile Asn Pro Gly Pro Asp Ser
1               5                   10                  15

Gln Pro Gly Ala Leu Cys Ser Leu Glu Pro Thr Val Gly Gly Glu Arg
            20                  25                  30

Thr Thr Ser Leu Pro Trp Arg Ala Glu Gly Arg Pro Gly Glu Glu Gly
        35                  40                  45

Ala Ser Ala Gln Leu Leu Gly Gly Trp Pro Val Ser Cys Pro Gly Glu
    50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Ala Val Ala Ala Cys
                165                 170                 175

Val Leu Leu Leu Thr Ser Ala Gln Leu Gly Leu His Ile Trp Gln Leu
```

```
                         180                 185                 190
Arg Ser Gln Cys Met Trp Pro Arg Glu Thr Gln Leu Leu Glu Val
        195                 200                 205
Pro Pro Ser Thr Glu Asp Ala Arg Ser Cys Gln Phe Pro Glu Glu
    210                 215                 220
Arg Gly Glu Arg Ser Ala Glu Glu Lys Gly Arg Leu Gly Asp Leu Trp
225                 230                 235                 240
Val

<210> SEQ ID NO 5
<211> LENGTH: 1074
<212> TYPE: DNA
<213> ORGANISM: Homo sapiens
<220> FEATURE:
<221> NAME/KEY: CDS
<222> LOCATION: (1)..(720)
<220> FEATURE:
<221> NAME/KEY: sig_peptide
<222> LOCATION: (1)..(57)
<220> FEATURE:
<221> NAME/KEY: mat_peptide
<222> LOCATION: (58)..(720)

<400> SEQUENCE: 5 atg ggc gcg ttt cgg gcc ctg tgc ggc ctg gcg ctg ctg tgc gcg ctc      48
Met Gly Ala Phe Arg Ala Leu Cys Gly Leu Ala Leu Leu Cys Ala Leu
                -15                 -10                  -5 agc ctg ggt cag cgc ccc acc ggg ggt ccc ggg tgc ggc cct ggg cgc      96
Ser Leu Gly Gln Arg Pro Thr Gly Gly Pro Gly Cys Gly Pro Gly Arg
         -1   1               5                  10 ctc ctg ctt ggg acg gga acg gac gcg cgc tgc tgc cgg gtt cac acg     144
Leu Leu Leu Gly Thr Gly Thr Asp Ala Arg Cys Cys Arg Val His Thr
         15                  20                  25 acg cgc tgc tgc cgc gat tac ccg gcc cag ctg ctg ggg ggc tgg cct     192
Thr Arg Cys Cys Arg Asp Tyr Pro Ala Gln Leu Leu Gly Gly Trp Pro
 30                  35                  40                  45 gtc tcc tgc cca ggc gag gag tgc tgt tcc gag tgg gac tgc atg tgt     240
Val Ser Cys Pro Gly Glu Glu Cys Cys Ser Glu Trp Asp Cys Met Cys
                 50                  55                  60 gtc cag cct gaa ttc cac tgc gga gac cct tgc tgc acg acc tgc cgg     288
Val Gln Pro Glu Phe His Cys Gly Asp Pro Cys Cys Thr Thr Cys Arg
             65                  70                  75 cac cac cct tgt ccc cca ggc cag ggg gta cag tcc cag ggg aaa ttc     336
His His Pro Cys Pro Pro Gly Gln Gly Val Gln Ser Gln Gly Lys Phe
             80                  85                  90 agt ttt ggc ttc cag tgt atc gac tgt gcc tcg ggg acc ttc tcc ggg     384
Ser Phe Gly Phe Gln Cys Ile Asp Cys Ala Ser Gly Thr Phe Ser Gly
         95                 100                 105 ggc cac gaa ggc cac tgc aaa cct tgg aca gac tgc acc cag ttc ggg     432
Gly His Glu Gly His Cys Lys Pro Trp Thr Asp Cys Thr Gln Phe Gly
110                 115                 120                 125 ttt ctc act gtg ttc cct ggg aac aag acc cac aac gct gtg tgc gtc     480
Phe Leu Thr Val Phe Pro Gly Asn Lys Thr His Asn Ala Val Cys Val
                130                 135                 140 cca ggg tcc ccg ccg gca gag ccg ctt ggg tgg ctg acc gtc gtc ctc     528
Pro Gly Ser Pro Pro Ala Glu Pro Leu Gly Trp Leu Thr Val Val Leu
            145                 150                 155 ctg gcc gtg gcc gcc tgc gtc ctc ctg acc tcg gcc cag ctt gga     576
Leu Ala Val Ala Ala Cys Val Leu Leu Leu Thr Ser Ala Gln Leu Gly
            160                 165                 170 ctg cac atc tgg cag ctg agg aag acc cag ctg ctg ctg gag gtg ccg     624
```

```
Leu His Ile Trp Gln Leu Arg Lys Thr Gln Leu Leu Leu Glu Val Pro
        175                 180                 185 ccg tcg acc gaa gac gcc aga agc tgc cag ttc ccc gag gaa gag cgg       672
Pro Ser Thr Glu Asp Ala Arg Ser Cys Gln Phe Pro Glu Glu Glu Arg
190                 195                 200                 205 ggc gag cga tcg gca gag gag aag ggg cgg ctg gga gac ctg tgg gtg       720
Gly Glu Arg Ser Ala Glu Glu Lys Gly Arg Leu Gly Asp Leu Trp Val
                    210                 215                 220 tgagcctggc cgtcctccgg ggccaccgac cgcagccagc ccctcccag gagctcccca      780 ggccgcaggg gctctgcgtt ctgctctggg ccgggccctg ctccctggc agcagaagtg      840 ggtgcaggaa ggtggcagtg accagcgccc tggaccatgc agttcggcgg ccgcggctgg     900
gccctgcagg aggagagag agacacagtc atgccccct cctcccttg ctggccctga       960 tggggtgggg tcttaggacg ggaggctgtg tccgtgggtg tgcagtgccc agcacgggac    1020
ccggctgcag gggaccttca ataaacactt gtccagtaaa aaaaaaaaaa aaaa         1074

<210> SEQ ID NO 6
<211> LENGTH: 240
<212> TYPE: PRT
<213> ORGANISM: Homo sapiens

<400> SEQUENCE: 6

Met Gly Ala Phe Arg Ala Leu Cys Gly Leu Ala Leu Leu Cys Ala Leu
                -15                 -10                  -5

Ser Leu Gly Gln Arg Pro Thr Gly Gly Pro Gly Cys Gly Pro Gly Arg
         -1   1                  5                  10

Leu Leu Leu Gly Thr Gly Thr Asp Ala Arg Cys Cys Arg Val His Thr
             15                  20                  25

Thr Arg Cys Cys Arg Asp Tyr Pro Ala Gln Leu Leu Gly Gly Trp Pro
 30                  35                  40                  45

Val Ser Cys Pro Gly Glu Glu Cys Cys Ser Glu Trp Asp Cys Met Cys
                 50                  55                  60

Val Gln Pro Glu Phe His Cys Gly Asp Pro Cys Cys Thr Thr Cys Arg
                 65                  70                  75

His His Pro Cys Pro Pro Gly Gln Gly Val Gln Ser Gln Gly Lys Phe
             80                  85                  90

Ser Phe Gly Phe Gln Cys Ile Asp Cys Ala Ser Gly Thr Phe Ser Gly
         95                 100                 105

Gly His Glu Gly His Cys Lys Pro Trp Thr Asp Cys Thr Gln Phe Gly
110                 115                 120                 125

Phe Leu Thr Val Phe Pro Gly Asn Lys Thr His Asn Ala Val Cys Val
             130                 135                 140

Pro Gly Ser Pro Pro Ala Glu Pro Leu Gly Trp Leu Thr Val Val Leu
                 145                 150                 155

Leu Ala Val Ala Ala Cys Val Leu Leu Leu Thr Ser Ala Gln Leu Gly
             160                 165                 170

Leu His Ile Trp Gln Leu Arg Lys Thr Gln Leu Leu Leu Glu Val Pro
             175                 180                 185

Pro Ser Thr Glu Asp Ala Arg Ser Cys Gln Phe Pro Glu Glu Glu Arg
190                 195                 200                 205

Gly Glu Arg Ser Ala Glu Glu Lys Gly Arg Leu Gly Asp Leu Trp Val
                    210                 215                 220

<210> SEQ ID NO 7
<211> LENGTH: 228
```

```
<212> TYPE: PRT
<213> ORGANISM: Mus musculus

<400> SEQUENCE: 7
```

| | | | | | | | | | | | | | | | |
|---|---|---|---|---|---|---|---|---|---|---|---|---|---|---|---|
| Met | Gly | Ala | Trp | Ala | Met | Leu | Tyr | Gly | Val | Ser | Met | Leu | Cys | Val | Leu |
| 1 | | | | 5 | | | | | 10 | | | | | 15 | |
| Asp | Leu | Gly | Gln | Pro | Ser | Val | Val | Glu | Glu | Pro | Gly | Cys | Gly | Pro | Gly |
| | | | 20 | | | | | 25 | | | | | 30 | | |
| Lys | Val | Gln | Asn | Gly | Ser | Gly | Asn | Asn | Thr | Arg | Cys | Cys | Ser | Leu | Tyr |
| | | | 35 | | | | | 40 | | | | | 45 | | |
| Ala | Pro | Gly | Lys | Glu | Asp | Cys | Pro | Lys | Glu | Arg | Cys | Ile | Cys | Val | Thr |
| | | 50 | | | | | 55 | | | | | 60 | | | |
| Pro | Glu | Tyr | His | Cys | Gly | Asp | Pro | Gln | Cys | Lys | Ile | Cys | Lys | His | Tyr |
| 65 | | | | | 70 | | | | | 75 | | | | | 80 |
| Pro | Cys | Gln | Pro | Gly | Gln | Arg | Val | Glu | Ser | Gln | Gly | Asp | Ile | Val | Phe |
| | | | | 85 | | | | | 90 | | | | | 95 | |
| Gly | Phe | Arg | Cys | Val | Ala | Cys | Ala | Met | Gly | Thr | Phe | Ser | Ala | Gly | Arg |
| | | | 100 | | | | | 105 | | | | | 110 | | |
| Asp | Gly | His | Cys | Arg | Leu | Trp | Thr | Asn | Cys | Ser | Gln | Phe | Gly | Phe | Leu |
| | | | 115 | | | | | 120 | | | | | 125 | | |
| Thr | Met | Phe | Pro | Gly | Asn | Lys | Thr | His | Asn | Ala | Val | Cys | Ile | Pro | Glu |
| | | 130 | | | | | 135 | | | | | 140 | | | |
| Pro | Leu | Pro | Thr | Glu | Gln | Tyr | Gly | His | Leu | Thr | Val | Ile | Phe | Leu | Val |
| 145 | | | | | 150 | | | | | 155 | | | | | 160 |
| Met | Ala | Ala | Cys | Ile | Phe | Phe | Leu | Thr | Thr | Val | Gln | Leu | Gly | Leu | His |
| | | | | 165 | | | | | 170 | | | | | 175 | |
| Ile | Trp | Gln | Leu | Arg | Arg | Gln | His | Met | Cys | Pro | Arg | Glu | Thr | Gln | Pro |
| | | | 180 | | | | | 185 | | | | | 190 | | |
| Phe | Ala | Glu | Val | Gln | Leu | Ser | Ala | Glu | Asp | Ala | Cys | Ser | Phe | Gln | Phe |
| | | | 195 | | | | | 200 | | | | | 205 | | |
| Pro | Glu | Glu | Glu | Arg | Gly | Glu | Gln | Thr | Glu | Glu | Lys | Cys | His | Leu | Gly |
| | | 210 | | | | | 215 | | | | | 220 | | | |
| Gly | Arg | Trp | Pro | | | | | | | | | | | | |
| 225 | | | | | | | | | | | | | | | |

```
<210> SEQ ID NO 8
<211> LENGTH: 466
<212> TYPE: DNA
<213> ORGANISM: Homo sapiens
<220> FEATURE:
<221> NAME/KEY: misc_feature
<222> LOCATION: (323)
<223> OTHER INFORMATION: n equals a, t, g or c
<220> FEATURE:
<221> NAME/KEY: misc_feature
<222> LOCATION: (337)
<223> OTHER INFORMATION: n equals a, t, g or c
<220> FEATURE:
<221> NAME/KEY: misc_feature
<222> LOCATION: (392)
<223> OTHER INFORMATION: n equals a, t, g or c
<220> FEATURE:
<221> NAME/KEY: misc_feature
<222> LOCATION: (406)
<223> OTHER INFORMATION: n equals a, t, g or c
<220> FEATURE:
<221> NAME/KEY: misc_feature
<222> LOCATION: (441)
<223> OTHER INFORMATION: n equals a, t, g or c
<220> FEATURE:
<221> NAME/KEY: misc_feature
<222> LOCATION: (452)
<223> OTHER INFORMATION: n equals a, t, g or c
```

-continued

```
<400> SEQUENCE: 8
gcgcacttca cctgggtcgg gattctcagg tcatgaacgg tcccagccac ctccgggcag      60
ggcgggtgag gacggggacg gggcgtgtcc aactggctgt gggctcttga aacccgagca    120
tggcacagca cggggcgatg ggcgcgtttc gggccctgtg cggcctggcg ctgctgtgcg    180
cgctcagcct gggtcagcgc cccaccgggg gtcccggtg cggccctggg cgcctcctgc     240
ttgggacggg aaaggacgcg cgctgcttgc cggggtttca acacgaacgc gctgctgccg    300
cgattaaccc ggggcgaaga atngtggttt ccgagtnggg aactgcaatg tgttgttcaa    360
gccttgaaat tccaattgcg gaagaaccct tngcttgcaa cgaacntgcc cgggaaacaa    420
acctttgttc ccccaaagcc naaggggta anaattccca ggggga                    466

<210> SEQ ID NO 9
<211> LENGTH: 581
<212> TYPE: DNA
<213> ORGANISM: Homo sapiens
<220> FEATURE:
<221> NAME/KEY: misc_feature
<222> LOCATION: (291)
<223> OTHER INFORMATION: n equals a, t, g or c
<220> FEATURE:
<221> NAME/KEY: misc_feature
<222> LOCATION: (293)
<223> OTHER INFORMATION: n equals a, t, g or c
<220> FEATURE:
<221> NAME/KEY: misc_feature
<222> LOCATION: (295)
<223> OTHER INFORMATION: n equals a, t, g or c
<220> FEATURE:
<221> NAME/KEY: misc_feature
<222> LOCATION: (319)
<223> OTHER INFORMATION: n equals a, t, g or c
<220> FEATURE:
<221> NAME/KEY: misc_feature
<222> LOCATION: (402)
<223> OTHER INFORMATION: n equals a, t, g or c
<220> FEATURE:
<221> NAME/KEY: misc_feature
<222> LOCATION: (424)
<223> OTHER INFORMATION: n equals a, t, g or c
<220> FEATURE:
<221> NAME/KEY: misc_feature
<222> LOCATION: (452)
<223> OTHER INFORMATION: n equals a, t, g or c
<220> FEATURE:
<221> NAME/KEY: misc_feature
<222> LOCATION: (440)
<223> OTHER INFORMATION: n equals a, t, g or c
<220> FEATURE:
<221> NAME/KEY: misc_feature
<222> LOCATION: (471)
<223> OTHER INFORMATION: n equals a, t, g or c
<220> FEATURE:
<221> NAME/KEY: misc_feature
<222> LOCATION: (483)
<223> OTHER INFORMATION: n equals a, t, g or c
<220> FEATURE:
<221> NAME/KEY: misc_feature
<222> LOCATION: (495)
<223> OTHER INFORMATION: n equals a, t, g or c
<220> FEATURE:
<221> NAME/KEY: misc_feature
<222> LOCATION: (516)
<223> OTHER INFORMATION: n equals a, t, g or c
<220> FEATURE:
<221> NAME/KEY: misc_feature
<222> LOCATION: (545)
<223> OTHER INFORMATION: n equals a, t, g or c
<220> FEATURE:
<221> NAME/KEY: misc_feature
<222> LOCATION: (559)
```

<223> OTHER INFORMATION: n equals a, t, g or c

<400> SEQUENCE: 9

| | | | | | |
|---|---|---|---|---|---|
| gggtcgaccc | acgcgtccgg | ggggccaccc | tgggtcctgc | aggggcagct | cctggttgca | 60 |
| tatggagtta | gcacctgggc | aggggcagct | gtggggcgca | aaggggagt | agccaggcca | 120 |
| catggcccca | ggagaaagag | acagctggat | aaacccaggg | tccagactcc | cagccaggga | 180 |
| gccctctgct | ccctggagcc | aactgtgggt | ggagaacgga | caacctcact | cccctggtag | 240 |
| ggccgagggg | aggcctgggg | aggaggggc | ctcagcccag | ctgctggggg | nanannctgt | 300 |
| ctcctgccca | ggcgaggant | gctgttccga | gtgggaatgc | atgtgtgtcc | agcctgaatt | 360 |
| ccattgcgga | gaaccttgct | gcacgaattg | ccggcaacaa | cntgttcccc | caagccaggg | 420 |
| ggtnacattc | ccaggggaan | ttcattttg | gnttccatgt | ttcgatgtgc | ntcggggaat | 480 |
| ttntccgggg | gccanaaggc | aatgcaaaac | ttgganaaag | gaccatttcg | gttttcacgg | 540 |
| ttccngggaa | aagaccanaa | gttttggtc | caggtccccc | g | | 581 |

<210> SEQ ID NO 10
<211> LENGTH: 22
<212> TYPE: DNA
<213> ORGANISM: Homo sapiens

<400> SEQUENCE: 10
cgcccatggc agcgccccac cg                                         22

<210> SEQ ID NO 11
<211> LENGTH: 22
<212> TYPE: DNA
<213> ORGANISM: Homo sapiens

<400> SEQUENCE: 11
cgcaagcttg gctctgccgg cg                                         22

<210> SEQ ID NO 12
<211> LENGTH: 22
<212> TYPE: DNA
<213> ORGANISM: Homo sapiens

<400> SEQUENCE: 12
cgcggatccc agcgccccac cg                                         22

<210> SEQ ID NO 13
<211> LENGTH: 22
<212> TYPE: DNA
<213> ORGANISM: Homo sapiens

<400> SEQUENCE: 13
cgcggtaccg gctctgccgg cg                                         22

<210> SEQ ID NO 14
<211> LENGTH: 35
<212> TYPE: DNA
<213> ORGANISM: Homo sapiens

<400> SEQUENCE: 14
cgcggatccc cgccatcatg gcacagcacg ggcg                            35

<210> SEQ ID NO 15
<211> LENGTH: 25
<212> TYPE: DNA
<213> ORGANISM: Homo sapiens

```
<400> SEQUENCE: 15
cgcggtaccc acccacaggt ctccc                                          25

<210> SEQ ID NO 16
<211> LENGTH: 31
<212> TYPE: DNA
<213> ORGANISM: Homo sapiens

<400> SEQUENCE: 16
cgcggatccg ccatcatgca gcgccccacc g                                   31

<210> SEQ ID NO 17
<211> LENGTH: 55
<212> TYPE: DNA
<213> ORGANISM: Homo sapiens

<400> SEQUENCE: 17
cgctctagat caagcgtagt ctgggacgtc gtatgggtat taggctctgc cggcg         55

<210> SEQ ID NO 18
<211> LENGTH: 733
<212> TYPE: DNA
<213> ORGANISM: Homo sapiens

<400> SEQUENCE: 18
gggatccgga gcccaaatct tctgacaaaa ctcacacatg cccaccgtgc ccagcacctg    60
aattcgaggg tgcaccgtca gtcttcctct tccccccaaa acccaaggac accctcatga  120
tctcccggac tcctgaggtc acatgcgtgg tggtggacgt aagccacgaa gaccctgagg  180
tcaagttcaa ctggtacgtg gacggcgtgg aggtgcataa tgccaagaca aagccgcggg  240
aggagcagta caacagcacg taccgtgtgg tcagcgtcct caccgtcctg caccaggact  300
ggctgaatgg caaggagtac aagtgcaagg tctccaacaa agccctccca accccatcg   360 agaaaaccat ctccaaagcc aaagggcagc ccgagaacc acaggtgtac accctgcccc    420
catcccggga tgagctgacc aagaaccagg tcagcctgac ctgcctggtc aaaggcttct  480
atccaagcga catcgccgtg gagtgggaga gcaatgggca gccggagaac aactacaaga  540
ccacgcctcc cgtgctggac tccgacggct ccttcttcct ctacagcaag ctcaccgtgg  600
acaagagcag gtggcagcag gggaacgtct tctcatgctc cgtgatgcat gaggctctgc  660
acaaccacta cacgcagaag agcctctccc tgtctccggg taaatgagtg cgacggccgc  720
gactctagag gat                                                     733

<210> SEQ ID NO 19
<211> LENGTH: 86
<212> TYPE: DNA
<213> ORGANISM: Homo sapiens

<400> SEQUENCE: 19
gcgcctcgag atttccccga aatctagatt tccccgaaat gatttccccg aaatgatttc    60
cccgaaatat ctgccatctc aattag                                        86

<210> SEQ ID NO 20
<211> LENGTH: 27
<212> TYPE: DNA
<213> ORGANISM: Homo sapiens

<400> SEQUENCE: 20
```
gcggcaagct ttttgcaaag cctaggc                                        27

<210> SEQ ID NO 21
<211> LENGTH: 271
<212> TYPE: DNA
<213> ORGANISM: Homo sapiens

<400> SEQUENCE: 21
ctcgagattt ccccgaaatc tagatttccc cgaaatgatt tccccgaaat gatttccccg    60
aaatatctgc catctcaatt agtcagcaac catagtcccg cccctaactc cgcccatccc   120
gcccctaact ccgcccagtt ccgcccattc tccgcccat ggctgactaa ttttttttat    180
ttatgcagag gccgaggccg cctcggcctc tgagctattc cagaagtagt gaggaggctt   240
ttttggaggc ctaggctttt gcaaaaagct t                                  271

<210> SEQ ID NO 22
<211> LENGTH: 32
<212> TYPE: DNA
<213> ORGANISM: Homo sapiens

<400> SEQUENCE: 22
gcgctcgagg gatgacagcg atagaacccc gg                                  32

<210> SEQ ID NO 23
<211> LENGTH: 31
<212> TYPE: DNA
<213> ORGANISM: Homo sapiens

<400> SEQUENCE: 23
gcgaagcttc gcgactcccc ggatccgcct c                                   31

<210> SEQ ID NO 24
<211> LENGTH: 12
<212> TYPE: DNA
<213> ORGANISM: Homo sapiens

<400> SEQUENCE: 24
ggggactttc cc                                                        12

<210> SEQ ID NO 25
<211> LENGTH: 73
<212> TYPE: DNA
<213> ORGANISM: Homo sapiens

<400> SEQUENCE: 25
gcggcctcga ggggactttc ccggggactt tccgggactt tccgggact ttccatcctg     60 ccatctcaat tag                                                       73

<210> SEQ ID NO 26
<211> LENGTH: 27
<212> TYPE: DNA
<213> ORGANISM: Homo sapiens

<400> SEQUENCE: 26
gcggcaagct ttttgcaaag cctaggc                                        27

<210> SEQ ID NO 27
<211> LENGTH: 256
<212> TYPE: DNA
<213> ORGANISM: Homo sapiens

<400> SEQUENCE: 27

-continued

```
ctcgagggga ctttcccggg gactttccgg ggactttccg ggactttcca tctgccatct      60
caattagtca gcaaccatag tcccgcccct aactccgccc atcccgcccc taactccgcc     120
cagttccgcc cattctccgc cccatggctg actaattttt tttatttatg cagaggccga     180
ggccgcctcg gcctctgagc tattccagaa gtagtgagga ggcttttttg gaggcctagg     240
cttttgcaaa aagctt                                                    256
```

HUMAN TUMOR NECROSIS FACTOR RECEPTOR-LIKE PROTEINS TR11, TR11SV1, AND TR11SV2

This application claims benefit under 35 U.S.C. §119(e) of the filing date of copending U.S. Provisional Application Serial No. 60/063,212, filed on Oct. 21, 1997, which is hereby incorporated by reference in its entirety.

FIELD OF THE INVENTION

The present invention relates to novel members of the Tumor Necrosis Factor (TNF) receptor family. More specifically, isolated nucleic acid molecules are provided encoding a human TNF receptor-related protein, referred to herein as the TR11 receptor of FIGS. 1A and 1B, and two splice variants thereof, referred to herein as the TR11SV1 and TR11SV2 receptors, of FIGS. 2A and 2B and 3A and 3B, respectively, each having considerable homology to murine glucocorticoid-induced tumor necrosis factor receptor family-related gene (GITR). TR11, TR11SV1, and TR11SV2 polypeptides are also provided. Further provided are vectors, host cells and recombinant methods for producing the same. The invention also relates to both the inhibition and enhancement of the activities of TR11, TR11SV1, and TR11SV2 receptor polypeptides and diagnostic methods for detecting TR11 receptor gene expression.

BACKGROUND OF THE INVENTION

Human tumor necrosis factors α (TNF-α) and β (TNF-β or lymphotoxin) are related members of a broad class of polypeptide mediators, which includes the interferons, interleukins and growth factors, collectively called cytokines (Beutler, B. and Cerami, A., Annu. Rev. Immunol., 7:625–655 (1989)).

Tumor necrosis factor (TNF-α and TNF-β) was originally discovered as a result of its anti-tumor activity, however, now it is recognized as a pleiotropic cytokine playing important roles in a host of biological processes and pathologies. To date, there are ten known members of the TNF-related cytokine family, TNF-α, TNF-β (lymphotoxin-α), LT-β, TRAIL and ligands for the Fas receptor, CD30, CD27, CD40 (also known as CDw40), OX40 and 4-1BB receptors. These proteins have conserved C-terminal sequences and variable N-terminal sequences which are often used as membrane anchors, with the exception of TNF-β. Both TNF-α and TNF-β function as homotrimers when they bind to TNF receptors.

TNF is produced by a number of cell types, including monocytes, fibroblasts, T-cells, natural killer (NK) cells and predominately by activated macrophages. TNF-α has been reported to have a role in the rapid necrosis of tumors, immunostimulation, autoimmune disease, graft rejection, producing an anti-viral response, septic shock, cerebral malaria, cytotoxicity, protection against deleterious effects of ionizing radiation produced during a course of chemotherapy, such as denaturation of enzymes, lipid peroxidation and DNA damage (Nata, et al., J. Immunol. 136:2483 (1987)), growth regulation, vascular endothelium effects and metabolic effects. TNF-α also triggers endothelial cells to secrete various factors, including PAI-1, IL-1, GM-CSF and IL-6 to promote cell proliferation. In addition, TNF-α up-regulates various cell adhesion molecules such as E-Selectin, ICAM-1 and VCAM-1. TNF-α and the Fas ligand have also been shown to induce programmed cell death.

TNF-β has many activities, including induction of an antiviral state and tumor necrosis, activation of polymorphonuclear leukocytes, induction of class I major histocompatibility complex antigens on endothelial cells, induction of adhesion molecules on endothelium and growth hormone stimulation (Ruddle, N. and Homer, R., Prog. Allergy 40:162–182 (1988)).

Both TNF-α and TNF-β are involved in growth regulation and interact with hemopoietic cells at several stages of differentiation, inhibiting proliferation of various types of precursor cells, and inducing proliferation of immature myelomonocytic cells (Porter, A., Tibtech 9:158–162 (1991)).

Recent studies with "knockout" mice have shown that mice deficient in TNF-β production show abnormal development of the peripheral lymphoid organs and morphological changes in spleen architecture (reviewed by Aggarwal, et al., Eur Cytokine Netw, 7:93–124 (1996)). With respect to the lymphoid organs, the popliteal, inguinal, para-aortic, mesenteric, axillary and cervical lymph nodes failed to develop in TNF-β–/– mice. In addition, peripheral blood from TNF-β–/– mice contained a three fold reduction in white blood cells as compared to normal mice. Peripheral blood from TNF-β–/– mice, however, contained four fold more B cells as compared to their normal counterparts. Further, TNF-β, in contrast to TNF-α, has been shown to induce proliferation of EBV-infected B cells. These results indicate that TNF-β is involved in lymphocyte development.

The first step in the induction of the various cellular responses mediated by TNF-α or TNF-β is their binding to specific cell surface or soluble receptors. Two distinct TNF receptors of approximately 55-KDa (TNF-RI) and 75-KDa (TNF-RII) have been identified (Hohman, et al., J. Biol. Chem., 264:14927–14934 (1989)), and human and mouse cDNAs corresponding to both receptor types have been isolated and characterized (Loetscher, et al., Cell, 61:351 (1990)). Both TNF-Rs share the typical structure of cell surface receptors including extracellular, transmembrane and intracellular regions.

These molecules exist not only in cell bound forms, but also in soluble forms, consisting of the cleaved extra-cellular domains of the intact receptors (Nophar, et al., EMBO Journal, 9:3269–76 (1990)) and otherwise intact receptors wherein the transmembrane domain is lacking. The extra-cellular domains of TNF-RI and TNF-RII share 28% identity and are characterized by four repeated cysteine-rich motifs with significant intersubunit sequence homology. The majority of cell types and tissues appear to express both TNF receptors and both receptors are active in signal transduction, however, they are able to mediate distinct cellular responses. Further, TNF-RII was shown to exclusively mediate human T-cell proliferation by TNF as shown in PCT WO 94/09137.

TNF-RI dependent responses include accumulation of C-FOS, IL-6, and manganese superoxide dismutase mRNA, prostaglandin E2 synthesis, IL-2 receptor and MHC class I and II cell surface antigen expression, growth inhibition, and cytotoxicity. TNF-RI also triggers second messenger systems such as phospholipase A, protein kinase C, phosphatidylcholine-specific phospholipase C and sphingomyelinase (Pfefferk, et al., Cell, 73:457–467 (1993)).

Several interferons and other agents have been shown to regulate the expression of TNF receptors. Retinoic acid, for example, has been shown to induce the production of TNF receptors in some cells type while down regulating production in other cells. In addition, TNF-α has been shown to affect the localization of both types of receptor. TNF-α induces internalization of TNF-RI and secretion of TNF-RII (reviewed in Aggarwal, et al., supra). Thus, the production and localization of both TNF-Rs are regulated by a variety of agents.

Both the yeast two hybrid system and co-precipitation and purification have been used to identify ligands which associate with both types of the TNF-Rs (reviewed by Aggarwal, et al., supra; Vandenabeele, et al., *Trends in Cell Biol.* 5:392–399 (1995)). Several proteins have been identified which interact with the cytoplasmic domain of a murine TNF-R. Two of these proteins appear to be related to the baculovirus inhibitor of apoptosis, suggesting a direct role for TNF-R in the regulation of programmed cell death.

Thus, there is a need for polypeptides that function as receptors for cytokines and cytokine-like molecules which are involved in the regulation of cellular processes such as cell-growth and differentiation, since disturbances of such regulation may be involved in disorders relating to hemostasis, angiogenesis, tumor metastisis, cellular migration, and neurogenesis. Therefore, there is a need for identification and characterization of such human polypeptides which can play a role in detecting, preventing, ameliorating, regulating or correcting such disorders.

SUMMARY OF THE INVENTION

The present invention provides isolated nucleic acid molecules comprising polynucleotides encoding TR11, TR11SV1, and TR11SV2 receptors having the amino acid sequences shown in FIGS. 1A and 1B (SEQ ID NO:2), 2A and 2B (SEQ ID NO:4), and 3A and 3B (SEQ ID NO:6), respectively, or the amino acid sequences encoded by the cDNA clones encoding the TR11, TR11SV1, and TR11SV2 receptors, respectively, deposited as ATCC Deposit Numbers 209341, 209343, and 209342 respectively, on Oct. 7, 1997. The present invention also relates to recombinant vectors, which include the isolated nucleic acid molecules of the present invention, and to host cells containing the recombinant vectors, as well as to methods of making such vectors and host cells and for using them for production of TR11, TR11SV1, and TR11SV2 polypeptides or peptides by recombinant techniques.

The invention further provides isolated TR11, TR11SV1, and TR11SV2 polypeptides having amino acid sequences encoded by the polynucleotides described herein.

The present invention also provides a screening method for identifying compounds capable of enhancing or inhibiting a cellular response induced by TR11, TR11SV1, and TR11SV2 receptors, which involves contacting cells which express TR11, TR11SV1 or TR11SV2 receptors with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

In another aspect, a screening assay for agonists and antagonists is provided which involves determining the effect a candidate compound has on the binding of cellular ligands to TR11, TR11SV1, and TR11SV2 receptors. In particular, the method involves contacting TR11, TR11SV1, and TR11SV2 receptors with a ligand polypeptide and a candidate compound and determining whether ligand binding to the TR11, TR11SV1, and TR11SV2 receptors is increased or decreased due to the presence of the candidate compound.

The invention further provides a diagnostic method useful during diagnosis or prognosis of a disease states resulting from aberrant cell proliferation due to alterations in TR11, TR11SV1, and TR11SV2 receptor expression.

An additional aspect of the invention is related to a method for treating an individual in need of an increased level of a TR11, TR11SV1 or TR11SV2 receptor activity in the body comprising administering to such an individual a composition comprising a therapeutically effective amount of isolated TR11, TR11SV1 or TR11SV2 polypeptides of the invention or an agonist thereof.

A still further aspect of the invention is related to a method for treating an individual in need of a decreased level of a TR11, TR11SV1 or TR11SV2 receptor activity in the body comprising, administering to such an individual a composition comprising a therapeutically effective amount of a TR11, TR11SV1 or TR11SV2 receptor antagonist.

The invention additionally provides soluble forms of the polypeptides of the present invention. Soluble peptides are defined by amino acid sequences wherein the sequence comprises the polypeptide sequence lacking a transmembrane domain. Such soluble forms of the TR11, TR11SV1, and TR11SV2 receptors are useful as antagonists of the membrane bound forms of the receptors.

BRIEF DESCRIPTION OF THE FIGURES

FIGS. 1A and 1B show the nucleotide (SEQ ID NO:1) and deduced amino acid (SEQ ID NO:2) sequence of a TR11 receptor. A potential secretory leader sequence has been predicted for the complete polypeptide, of about 25 amino acid residues. The predicted secretory leader sequence is underlined in FIGS. 1A and 1B (amino acid residues −25 to −1 in SEQ ID NO:2). The deduced complete amino acid sequence includes 234 amino acid residues and has a deduced molecular weight of about 25,113 Da. It is further predicted that amino acid residues from about 26 to about 162 in FIGS. 1A and 1B (amino acid residues 1 to 137 in SEQ ID NO:2) constitute the extracellular domain; from about 163 to about 179 (amino acid residues 138 to 154 in SEQ ID NO:2) constitute the transmembrane domain; and from about 180 to about 234 (amino acid residues 155 to 209 in SEQ ID NO:2) constitute the intracellular domain.

FIGS. 2A and 2B shows the nucleotide (SEQ ID NO:3) and deduced amino acid (SEQ ID NO:4) sequence of a TR11SV1 receptor. The deduced complete amino acid sequence includes 241 amino acid residues and has a deduced molecular weight of about 26,029 Da. It is further predicted that amino acid residues from about 1 to about 162 in FIGS. 2A and 2B (amino acid residues 1 to 162 in SEQ ID NO:4) constitute the extracellular domain; from about 163 to about 179 (amino acid residues 163 to 179 in SEQ ID NO:4) the transmembrane domain; and from about 180 to about 241 (amino acid residues 180 to 241 in SEQ ID NO:4) the intracellular domain.

FIGS. 3A and 3B shows the nucleotide (SEQ ID NO:5) and deduced amino acid (SEQ ID NO:6) sequence of a TR11SV2 receptor. A potential secretory leader sequence has been predicted for the complete polypeptide, of about 19 amino acid residues. The predicted secretory leader sequence is underlined in FIGS. 3A and 3B (amino acid residues −19 to −1 in SEQ ID NO:6). The deduced complete amino acid sequence includes 240 amino acid residues and has a deduced molecular weight of about 25,727 Da. It is further predicted that amino acid residues from about 20 to about 168 in FIGS. 3A and 3B (amino acid residues 1 to 149 in SEQ ID NO:6) constitute the extracellular domain; from about 169 to about 185 (amino acid residues 150 to 166 in SEQ ID NO:6) the transmembrane domain; and from about 186 to about 240 (amino acid residues 167 to 221 in SEQ ID NO:6) the intracellular domain.

A single potential asparagine-linked glycosylation site is marked in the amino acid sequence of TR11, TR11SV1,and TR11SV2. The potential site of glycosylation is at asparagine-146 in FIGS. 1A and 1B (asparagine-121 in SEQ ID NO:2), asparagine-146 in FIGS. 2A and 2B (asparagine-146 in SEQ ID NO:4), and asparagine-152 in FIGS. 3A and 3B (asparagine-133 in SEQ ID NO:6). The potential glycosylation sites are marked with a bold pound symbol (#) above the nucleotide sequence coupled with a bolded one letter abbreviation for the asparagine (N) in the amino acid sequence in FIGS. 1A and 1B, 2A and 2B, and 3A and 3B.

Regions of high identity between TR11, TR11SV1, and TR11SV2 and the closely related murine GITR (an aligment of these sequences is presented in FIGS. 4A and 4B) are delineated in FIGS. 1A and 1B, 2A and 2B, and 3A and 3B with a double underline. These regions are not limiting and are labeled as Conserved Domain (CD)-II, CD-III, CD-IV, CD-V, CD-VI, CD-VII, CD-IX, and CD-X in FIGS. 1A and 1B, 2A and 2B, and 3A and 3B. Conserved Domain (CD)-I is found only in TR11SV1 and TR11SV2 (i.e., FIGS. 2A and 2B and 3A and 3B) and CD-VIII is found only in TR11SV1 (i.e., FIGS. 2A and 2B).

Figure 4A:
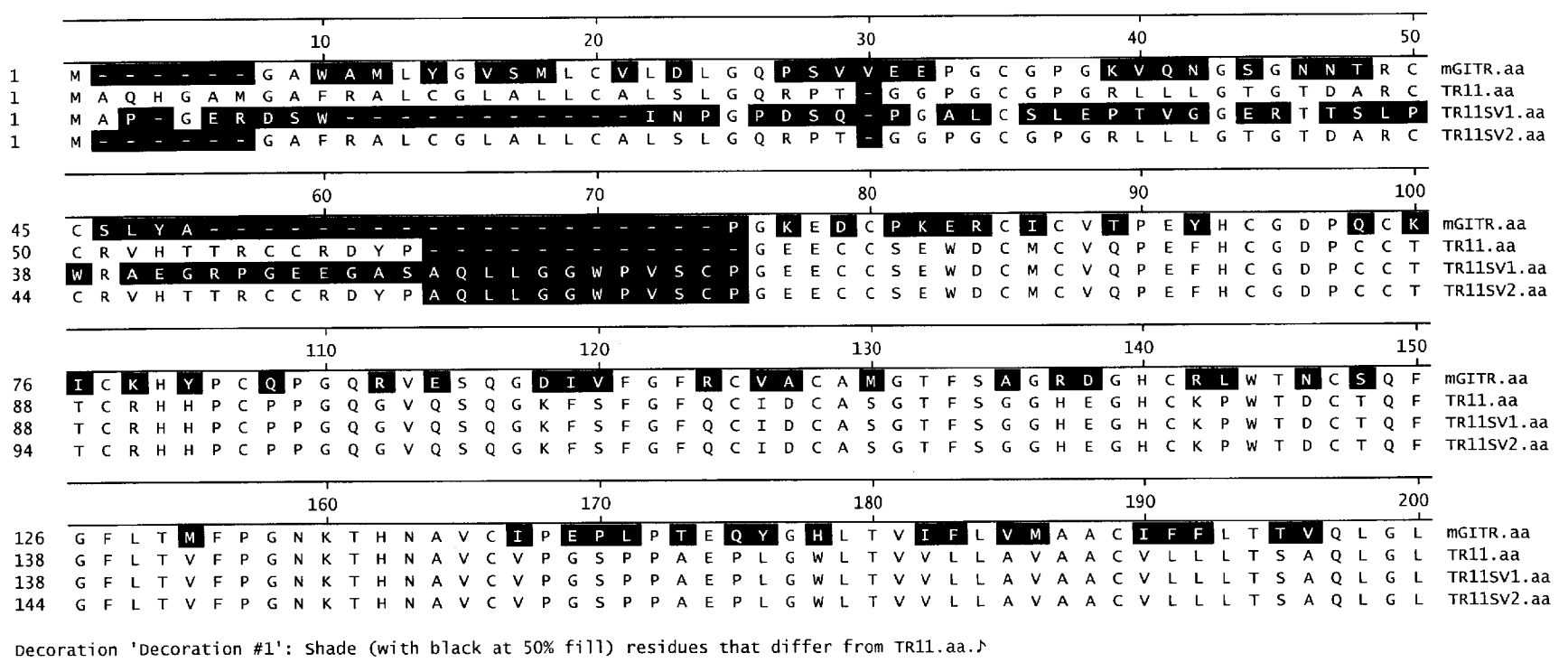

FIGS. 4A and 4B show an alignment of the amino acid sequences of the murine glucocorticoid-induced tumor necrosis factor receptor family-related gene (GITR) receptor-like molecule, TR11, TR11SV1, and TR11SV2 (SEQ ID NO:7, SEQ ID NO:2, SEQ ID NO:4, and SEQ ID NO:6, respectively). The numbering of the TR11 amino acid sequences shown in this figure are relative to that presented in FIGS. 1A and 1B, 2A and 2B, and 3A and 3B, respectively. The alignment was generated using the "MegAlign" module of the DNA*Star Sequence Analysis computer program (DNASTAR, Inc.). Amino acid residues of mGITR, TR11SV1, and TR11SV2 which do not have identity with those of TR11 are highlighted in black in the alignment. The GenBank Accession No. for mGITR is U82534 (Nocentini, G., et al., *Circ. Proc. Natl. Acad. Sci. USA* 94:6216–6221 (1997)).

Figure 5:
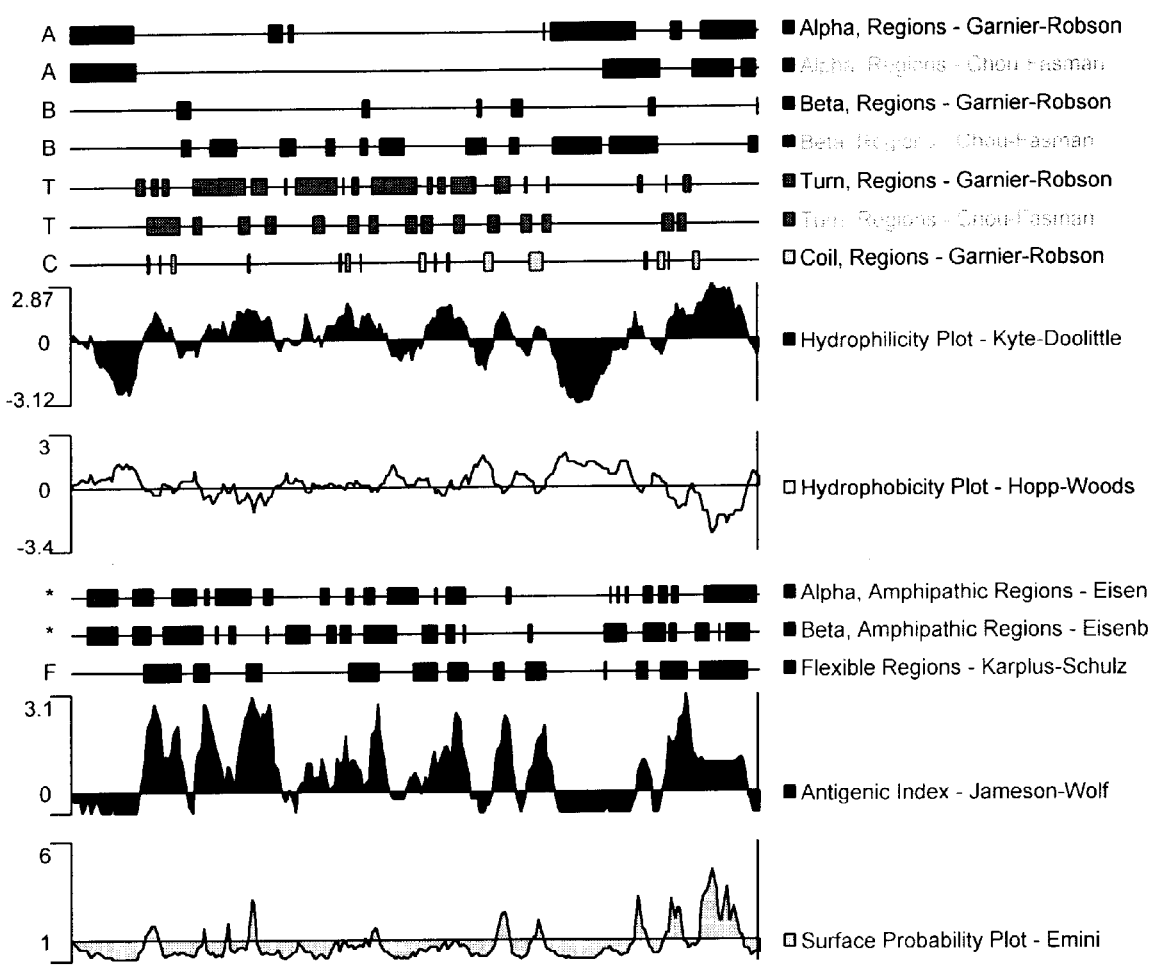
Figure 6:
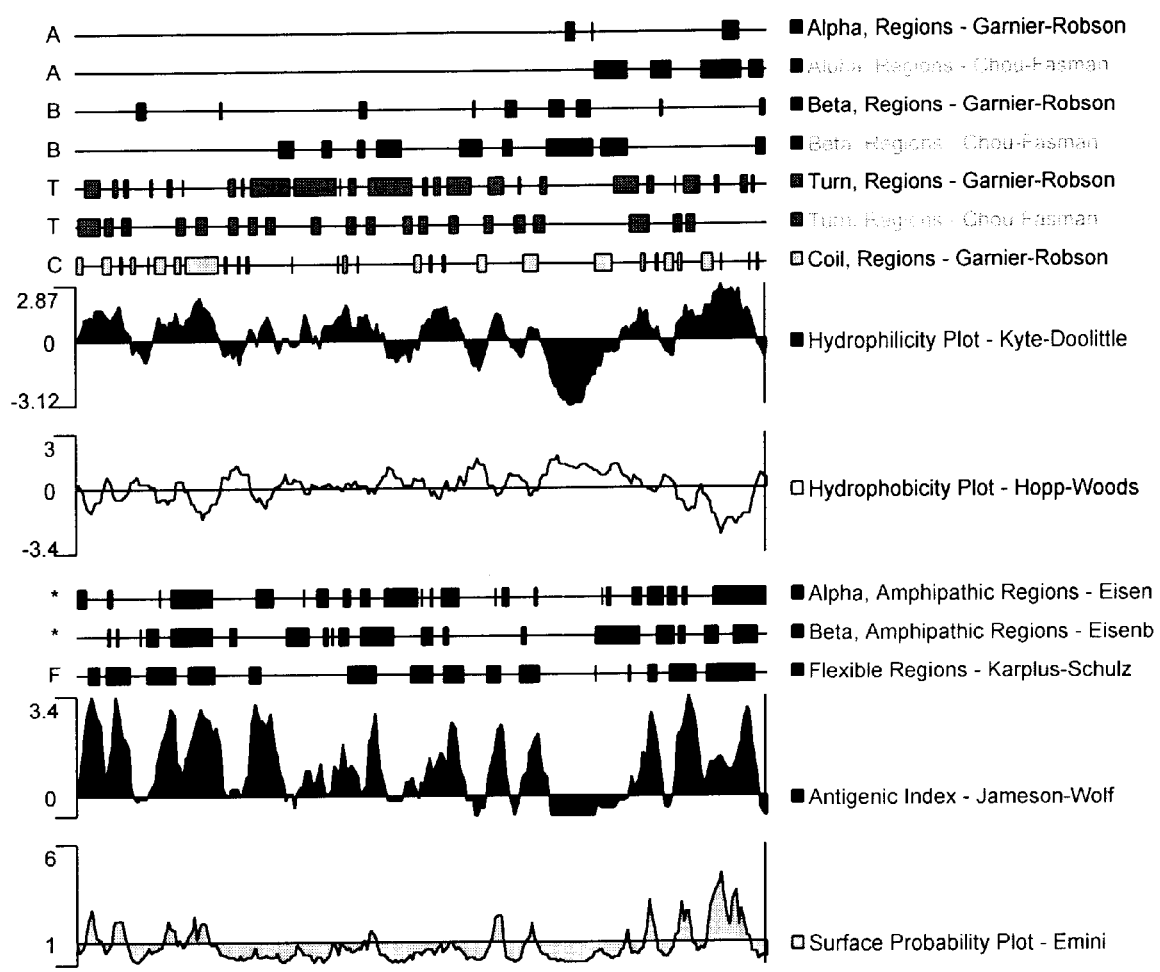
Figure 7:
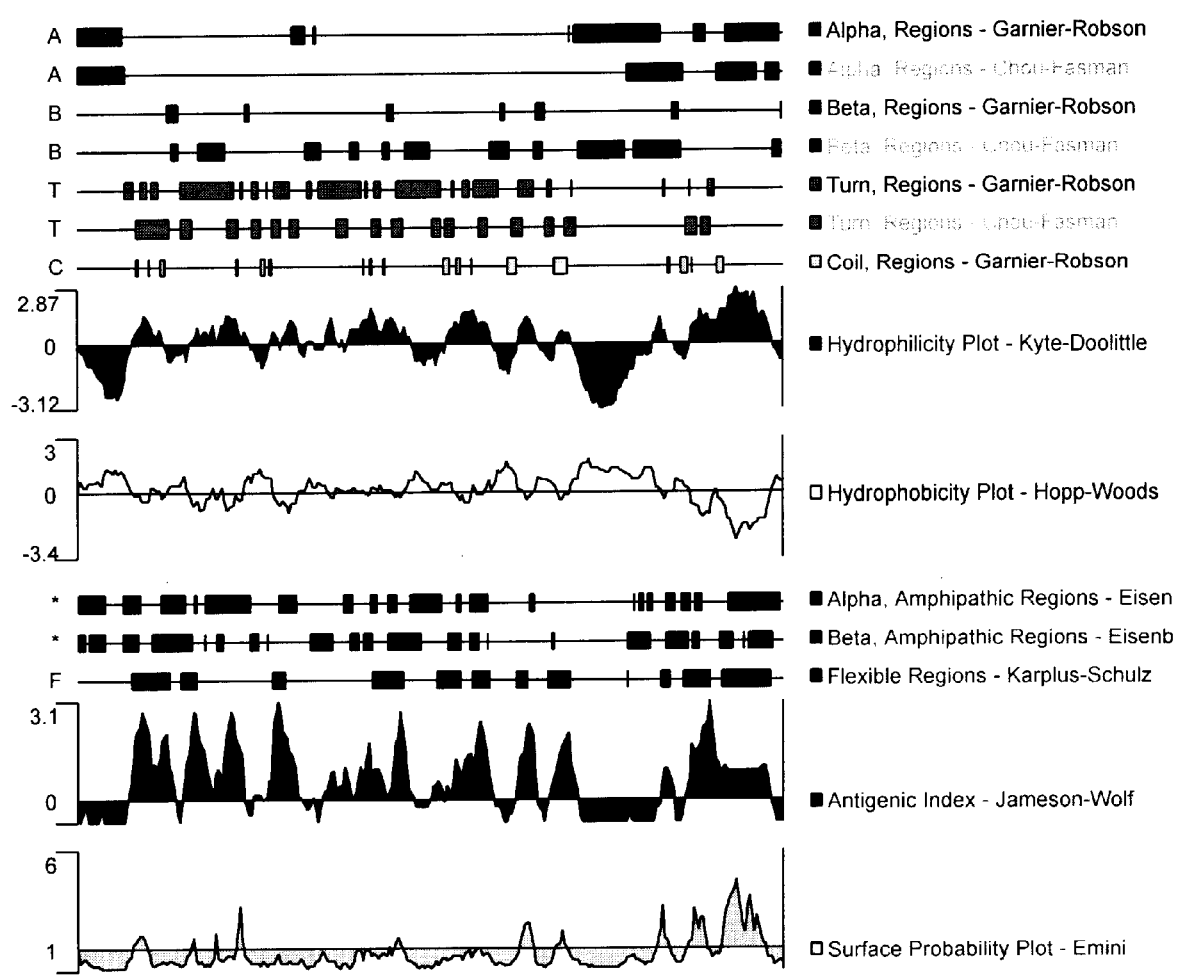

FIGS. 5, 6, and 7 show structural analyses of the TR11, TR11SV1, and TR11SV2 receptor amino acid sequences of FIGS. 1A and 1B, 2A and 2B, and 3A and 3B, respectively. Alpha, beta, turn and coil regions; hydrophilicity and hydrophobicity; amphipathic regions; flexible regions; antigenic index and surface probability are shown.

The DNA*STAR computer program will also represent the identical data presented in FIGS. 5, 6, and 7 in a tabular format. Such a tabular format may assist one practicing one or more aspects of the invention in which specific structural or other features of the invention are delineated according to the data presented in FIGS. 5, 6, and 7 herein. Such structural or other features of the polypeptides of the invention or of polynucleotides encoding such polypeptides which may be identified from the data presented in FIGS. 5, 6, and/or 7, or from tabular representations routinely generated from the identical data using the DNA*STAR computer program set on default settings, include, but are not limited to, Alpha, Regions—Garnier-Robson; Alpha, Regions—Chou-Fasman; Beta, Regions—Garnier-Robson; Beta, Regions—Chou-Fasman; Turn, Regions—Garnier-Robson; Turn, Regions—Chou-Fasman; Coil, Regions—Garnier-Robson; Hydrophilicity Plot—Kyte-Doolittle; Alpha, Amphipathic Regions—Eisenberg; Beta, Amphipathic Regions—Eisenberg; Flexible Regions—Karplus-Schulz; Antigenic Index—Jameson-Wolf; and Surface Probability Plot—Emini. Polynucleotides encoding these structural or other features are preferred embodiments of the present invention.

DETAILED DESCRIPTION OF THE PREFERRED EMBODIMENTS

The present invention provides isolated nucleic acid molecules comprising polynucleotides encoding TR11, TR11SV1, and TR11SV2 polypeptides (FIGS. 1A and 1B, 2A and 2B, and 3A and 3B (SEQ ID NO:2, SEQ ID NO:4, and SEQ ID NO:6, respectively), the amino acid sequences of which were determined by sequencing cloned cDNAs. The TR11, TR11SV1, and TR11SV2 proteins shown in FIGS. 1A and 1B, 2A and 2B, and 3A and 3B, respectively, share sequence homology with the human mGITR receptor-like protein (FIG. 2 (SEQ ID NO:7)). On Oct. 7, 1997, deposits of plasmid DNAs encoding TR11, TR11SV1, and TR11SV2 were made at the American Type Culture Collection (ATCC), 10801 University Boulevard, Manassas, Va. 20110-2209,and given accession numbers 209341, 209343, and 209342 respectively. The nucleotide sequences shown in FIGS. 1A and 1B, 2A and 2B, and 3A and 3B (SEQ ID NO:1, SEQ ID NO:3, and SEQ ID NO:5, respectively) were obtained by sequencing cDNA clones (Clone ID HHEAC71, HCFAZ22, and HT5EA78, respectively) containing the same amino acid coding sequences as the clones in ATCC Accession Nos. 209341, 209343, and 209342 respectively. The deposited clone encoding TR11 is contained in the pCMVSport3.0 plasmid (Life Technologies, Rockville, Md.). The deposited clone encoding TR11SV1 is contained in the pBluescript SK(−) plasmid (Stratagene, La Jolla, Calif.). The deposited clone encoding TR11SV2 is contained in the pSport1 plasmid (Life Technologies, Rockville, Md.).

As used herein, "TR11 protein", "TR11SV1 protein", "TR11SV2 protein", "TR11 receptor", "TR11SV1 receptor", "TR11SV2 receptor", "TR11 receptor protein", "TR11SV1 receptor protein", "TR11SV2 receptor protein", "TR11 polypeptide", "TR11SV1 polypeptide", and "TR11SV2 polypeptide" refer to all proteins resulting from the alternate splicing of the genomic DNA sequences encoding proteins having regions of amino acid sequence identity and receptor activity which correspond to the proteins shown in FIGS. 1A and 1B, 2A and 2B, and 3A and 3B (SEQ ID NO:2, SEQ ID NO:4, and SEQ ID NO:6, respectively). The TR11, TR11SV1, and TR11SV2 proteins shown in FIGS. 1A and 1B, 2A and 2B, and 3A and 3B are examples of such receptor proteins.

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIGS. 1A and 1B, 2A and 2B, and 3A and 3B, nucleic acid molecules of the present invention encoding TR11, TR11SV1, and TR11SV2 polypeptides may be obtained using standard cloning and screening procedures, such as those used for cloning cDNAs using mRNA as starting material. Illustrative of the invention, the nucleic acid molecule described in FIGS. 1A and 1B (SEQ ID NO: 1) was discovered in a cDNA library derived from T-helper cells. A cDNA clone encoding the TR11 polypeptide shown in FIG. 1A was not found in any other cDNA libraries examined. The nucleic acid molecule described in FIGS. 2A and 2B (SEQ ID NO:3) was discovered in a cDNA library derived from T-cells stimulated with PHA for 16 hours. A cDNA clone encoding the TR11SV1 polypeptide shown in FIGS. 2A and 2B was not found in any other cDNA libraries examined. Finally, the nucleic acid molecule described in FIGS. 3A and 3B (SEQ ID NO:5) was discovered in a cDNA library derived from activated T-cells. A cDNA clone encoding the TR11SV2 polypeptide shown in FIGS. 3A and 3B was not found in any other cDNA libraries examined.

The determined nucleotide sequence of the TR11 cDNA of FIGS. 1A and 1B (SEQ ID NO: 1) contains an open reading frame encoding a protein of about 241 amino acid residues, with a single potential predicted leader sequence of about 25 amino acid residues, and a deduced molecular weight of about 25,113 Da. The amino acid sequence of the potential predicted mature TR11 receptor is shown in FIGS. 1A and 1B, from amino acid residue about 26 to residue about 234 (amino acid residues 1 to 209 in SEQ ID NO:2). The TR11 protein shown in FIGS. 1A and 1B (SEQ ID NO:2) is about 58.6% identical and about 74.1% similar to the murine mGITR receptor protein shown in SEQ ID NO:7 (see FIGS. 4A and 4B) using the computer program "Bestfit".

The determined nucleotide sequence of the TR11SV1 cDNA of FIGS. 2A and 2B (SEQ ID NO:3) contains an open reading frame encoding a protein of about 241 amino acid residues, with a deduced molecular weight of about 26,029 Da. The TR11 protein shown in FIGS. 2A and 2B (SEQ ID NO:4) is about 53.1% identical and about 67.5% similar to the murine GITR receptor protein shown in SEQ ID NO:7 (see FIGS. 4A and 4B) using the computer program "Bestfit".

The determined nucleotide sequence of the TR11SV2 cDNA of FIGS. 3A and 3B (SEQ ID NO:5) contains an open reading frame encoding a protein of about 240 amino acid residues, with a single potential predicted leader sequence of about 19 amino acid residues, and a deduced molecular weight of about 25,727 Da. The amino acid sequence of the potential predicted mature TR11SV2 receptor is shown in FIGS. 3A and 3B, from amino acid residue about 20 to residue about 240 (amino acid residues 1 to 221 in SEQ ID NO:6). The TR11SV2 protein shown in FIGS. 3A and 3B (SEQ ID NO:6) is about 58.6% identical and about 74.1% similar to the murine GITR receptor protein shown in SEQ ID NO:7 (see FIGS. 4A and 4B) using the computer program "Bestfit".

GITR is a 228 amino acid type I transmembrane protein characterized by three cysteine pseudorepeats in the extracellular domain and is similar to CD27 and 4-1BB in the intracellular domain. GITR specifically protects T-cell receptor-induced apoptosis, although other apoptotic signals, including Fas triggering, dexamethasone treatment, or UV irradiation, do not. Thus, GITR is a new member of tumor necrosis factor/nerve growth factor receptor family and appears to be involved in the regulation of T-cell receptor-mediated cell death (Nocentini G, et al., *Proc. Natl. Acad. Sci. USA* 94:6216–6221 (1997)). Based on the high degree of conservation with murine GITR at the amino acid level, it is likely that TR11, TR11SV1, and TR11SV2 may also be involved in the regulation of cell-type specific receptor-mediated cell growth, differentiation, and, ultimately, cell death.

As indicated, the present invention also provides mature forms of the TR11 and TR11SV2 receptors of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides nucleotide sequences encoding mature TR11 and TR11SV2 polypeptides having the amino acid sequences encoded by the cDNA clones contained in ATCC Deposit Numbers 209341 and 209342 and as shown in FIGS. 1A and 1B and 3A and 3B, respectively (SEQ ID NO:2 and SEQ ID NO:6, respectively). By the mature TR11 and TR11SV2 polypeptides having the amino acid sequences encoded by "the cDNA clones contained in ATCC Deposit Numbers 209341 and 209342 is meant the mature form(s) of the TR11 and TR11SV2 receptors produced by expression in a mammalian cell (e.g., COS cells, as described below) of the complete open reading frame encoded by the human DNA sequence of the deposited clones.

Methods for predicting whether a protein has a secretory leader as well as the cleavage point for that leader sequence are available. For instance, the methods of McGeoch (*Virus Res.* 3:271–286 (1985)) and von Heinje (*Nucleic Acids Res.* 14:4683–4690 (1986)) can be used. The accuracy of predicting the cleavage points of known mammalian secretory proteins for each of these methods is in the range of 75–80% (von Heinje, supra). However, the two methods do not always produce the same predicted cleavage point(s) for a given protein.

In the present case, the predicted amino acid sequences of the complete TR11, TR11SV1, and TR11SV2 polypeptides shown in FIGS. 1A and 1B, 2A and 2B, and 3A and 3B (SEQ ID NO:2, SEQ ID NO:4, and SEQ ID NO:6) were analyzed by a computer program ("PSORT") (K. Nakai and M. Kanehisa, *Genomics* 14:897–911 (1992)), which is an expert system for predicting the cellular location of a protein based on the amino acid sequence. As part of this computational prediction of localization, the methods of McGeoch and von Heinje are incorporated. The analysis by the PSORT program predicted a signal peptide cleavage site between amino acids 25 and 26 in FIGS. 1A and 1B (−1 and +1 in SEQ ID NO:2). Thus, the potential leader sequence for the TR11 protein shown in SEQ ID NO:2 is predicted to consist of amino acid residues −25 to −1 in SEQ ID NO:2, while the predicted mature TR11 protein consists of amino acid residues 1 to 209 for the TR11 protein shown in SEQ ID NO:2. Further, the analysis by the PSORT program predicted no signal peptide cleavage sites for the TR11SV1 protein shown in SEQ ID NO:4. Finally, the analysis by the PSORT program predicted a single signal peptide cleavage site between amino acids 19 and 20 in FIGS. 3A and 3B (−1 and +1 in SEQ ID NO:6). Thus, the potential leader sequence for the TR11SV2 protein shown in SEQ ID NO:6 is predicted to consist of amino acid residues −19 to −1 in SEQ ID NO:6, while the predicted mature TR11SV2 protein consists of amino acid residues 1 to 221 for the TR11SV2 protein shown in SEQ ID NO:6.

As one of ordinary skill would appreciate, however, due to the possibilities of sequencing errors, as well as the variability of cleavage sites for leaders in different known proteins, the TR11, TR11SV1, and TR11SV2 receptor polypeptides encoded by the cDNAs of ATCC Deposit Numbers 209341, 209343, and 209342 respectively, comprise about 241 amino acids (but may be anywhere in the range of 224 to 251 amino acids), about 241 amino acids (but may be anywhere in the range of 231 to 251 amino acids), and about 240 amino acids (but may be anywhere in the range of 230 to 250 amino acids). Further, the predicted leader sequences of these proteins are about 25, 0, and 19 amino acids, but the actual leaders may be anywhere in the range of about 15 to about 35, about 20 to about 40, and about 9 to about 29 amino acids, respectively.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) shown in FIGS. 1A and 1B (SEQ ID NO:1); DNA molecules comprising the coding sequence for the mature TR11 receptor shown in FIGS. 1A and 1B (SEQ ID NO:2; about the last 209 amino acids); and DNA molecules which comprise a sequence substantially different from those described above but which, due to the degeneracy of the genetic code, still encode the TR11 receptor protein shown in FIG. 1A (SEQ ID NO:2). Isolated nucleic acid molecules of the present invention include DNA molecules comprising an open reading frame (ORF) shown in FIGS. 2A and 2B (SEQ ID NO:3); DNA molecules comprising the coding sequence for the mature TR11SV1 receptor shown in FIGS. 2A and 2B (SEQ ID NO:4; about the last 241 amino acids); and DNA molecules which comprise a sequence substantially different from those described above but which, due to the degeneracy of the genetic code, still encode the TR11SV1 receptor protein shown in FIGS. 2A and 2B (SEQ ID NO:4). Isolated nucleic acid molecules of the present invention include DNA molecules comprising an open reading frame (ORF) shown in FIGS. 3A and 3B (SEQ ID NO:5); DNA molecules comprising the coding sequence for the mature TR11SV2 receptor shown in FIGS. 3A and 3B (SEQ ID NO:6; about the last 221 amino acids); and DNA molecules which comprise a sequence substantially different from those described above but which, due to the degeneracy of the genetic code, still encode the TR11SV2 receptor protein shown in FIGS. 3A and 3B (SEQ ID NO:6). Of course, the genetic code is well known in the art. Thus, it would be routine for one skilled in the art to generate such degenerate variants.

In another aspect, the invention provides isolated nucleic acid molecules encoding the TR11, TR11SV1, and TR11SV2 polypeptides having the amino acid sequence encoded by the cDNA clones contained in the plasmids deposited as ATCC Deposit Nos. 209341, 209343, and 209342, respectively, on Oct. 7, 1997. In a further embodiment, these nucleic acid molecules will encode a mature polypeptide or the full-length polypeptide lacking the N-terminal methionine. The invention further provides isolated nucleic acid molecules having the nucleotide sequences shown in FIGS. 1A and 1B (SEQ ID NO:1), 2A and 2B (SEQ ID NO:3), and 3A and 3B (SEQ ID NO:5), the nucleotide sequences of the cDNAs contained in the above-described deposited clones; or nucleic acid molecules having a sequence complementary to one of the above sequences. Such isolated molecules, particularly DNA molecules, are useful as probes for gene mapping, by in situ hybridization with chromosomes, and for detecting expression of the TR11, TR11SV1, and TR11SV2 receptor genes of the present invention in human tissue, for instance, by Northern blot analysis.

In addition, the invention provides nucleic acid molecules having nucleotide sequences related to extensive portions of SEQ ID NO:1, SEQ ID NO:3, and SEQ ID NO:5 which have been determined from the following related cDNA clones: HHEAC71RA (SEQ ID NO:8) and HCFAZ22R (SEQ ID NO:9).

The present invention is further directed to fragments of the isolated nucleic acid molecules described herein. By a fragment of an isolated nucleic acid molecule having the nucleotide sequence of the deposited cDNA or the nucleotide sequences shown in FIGS. 1A and 1B, 2A and 2B, and 3A and 3B (SEQ ID NO:1, SEQ ID NO:3, and SEQ ID NO:5, respectively) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–400 nt in length are also useful according to the present invention as are fragments corresponding to most, if not all, of the nucleotide sequences of the deposited cDNAs or as shown in FIGS. 1A and 1B, 2A and 2B, and 3A and 3B (SEQ ID NO:1, SEQ ID NO:3, and SEQ ID NO:5, respectively). By a fragment at least 20 nt in length, for example, is intended fragments which include 20 or more contiguous bases from the nucleotide sequences of the deposited cDNAs or the nucleotide sequence as shown in FIGS. 1A and 1B, 2A and 2B, and 3A and 3B (SEQ ID NO:1, SEQ ID NO:3, and SEQ ID NO:5, respectively). Further, the present invention is also directed to an isolated fragment of a nucleic acid molecule, comprising a polynucleotide having a sequence shown in FIGS. 1A and 1B, 2A and 2B, and 3A and 3B (SEQ ID NO:1, SEQ ID NO:3, and SEQ ID NO:5, respectively), or any sequence complementary to those shown in FIGS. 1A and 1B, 2A and 2B, and 3A and 3B (SEQ ID NO:1, SEQ ID NO:3, and SEQ ID NO:5, respectively), wherein said fragment comprises at least 30 to 50 contiguous nucleotides from SEQ ID NO:1, SEQ ID NO:3 or SEQ ID NO:5, provided that said isolated nucleic acid molecule is not SEQ ID NO:8, SEQ ID NO:9 or any subfragment thereof.

Preferred nucleic acid fragments of the present invention include nucleic acid molecules encoding: a polypeptide comprising the TR11 receptor protein of FIGS. 1A and 1B (SEQ ID NO:2) extracellular domain (predicted to constitute amino acid residues from about 26 to about 162 in FIGS. 1A and 1B (amino acid residues 1 to 137 in SEQ ID NO:2)); a polypeptide comprising the TR11SV1 receptor protein of FIGS. 2A and 2B (SEQ ID NO:4) extracellular domain (predicted to constitute amino acid residues from about 1 to about 162 in FIGS. 2A and 2B (amino acid residues 1 to 162 in SEQ ID NO:4)); a polypeptide comprising the TR11SV2 receptor protein of FIGS. 3A and 3B (SEQ ID NO:6) extracellular domain (predicted to constitute amino acid residues from about 20 to about 168 in FIGS. 3A and 3B (amino acid residues 1 to 149 in SEQ ID NO:6)); a polypeptide comprising the TR11 receptor transmembrane domain (amino acid residues 163 to 179 in FIGS. 1A and 1B (amino acid residues 138 to 154 in SEQ ID NO:2)); a polypeptide comprising the TR11SV1 receptor transmembrane domain (amino acid residues 163 to 179 in FIGS. 2A and 2B (amino acid residues 163 to 179 in SEQ ID NO:4)); a polypeptide comprising the TR11SV2 receptor transmembrane domain (amino acid residues 169 to 185 in FIGS. 3A and 3B (amino acid residues 150 to 166 in SEQ ID NO:6)); a polypeptide comprising the TR11 receptor intracellular domain (predicted to constitute amino acid residues from about 180 to about 234 in FIGS. 1A and 1B (amino acid residues 155 to 209 in SEQ ID NO:2)); a polypeptide comprising the TR11SV1 receptor intracellular domain (predicted to constitute amino acid residues from about 180 to about 241 in FIGS. 2A and 2B (amino acid residues 180 to 241 in SEQ ID NO:4)); a polypeptide comprising the TR11SV2 receptor intracellular domain (predicted to constitute amino acid residues from about 186 to about 240 in FIGS. 3A and 3B (amino acid residues 167 to 221 in SEQ ID NO:6)); a polypeptide comprising the TR11 receptor protein of FIGS. 1A and 1B (SEQ ID NO:2) extracellular and intracellular domains with all or part of the transmembrane domain deleted; a polypeptide comprising the TR11SV1 receptor protein of FIGS. 2A and 2B (SEQ ID NO:4) extracellular and intracellular domains with all or part of the transmembrane domain deleted; and a polypeptide comprising the TR11SV2 receptor protein of FIGS. 3A and 3B (SEQ ID NO:6) extracellular and intracellular domains with all or part of the transmembrane domain deleted.

As above with the leader sequence, the amino acid residues constituting the extracellular, transmembrane and intracellular domains have been predicted by computer analysis. Thus, as one of ordinary skill would appreciate, the amino acid residues constituting these domains may vary slightly (e.g., by about 1 to about 15 amino acid residues) depending on the criteria used to define each domain.

Preferred nucleic acid fragments of the present invention also include nucleic acid molecules encoding epitope-bearing portions of the TR11 receptor proteins. In particular, such nucleic acid fragments of the present invention include nucleic acid molecules encoding: a polypeptide comprising amino acid residues from about Arg-2 to about Gly-11 in SEQ ID NO:2; a polypeptide comprising amino acid residues from about Thr-18 to about Arg-26 in SEQ ID NO:2; a polypeptide comprising amino acid residues from about Arg-34 to about Cys-42 in SEQ ID NO:2; a polypeptide comprising amino acid residues from about Arg-31 to about Glu-39 in SEQ ID NO:2; a polypeptide comprising amino acid residues from about Gly-38 to about Asp-46 in SEQ ID NO:2; a polypeptide comprising amino acid residues from about Gly-74 to about Ser-82 in SEQ ID NO:2; a polypeptide comprising amino acid residues from about Glu-100 to about Asp-108 in SEQ ID NO:2; a polypeptide comprising amino acid residues from about Phe-118 to about Ala-126 in SEQ ID NO:2; a polypeptide comprising amino acid residues from about Gly-131 to about Gly-139 in SEQ ID NO:2; a polypeptide comprising amino acid residues from about Pro-178 to about Cys-186 in SEQ ID NO:2; and a polypeptide comprising amino acid residues from about Ser-197 to about Gly-205 in SEQ ID NO:2. The inventors have determined that the above polypeptide fragments are antigenic regions of the TR11 receptors. Methods for determining other such epitope-bearing portions of the TR11 proteins are described in detail below.

Preferred nucleic acid fragments of the present invention further include nucleic acid molecules encoding epitope-bearing portions of the TR11SV1 receptor proteins. In particular, such nucleic acid fragments of the present invention include nucleic acid molecules encoding: a polypeptide comprising amino acid residues from about Ala-2 to about Ile-10 in SEQ ID NO:4; a polypeptide comprising amino acid residues from about Asn-11 to about Gly-19 in SEQ ID NO:4; a polypeptide comprising amino acid residues from about Thr-27 to about Ser-35 in SEQ ID NO:4; a polypeptide comprising amino acid residues from about Trp-38 to about Glu-46 in SEQ ID NO:4; a polypeptide comprising amino acid residues from about Gly-42 to about Ser-50 in SEQ ID NO:4; a polypeptide comprising amino acid residues from about Glu-31 to about Glu-46 in SEQ ID NO:4; a polypeptide comprising amino acid residues from about Cys-61 to about Glu-69 in SEQ ID NO:4; a polypeptide comprising amino acid residues from about Gly-99 to about Ser-107 in SEQ ID NO:4; a polypeptide comprising amino acid residues from about Glu-125 to about Asp-133 in SEQ ID NO:4; a polypeptide comprising amino acid residues from about Phe-143 to about Ala-151 in SEQ ID NO:4; a polypeptide comprising amino acid residues from about Gly-156 to about Gly-164 in SEQ ID NO:4; a polypeptide comprising amino acid residues from about Cys-196 to about Leu-204 in SEQ ID NO:4; a polypeptide comprising amino acid residues from about Pro-209 to about Ser-217 in SEQ ID NO:4; and a polypeptide comprising amino acid residues from about Ser-229 to about Gly-237 in SEQ ID NO:4. The inventors have determined that the above polypeptide fragments are antigenic regions of the TR11SV1 receptors. Methods for determining other such epitope-bearing portions of the TR11SV1 proteins are described in detail below.

Preferred nucleic acid fragments of the present invention also include nucleic acid molecules encoding epitope-bearing portions of the TR11SV2 receptor proteins. In particular, such nucleic acid fragments of the present invention include nucleic acid molecules encoding: a polypeptide comprising amino acid residues from about Gln-1 to about Cys-9 in SEQ ID NO:6; a polypeptide comprising amino acid residues from about Gly-5 to about Arg-13 in SEQ ID NO:6; a polypeptide comprising amino acid residues from about Thr-18 to about Arg-26 in SEQ ID NO:6; a polypeptide comprising amino acid residues from about Thr-29 to about Pro-37 in SEQ ID NO:6; a polypeptide comprising amino acid residues from about Cys-48 to about Glu-56 in SEQ ID NO:6; a polypeptide comprising amino acid residues from about Val-87 to about Phe-95 in SEQ ID NO:6; a polypeptide comprising amino acid residues from about His-111 to about Thr-119 in SEQ ID NO:6; a polypeptide comprising amino acid residues from about Phe-130 to about Ala-138 in SEQ ID NO:6; a polypeptide comprising amino acid residues from about Gly-143 to about Gly-151 in SEQ ID NO:6; a polypeptide comprising amino acid residues from about Pro-190 to about Cys-198 in SEQ ID NO:6; and a polypeptide comprising amino acid residues from about Ser-209 to about Gly-217 in SEQ ID NO:6. The inventors have determined that the above polypeptide fragments are antigenic regions of the TR11SV2 receptors. Methods for determining other such epitope-bearing portions of the TR11SV2 proteins are described in detail below.

In another aspect, the invention provides isolated nucleic acid molecules comprising polynucleotides which hybridizes under stringent hybridization conditions to a portion of the polynucleotide of one of the nucleic acid molecules of the invention described above, for instance, the cDNA clones contained in ATCC Deposit Nos. 209341, 209343, and 209342 respectively. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate; and 20 $\mu$g/ml idenatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

By a portion of a polynucleotide of "at least 20 nt in length, " for example, is intended 20 or more contiguous nucleotides from the nucleotide sequence of the reference polynucleotide (e.g., the deposited cDNAs or the nucleotide sequences as shown in FIGS. 1A and 1B, 2A and 2B, and 3A and 3B (SEQ ID NO:1, SEQ ID NO:3, and SEQ ID NO:5, respectively).

Of course, a polynucleotide which hybridizes only to a poly A sequence (such as the 3' terminal poly(A) tract of a cDNA sequence), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode TR11, TR11SV1 or TR11SV2 polypeptides may include, but are not limited to those encoding the amino acid sequences of the mature polypeptides, by themselves; the coding sequences for the mature polypeptides and additional sequences, such as those encoding the potential leader or signal peptide sequences, such as pre-, or pro- or prepro-protein sequences; the coding sequences of the mature polypeptides, with or without the aforementioned additional coding sequences, together with additional, non-coding sequences, including for example, but not limited to, introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequences encoding the polypeptides may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described by Gentz and colleagues (*Proc. Natl. Acad. Sci. USA* 86:821–824 (1989)), for instance, hexa-histidine provides for convenient purification of the fusion protein. The "HA" tag is another peptide useful for purification which corresponds to an epitope derived from the influenza hemagglutinin protein, which has been described by Wilson and coworkers (*Cell* 37:767 (1984)). As discussed below, other such fusion proteins include the TR11 receptors fused to IgG-Fc at the N- or C-terminus.

The present invention further relates to variants of the nucleic acid molecules of the present invention, which encode portions, analogs or derivatives of the TR11, TR11SV1, and TR11SV2 receptors. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the TR11, TR11SV1, and TR11SV2 receptors or portions thereof. Also especially preferred in this regard are conservative substitutions.

Further embodiments of the invention include isolated nucleic acid molecules comprising a polynucleotide having a nucleotide sequence at least 90% identical, and more preferably at least 95%, 96%, 97%, 98% or 99% identical to: (a) a nucleotide sequence encoding the TR11 polypeptide having the complete amino acid sequence shown in FIGS. 1A and 1B (amino acid residues −25 to 209 in SEQ ID NO:2); (b) a nucleotide sequence encoding the TR11SV1 polypeptide having the complete amino acid sequence shown in FIGS. 2A and 2B (amino acid residues 1 to 241 in SEQ ID NO:4); (c) a nucleotide sequence encoding the TR11SV2 polypeptide having the complete amino acid sequence shown in FIGS. 3A and 3B (amino acid residues −19 to 221 in SEQ ID NO:6); (d) a nucleotide encoding the complete amino sequence shown in FIGS. 1A and 1B but lacking the N-terminal methionine (i.e., amino acids −24 to 209 in SEQ ID NO:2); (e) a nucleotide encoding the complete amino sequence shown in FIGS. 2A and 2B but lacking the N-terminal methionine i.e., amino acids 2 to 241 in SEQ ID NO:4); (f) a nucleotide encoding the complete amino sequence shown in FIGS. 3A and 3B but lacking the N-terminal methionine (i.e., amino acids −18 to 221 in SEQ ID NO:6); (g) a nucleotide sequence encoding the predicted mature TR11 receptor comprising the amino acid sequence at positions from 26 to 234 in FIGS. 1A and 1B (amino acid residues 1 to 209 in SEQ ID NO:2); (h) a nucleotide sequence encoding the predicted mature TR11SV1 receptor comprising the amino acid sequence at positions from 1 to 241 in FIGS. 2A and 2B (amino acid residues 1 to 241 in SEQ ID NO:4); (i) a nucleotide sequence encoding the predicted mature TR11SV2 receptor comprising the amino acid sequence at positions from 20 to 240 in FIGS. 3A and 3B (amino acid residues 1 to 221 in SEQ ID NO:6); (j) a nucleotide sequence encoding the TR11 polypeptide having the complete amino acid sequence including the leader encoded by the cDNA clone contained in ATCC Deposit Number 209341; (k) a nucleotide sequence encoding the TR11SV1 polypeptide having the complete amino acid sequence including the leader encoded by the cDNA clone contained in ATCC Deposit Number 209343; (l) a nucleotide sequence encoding the TR11SV2 polypeptide having the complete amino acid sequence including the leader encoded by the cDNA clone contained in ATCC Deposit Number 209342; (m) a nucleotide sequence encoding the mature TR11 receptor having the amino acid sequences encoded by the cDNA clone contained in ATCC Deposit Number 209341; (n) a nucleotide sequence encoding the mature TR11SV1 receptor having the amino acid sequences encoded by the cDNA clone contained in ATCC Deposit Number 209343; (o) a nucleotide sequence encoding the mature TR11SV2 receptor having the amino acid sequences encoded by the cDNA clone contained in ATCC Deposit Number 209342; (p) a nucleotide sequence encoding the TR11 receptor extracellular domain; (q) a nucleotide sequence encoding the TR11SV1 receptor extracellular domain; (r) a nucleotide sequence encoding the TR11SV2 receptor extracellular domain; (s) a nucleotide sequence encoding the TR11 receptor transmembrane domain; (t) a nucleotide sequence encoding the TR11SV1 receptor transmembrane domain; (u) a nucleotide sequence encoding the TR11SV2 receptor transmembrane domain; (v) a nucleotide sequence encoding the TR11 receptor intracellular domain; (w) a nucleotide sequence encoding the TR11SV1 receptor intracellular domain; (x) a nucleotide sequence encoding the TR11SV2 receptor intracellular domain; (y) a nucleotide sequence encoding the TR11 receptor extracellular and intracellular domains with all or part of the transmembrane domain deleted; (z) a nucleotide sequence encoding the TR11SV1 receptor extracellular and intracellular domains with all or part of the transmembrane domain deleted; (aa) a nucleotide sequence encoding the TR11SV2 receptor extracellular and intracellular domains with all or part of the transmembrane domain deleted; and (bb) a nucleotide sequence complementary to any of the nucleotide sequences in (a), (b), (c), (d), (e), (f), (g), (h), (i), (j), (k), (l), (m), (n), (o), (p), (q), (r), (s), (t), (u), (v), (w), (x), (y), (z) or (aa).

A further nucleic acid embodiment of the invention relates to an isolated nucleic acid molecule comprising a polynucleotide which encodes the amino acid sequence of a TR11, TR11SV1 and/or TR11SV2 polypeptide having an amino acid sequence which contains at least one conservative amino acid substitution, but not more than 50 conservative amino acid substitutions, even more preferably, not more than 40 conservative amino acid substitutions, still more preferably not more than 30 conservative amino acid substitutions, and still even more preferably not more than 20 conservative amino acid substitutions. Of course, in order of ever-increasing preference, it is highly preferable for a polynucleotide which encodes the amino acid sequence of a TR11, TR11SV1 or TR11SV2 polypeptide to have an amino acid sequence which contains not more than 7–10, 5–10, 3–7, 3–5, 2–5, 1–5, 1–3, 10, 9, 8, 7, 6, 5, 4, 3, 2 or 1 conservative amino acid substitutions.

The present invention also relates to recombinant vectors, which include the isolated nucleic acid molecules of the present invention, and to host cells containing the recombinant vectors, as well as to methods of making such vectors and host cells and for using them for production of TR11, TR11SV1 or TR11SV2 polypeptides or peptides by recombinant techniques.

By a polynucleotide having a nucleotide sequence at least, for example, 95% "identical" to a reference nucleotide sequence encoding a TR11, TR11SV1 or TR11SV2 polypeptide is intended that the nucleotide sequence of the polynucleotide is identical to the reference sequence except that the polynucleotide sequence may include up to five point mutations per each 100 nucleotides of the reference nucleotide sequence encoding the TR11, TR11SV1 or TR11SV2 receptors. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIGS. 1A and 1B, 2A and 2B, and/or 3A and 3B, or to the nucleotides sequence of the deposited cDNA clones can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman to find the best segment of homology between two sequences (*Advances in Applied Mathematics* 2:482–489 (1981)). When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed. A preferred method for determining the best overall match between a query sequence (a sequence of the present invention) and a subject sequence, also referred to as a global sequence alignment, can be determined using the FASTDB computer program based on the algorithm of Brutlag and colleagues (*Comp. App. Biosci.* 6:237–245 (1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identiy are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignement of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

The present application is directed to nucleic acid molecules at least 90%, 95%, 96%, 97%, 98% or 99% identical to the nucleic acid sequences shown in FIGS. 1A and 1B, 2A and 2B, and 3A and 3B (SEQ ID NO:1, SEQ ID NO:3, and SEQ ID NO:5, respectively) or to the nucleic acid sequence of the deposited cDNAs, irrespective of whether they encode a polypeptide having TR11, TR11SV1 or TR11SV2 receptor activity. This is because even where a particular nucleic acid molecule does not encode a polypeptide having TR11, TR11SV1 or TR11SV2 receptor activity, one of skill in the art would still know how to use the nucleic acid molecule, for instance, as a hybridization probe or a polymerase chain reaction (PCR) primer. Uses of the nucleic acid molecules of the present invention that do not encode a polypeptide having TR11, TR11SV1 or TR11SV2 receptor activity include, inter alia, (1) isolating a TR11, TR11SV1 or TR11SV2 receptor gene or allelic or splice variants thereof in a cDNA library; (2) in situ hybridization (e.g., "FISH") to metaphase chromosomal spreads to provide precise chromosomal location of a TR11, TR11SV1 or TR11SV2 receptor gene, as described by Verma and colleagues (*Human Chromosomes: A Manual of Basic Techniques*, Pergamon Press, New York (1988)); and (3) Northern Blot analysis for detecting TR11, TR11SV1 or TR11SV2 receptor mRNA expression in specific tissues.

Preferred, however, are nucleic acid molecules having sequences at least 90%, 95%, 96%, 97%, 98% or 99% identical to the nucleic acid sequences shown in FIGS. 1A and 1B, 2A and 2B, and 3A and 3B (SEQ ID NO:1, SEQ ID NO:3, and SEQ ID NO:5, respectively) or to the nucleic acid sequence of the deposited cDNAs which do, in fact, encode a polypeptide having TR11, TR11SV1, and TR11SV2 receptor activity, respectively. By "a polypeptide having TR11, TR11SV1, and TR11SV2 receptor activity" is intended polypeptides exhibiting activity similar, but not necessarily identical, to an activity of the TR11, TR11SV1, and TR11SV2 receptors of the present invention (either the full-length protein, the splice variants, or, preferably, the mature protein), as measured in a particular biological assay. For example, TR11, TR11SV1, and TR11SV2 receptor activities can be measured by determining the ability of a TR11, TR11SV1, or TR11SV2 polypeptide-Fc fusion protein to inhibit lymphocyte proliferation. TR11, TR11SV1, and TR11SV2 receptor activities may also be measured by determining the ability of a polypeptide, such as cognate ligand which is free or expressed on a cell surface, to confer proliferatory activity in intact cells expressing one or more of the receptors.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequences of the deposited cDNAs or the nucleic acid sequence shown in FIGS. 1A and 1B, 2A and 2B, and 3A and 3B (SEQ ID NO:1, SEQ ID NO:3, and SEQ ID NO:5, respectively) will encode polypeptides "having TR11, TR11SV1 or TR11SV2 receptor activity." In fact, since degenerate variants of any of these nucleotide sequences all encode the same polypeptide, this will be clear to the skilled artisan even without performing the above described comparison assays. It will be further recognized in the art that, for such nucleic acid molecules that are not degenerate variants, a reasonable number will also encode a polypeptide having TR11, TR11SV1 or TR11SV2 protein activities. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided by Bowie and colleagues ("Deciphering the Message in Protein Sequences: Tolerance to Amino Acid Substitutions," *Science* 247:1306–1310 (1990)), wherein the authors indicate that proteins are surprisingly tolerant of amino acid substitutions.

Vectors and Host Cells

The present invention also relates to vectors which include the isolated DNA molecules of the present invention, host cells which are genetically engineered with the recombinant vectors, and the production of TR11, TR11SV1, and TR11SV2 polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate heterologous hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

Among vectors preferred for use in bacteria include pHE4, pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, human hIL-5 receptor has been fused with Fc portions for the purpose of high-throughput screening assays to identify antagonists of hIL-5. See, D. Bennett et al., *Journal of Molecular Recognition*, Vol. 8:52–58 (1995) and K. Johanson et al., *The Journal of Biological Chemistry*, Vol. 270, No. 16:9459–9471 (1995).

TR11, TR11SV1 and TR11SV2 receptors can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

TR11, TR11SV1, and TR11SV2 Polypeptides and Fragments

Representative examples of TR11 polynucleotide fragments include, for example, fragments having a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950 of 951 to the end of SEQ ID NO:1 or the cDNA contained in the deposited clone. Representative examples of TR11SV1 polynucleotide fragments include, for example, fragments having a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1007 or 951 to the end of SEQ ID NO:3 or the cDNA contained in the deposited clone. Representative examples of TR11SV2 polynucleotide fragments include, for example, fragments having a sequence from about nucleotide number 1–50, 51–100, 101–150, 151–200, 201–250, 251–300, 301–350, 351–400, 401–450, 451–500, 501–550, 551–600, 651–700, 701–750 751–800, 800–850, 851–900, 901–950, 951–1000, 1001–1050, 1051 to the end of SEQ ID NO:5 or the cDNA contained in the deposited clone. In this context "about" includes the particularly recited ranges, larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein.

In the present invention, a "polypeptide fragment" refers to a short amino acid sequence contained in SEQ ID NO:2, SEQ ID NO:4, SEQ ID NO:6 or encoded by the cDNA contained in the deposited clones. Protein fragments may be "free-standing," or comprised within a larger polypeptide of which the fragment forms a part or region, most preferably as a single continuous region. Representative examples of polypeptide fragments of the invention, include, for example, fragments from about amino acid number 1–20, 21–40, 41–60, 61–80, 81–100, 102–120, 121–140, 141–160, 161–180, 181–200, 201–220, 221 to the end of the coding region of SEQ ID NO:2; 1–20, 21–40, 41–60, 61–80, 81–100, 102–120, 121–140, 141–160, 161–180, 181–200, 201–220, 221 to the end of the coding region of SEQ ID NO:4; or 1–20, 21–40, 41–60, 61–80, 81–100, 102–120, 121–140, 141–160, 161–180, 181–200, 201–220, 221 to the end of the coding region of SEQ ID NO:6. Moreover, polypeptide fragments can be about 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

However, many polynucleotide sequences, such as EST sequences, are publicly available and accessible through sequence databases. Some of these sequences are related to SEQ ID NO:1, SEQ ID NO:3 and/or SEQ ID NO:5 and may have been publicly available prior to conception of the present invention. Preferably, such related polynucleotides are specifically excluded from the scope of the present invention. To list every related sequence would be cumbersome. Similarly, preferably excluded from the present invention are one or more polynucleotides comprising a nucleotide sequence described by the general formula of $a^1-b^1$, where $a^1$ is any integer between 1 to 969 of SEQ ID NO:1, $b^1$ is an integer of 15 to 983, where both $a^1$ and $b^1$ correspond to the positions of nucleotide residues shown in SEQ ID NO:1, and where the $b^1$ is greater than or equal to $a^1+14$. Similarly, preferably excluded from the present invention are one or more polynucleotides comprising a nucleotide sequence described by the general formula of $a^2-b^2$, where $a^2$ is any integer between 1 to 993 of SEQ ID NO:3, $b^2$ is an integer of 15 to 1007, where both $a^2$ and $b^2$ correspond to the positions of nucleotide residues shown in SEQ ID NO:3, and where the $b^2$ is greater than or equal to $a^2+14$. Accordingly, preferably excluded from the present invention are one or more polynucleotides comprising a nucleotide sequence described by the general formula of $a^3-b^3$, where $a^3$ is any integer between 1 to 1060 of SEQ ID NO:5, $b^3$ is an integer of 15 to 1074, where both $a^3$ and $b^3$ correspond to the positions of nucleotide residues shown in SEQ ID NO:5, and where the $b^3$ is greater than or equal to $a^3+14$.

In specific embodiments, the polynucleotides of the invention are less than 300 kb, 200 kb, 100 kb, 50 kb, 15 kb, 10 kb, or 7.5 kb in length. In a further embodiment, polynucleotides of the invention comprise at least 15 contiguous nucleotides of TR11, TR11SV1, or TR11SV2 coding sequence, but do not comprise all or a portion of any TR11, TR11SV1, or TR11SV2 intron. In another embodiment, the nucleic acid comprising TR11, TR11SV1, or TR11SV2 coding sequence does not contain coding sequences of a genomic flanking gene (i.e., 5' or 3' to the TR11, TR11SV1, or TR11SV2 gene in the genome).

The invention further provides isolated TR11, TR11SV1, and TR11SV2 polypeptides having the amino acid sequence encoded by the deposited cDNAs, or the amino acid sequences in FIGS. 1A and 1B, 2A and 2B, and 3A and 3B (SEQ ID NO:2, SEQ ID NO:4, and SEQ ID NO:6, respectively) or a peptide or polypeptide comprising a portion of the above polypeptides.

To improve or alter the characteristics of TR11, TR11SV1, and/or TR11SV2 polypeptides, protein engineering may be employed. Recombinant DNA technology known to those skilled in the art can be used to create novel mutant proteins or muteins, including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron and colleagues (*J. Biol. Chem.*, 268:2984–2988 (1993)) reported modified KGF proteins that had heparin binding activity even if 3, 8, or 27 N-terminal amino acid residues were missing. Similarly, many examples of biologically functional C-terminal deletion muteins are known. For instance, Interferon gamma shows up to ten times higher activities by deleting 8–10 amino acid residues from the carboxy terminus of the protein (Dobeli, et al., *J. Biotechnology* 7:199–216 (1988)).

Thus, even if deletion of one or more amino acids from the N-terminus of a protein results in modification of loss of one or more biological functions of the protein, other biological activities may still be retained. Thus, the ability of the shortened TR11, TR11SV1, and/or TR11SV2 mutein to induce and/or bind to antibodies which recognize the complete or mature form(s) of the protein generally will be retained when less than the majority of the residues of the complete or mature protein(s) are removed from the N-terminus. Whether a particular polypeptide lacking N-terminal residues of a complete protein retains such immunologic activities can readily be determined by routine methods described herein and otherwise known in the art. It is not unlikely that a TR11, TR11SV1, and/or TR11SV2 mutein with a large number of deleted N-terminal amino acid residues may retain some biological or immungenic activities. In fact, peptides composed of as few as six TR11, TR11SV1 or TR11SV2 amino acid residues may often evoke an immune response.

Accordingly, the present invention further provides polypeptides having one or more residues deleted from the amino terminus of the TR11 amino acid sequence shown in FIGS. 1A and 1B (SEQ ID NO:2), up to the leucine residue at position number 229 and polynucleotides encoding such polypeptides. In particular, the present invention provides polypeptides comprising the amino acid sequence of residues $n^1$-234 of FIGS. 1A and 1B (SEQ ID NO:2), where $n^1$ is an integer in the range of 2 to 229, and 230 is the position of the first residue from the N-terminus of the complete TR11 polypeptide believed to be required for at least immunogenic activity of the TR11 protein.

More in particular, the invention provides polynucleotides encoding polypeptides comprising, or alternatively consisting of, the amino acid sequence of residues of A-2 to V-234; Q-3 to V-234; H-4 to V-234; G-5 to V-234; A-6 to V-234; M-7 to V-234; G-8 to V-234; A-9 to V-234; F-10 to V-234; R-11 to V-234; A-12 to V-234; L-13 to V-234; C-14 to V-234; G-15 to V-234; L-16 to V-234; A-17 to V-234; L-18 to V-234; L-19 to V-234; C-20 to V-234; A-21 to V-234; L-22 to V-234; S-23 to V-234; L-24 to V-234; G-25 to V-234; Q-26 to V-234; R-27 to V-234; P-28 to V-234; T-29 to V-234; G-30 to V-234; G-31 to V-234; P-32 to V-234; G-33 to V-234; C-34 to V-234; G-35 to V-234; P-36 to V-234; G-37 to V-234; R-38 to V-234; L-39 to V-234; L-40 to V-234; L-41 to V-234; G-42 to V-234; T-43 to V-234; G-44 to V-234; T-45 to V-234; D-46 to V-234; A-47 to V-234; R-48 to V-234; C-49 to V-234; C-50 to V-234; R-51 to V-234; V-52 to V-234; H-53 to V-234; T-54 to V-234; T-55 to V-234; R-56 to V-234; C-57 to V-234; C-58 to V-234; R-59 to V-234; D-60 to V-234; Y-61 to V-234; P-62 to V-234; G-63 to V-234; E-64 to V-234; E-65 to V-234; C-66 to V-234; C-67 to V-234; S-68 to V-234; E-69 to V-234; W-70 to V-234; D-71 to V-234; C-72 to V-234; M-73 to V-234; C-74 to V-234; V-75 to V-234; Q-76 to V-234; P-77 to V-234; E-78 to V-234; F-79 to V-234; H-80 to V-234;

C-81 to V-234; G-82 to V-234; D-83 to V-234; P-84 to V-234; C-85 to V-234; C-86 to V-234; T-87 to V-234; T-88 to V-234; C-89 to V-234; R-90 to V-234; H-91 to V-234; H-92 to V-234; P-93 to V-234; C-94 to V-234; P-95 to V-234; P-96 to V-234; G-97 to V-234; Q-98 to V-234; G-99 to V-234; V-100 to V-234; Q-101 to V-234; S-102 to V-234; Q-103 to V-234; G-104 to V-234; K-105 to V-234; F-106 to V-234; S-107 to V-234; F-108 to V-234; G-109 to V-234; F-110 to V-234; Q-11 to V-234; C-112 to V-234; I-113 to V-234; D-114 to V-234; C-115 to V-234; A-116 to V-234; S-117 to V-234; G-118 to V-234; T-119 to V-234; F-120 to V-234; S-121 to V-234; G-122 to V-234; G-123 to V-234; H-124 to V-234; E-125 to V-234; G-126 to V-234; H-127 to V-234; C-128 to V-234; K-129 to V-234; P-130 to V-234; W-131 to V-234; T-132 to V-234; D-133 to V-234; C-134 to V-234; T-135 to V-234; Q-136 to V-234; F-137 to V-234; G-138 to V-234; F-139 to V-234; L-140 to V-234; T-141 to V-234; V-142 to V-234; F-143 to V-234; P-144 to V-234; G-145 to V-234; N-146 to V-234; K-147 to V-234; T-148 to V-234; H-149 to V-234; N-150 to V-234; A-151 to V-234; V-152 to V-234; C-153 to V-234; V-154 to V-234; P-155 to V-234; G-156 to V-234; S-157 to V-234; P-158 to V-234; P-159 to V-234; A-160 to V-234; E-161 to V-234; P-162 to V-234; L-163 to V-234; G-164 to V-234; W-165 to V-234; L-166 to V-234; T-167 to V-234; V-168 to V-234; V-169 to V-234; L-170 to V-234; L-171 to V-234; A-172 to V-234; V-173 to V-234; A-174 to V-234; A-175 to V-234; C-176 to V-234; V-177 to V-234; L-178 to V-234; L-179 to V-234; L-180 to V-234; T-181 to V-234; S-182 to V-234; A-183 to V-234; Q-184 to V-234; L-185 to V-234; G-186 to V-234; L-187 to V-234; H-188 to V-234; I-189 to V-234; W-190 to V-234; Q-191 to V-234; L-192 to V-234; R-193 to V-234; K-194 to V-234; T-195 to V-234; Q-196 to V-234; L-197 to V-234; L-198 to V-234; L-199 to V-234; E-200 to V-234; V-201 to V-234; P-202 to V-234; P-203 to V-234; S-204 to V-234; T-205 to V-234; E-206 to V-234; D-207 to V-234; A-208 to V-234; R-209 to V-234; S-210 to V-234; C-211 to V-234; Q-212 to V-234; F-213 to V-234; P-214 to V-234; E-215 to V-234; E-216 to V-234; E-217 to V-234; R-218 to V-234; G-219 to V-234; E-220 to V-234; R-221 to V-234; S-222 to V-234; A-223 to V-234; E-224 to V-234; E-225 to V-234; K-226 to V-234; G-227 to V-234; R-228 to V-234; and L-229 to V-234 of the TR11 amino acid sequence shown in FIGS. 1A and 1B (which is identical to the sequence shown as SEQ ID NO:2, with the exception that the amino acid residues in FIGS. 1A and 1B are numbered consecutively from 1 through 234 from the N-terminus to the C-terminus, while the amino acid residues in SEQ ID NO:2 are numbered consecutively from −25 through 209 to reflect the position of the predicted signal peptide). Polynucleotides encoding these polypeptides are also encompassed by the invention.

Moreover, even if deletion of one or more amino acids from the C-terminus of a protein results in modification of loss of one or more biological functions of the protein, other biological activities may still be retained. Thus, the ability of the shortened TR11 mutein to induce and/or bind to antibodies which recognize the complete or mature of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art. It is not unlikely that a TR11 mutein with a large number of deleted C-terminal amino acid residues may retain some biological or immungenic activities. In fact, peptides composed of as few as six TR11 amino acid residues may often evoke an immune response.

Accordingly, the present invention further provides polypeptides having one or more residues deleted from the carboxy terminus of the amino acid sequence of the TR11 shown in FIGS. 1A and 1B (SEQ ID NO:2), up to the alanine residue at position number 6, and polynucleotides encoding such polypeptides. In particular, the present invention provides polypeptides comprising the amino acid sequence of residues 1–$m^1$ of FIGS. 1A and 1B (SEQ ID NO:2), where $m^1$ is an integer in the range of 6 to 234, and 6 is the position of the first residue from the C-terminus of the complete TR11 polypeptide believed to be required for at least immunogenic activity of the TR11 protein.

More in particular, the invention provides polynucleotides encoding polypeptides comprising, or alternatively consisting of, the amino acid sequence of residues M-1 to W-233; M-1 to L-232; M-1 to D-231; M-1 to G-230; M-1 to L-229; M-1 to R-228; M-1 to G-227; M-1 to K-226; M-1 to E-225; M-1 to E-224; M-1 to A-223; M-1 to S-222; M-1 to R-221; M-1 to E-220; M-1 to G-219; M-1 to R-218; M-1 to E-217; M-1 to E-216; M-1 to E-215; M-1 to P-214; M-1 to F-213; M-1 to Q-212; M-1 to C-211; M-1 to S-210; M-1 to R-209; M-1 to A-208; M-1 to D-207; M-1 to E-206; M-1 to T-205; M-1 to S-204; M-1 to P-203; M-1 to P-202; M-1 to V-201; M-1 to E-200; M-1 to L-199; M-1 to L-198; M-1 to L-197; M-1 to Q-196; M-1 to T-195; M-1 to K-194; M-1 to R-193; M-1 to L-192; M-1 to Q-191; M-1 to W-190; M-1 to I-189; M-1 to H-188; M-1 to L-187; M-1 to G-186; M-1 to L-185; M-1 to Q-184; M-1 to A-183; M-1 to S-182; M-1 to T-181; M-1 to L-180; M-1 to L-179; M-1 to L-178; M-1 to V-177; M-1 to C-176; M-1 to A-175; M-1 to A-174; M-1 to V-173; M-1 to A-172; M-1 to L-171; M-1 to L-170; M-1 to V-169; M-1 to V-168; M-1 to T-167; M-1 to L-166; M-1 to W-165; M-1 to G-164; M-1 to L-163; M-1 to P-162; M-1 to E-161; M-1 to A-160; M-1 to P-159; M-1 to P-158; M-1 to S-157; M-1 to G-156; M-1 to P-155; M-1 to V-154; M-1 to C-153; M-1 to V-152; M-1 to A-151; M-1 to N-150; M-1 to H-149; M-1 to T-148; M-1 to K-147; M-1 to N-146; M-1 to G-145; M-1 to P-144; M-1 to F-143; M-1 to V-142; M-1 to T-141; M-1 to L-140; M-1 to F-139; M-1 to G-138; M-1 to F-137; M-1 to Q-136; M-1 to T-135; M-1 to C-134; M-1 to D-133; M-1 to T-132; M-1 to W-131; M-1 to P-130; M-1 to K-129; M-1 to C-128; M-1 to H-127; M-1 to G-126; M-1 to E-125; M-1 to H-124; M-1 to G-123; M-1 to G-122; M-1 to S-121; M-1 to F-120; M-1 to T-119; M-1 to G-118; M-1 to S-117; M-1 to A-116; M-1 to C-115; M-1 to D-114; M-1 to I-113; M-1 to C-112; M-1 to Q-111; M-1 to F-110; M-1 to G-109; M-1 to F-108; M-1 to S-107; M-1 to F-106; M-1 to K-105; M-1 to G-104; M-1 to Q-103; M-1 to S-102; M-1 to Q-101; M-1 to V-100; M-1 to G-99; M-1 to Q-98; M-1 to G-97; M-1 to P-96; M-1 to P-95; M-1 to C-94; M-1 to P-93; M-1 to H-92; M-1 to H-91; M-1 to R-90; M-1 to C-89; M-1 to T-88; M-1 to T-87; M-1 to C-86; M-1 to C-85; M-1 to P-84; M-1 to D-83; M-1 to G-82; M-1 to C-81; M-1 to H-80; M-1 to F-79; M-1 to E-78; M-1 to P-77; M-1 to Q-76; M-1 to V-75; M-1 to C-74; M-1 to M-73; M-1 to C-72; M-1 to D-71; M-1 to W-70; M-1 to E-69; M-1 to S-68; M-1 to C-67; M-1 to C-66; M-1 to E-65; M-1 to E-64; M-1 to G-63; M-1 to P-62; M-1 to Y-61; M-1 to D-60; M-1 to R-59; M-1 to C-58; M-1 to C-57; M-1 to R-56; M-1 to T-55; M-1 to T-54; M-1 to H-53; M-1 to V-52; M-1 to R-51; M-1 to C-50; M-1 to C-49; M-1 to R-48; M-1 to A-47; M-1 to D-46; M-1 to T-45; M-1 to G-44; M-1 to T-43; M-1 to G-42; M-1 to L-41; M-1 to L-40; M-1 to L-39; M-1 to R-38; M-1 to G-37; M-1 to P-36; M-1 to G-35; M-1 to C-34; M-1 to G-33; M-1 to P-32; M-1 to G-31; M-1 to G-30; M-1 to T-29; M-1 to P-28; M-1 to R-27; M-1 to Q-26; M-1 to G-25; M-1 to L-24; M-1 to S-23; M-1 to L-22; M-1 to A-21; M-1 to C-20; M-1 to L-19; M-1 to L-18; M-1 to A-17; M-1 to L-16; M-1 to G-15; M-1 to C-14; M-1 to L-13; M-1 to A-12; M-1 to R-11; M-1 to F-10; M-1 to A-9; M-1 to G-8; M-1 to M-7; and M-1 to A-6 of the sequence of the TR11 sequence shown in FIGS. 1A and 1B (which is identical to the sequence shown as SEQ ID NO:2, with the exception that the amino acid residues in FIGS. 1A and 1B are numbered consecutively from 1 through 234 from the N-terminus to the C-terminus, while the amino acid residues in SEQ ID NO:2 are numbered consecutively from −25 through 209 to reflect the position of the predicted signal peptide). Polynucleotides encoding these polypeptides also are provided.

The invention also provides polypeptides having one or more amino acids deleted from both the amino and the carboxyl termini of a soluble TR11 polypeptide, which may be described generally as having residues $n^1$–$m^1$ of FIGS. 1A and 1B (SEQ ID NO:2), where $n^1$ and $m^1$ are integers as described above.

The present invention further provides polypeptides having one or more residues deleted from the amino terminus of the TR11SV1 amino acid sequence shown in SEQ ID NO:4, up to the leucine residue at position number 236 and polynucleotides encoding such polypeptides. In particular, the present invention provides polypeptides comprising the amino acid sequence of residues $n^2$-241 of FIGS. 2A and 2B (SEQ ID NO:4), where $n^2$ is an integer in the range of 2 to 236, and 237 is the position of the first residue from the N-terminus of the complete TR11SV1 polypeptide believed to be required for at least immunogenic activity of the TR11SV1 protein.

More in particular, the invention provides polynucleotides encoding polypeptides comprising, or alternatively consisting of, the amino acid sequence of residues of A-2 to V-241; P-3 to V-241; G-4 to V-241; E-5 to V-241; R-6 to V-241; D-7 to V-241; S-8 to V-241; W-9 to V-241; I-10 to V-241; N-11 to V-241; P-12 to V-241; G-13 to V-241; P-14 to V-241; D-15 to V-241; S-16 to V-241; Q-17 to V-241; P-18 to V-241; G-19 to V-241; A-20 to V-241; L-21 to V-241; C-22 to V-241; S-23 to V-241; L-24 to V-241; E-25 to V-241; P-26 to V-241; T-27 to V-241; V-28 to V-241; G-29 to V-241; G-30 to V-241; E-31 to V-241; R-32 to V-241; T-33 to V-241; T-34 to V-241; S-35 to V-241; L-36 to V-241; P-37 to V-241; W-38 to V-241; R-39 to V-241; A-40 to V-241; E-41 to V-241; G-42 to V-241; R-43 to V-241; P-44 to V-241; G-45 to V-241; E-46 to V-241; E-47 to V-241; G-48 to V-241; A-49 to V-241; S-50 to V-241; A-51 to V-241; Q-52 to V-241; L-53 to V-241; L-54 to V-241; G-55 to V-241; G-56 to V-241; W-57 to V-241; P-58 to V-241; V-59 to V-241; S-60 to V-241; C-61 to V-241; P-62 to V-241; G-63 to V-241; E-64 to V-241; E-65 to V-241; C-66 to V-241; C-67 to V-241; S-68 to V-241; E-69 to V-241; W-70 to V-241; D-71 to V-241; C-72 to V-241; M-73 to V-241; C-74 to V-241; V-75 to V-241; Q-76 to V-241; P-77 to V-241; E-78 to V-241; F-79 to V-241; H-80 to V-241; C-81 to V-241; G-82 to V-241; D-83 to V-241; P-84 to V-241; C-85 to V-241; C-86 to V-241; T-87 to V-241; T-88 to V-241; C-89 to V-241; R-90 to V-241; H-91 to V-241; H-92 to V-241; P-93 to V-241; C-94 to V-241; P-95 to V-241; P-96 to V-241; G-97 to V-241; Q-98 to V-241; G-99 to V-241; V-100 to V-241; Q-101 to V-241; S-102 to V-241; Q-103 to V-241; G-104 to V-241; K-105 to V-241; F-106 to V-241; S-107 to V-241; F-108 to V-241; G-109 to V-241; F-110 to V-241; Q-111 to V-241; C-112 to V-241; I-113 to V-241; D-114 to V-241; C-115 to V-241; A-116 to V-241; S-117 to V-241; G-118 to V-241; T-119 to V-241; F-120 to V-241; S-121 to V-241; G-122 to V-241; G-123 to V-241; H-124 to V-241; E-125 to V-241; G-126 to V-241; H-127 to V-241; C-128 to V-241; K-129 to V-241; P-130 to V-241; W-131 to V-241; T-132 to V-241; D-133 to V-241; C-134 to V-241; T-135 to V-241; Q-136 to V-241; F-137 to V-241; G-138 to V-241; F-139 to V-241; L-140 to V-241; T-141 to V-241; V-142 to V-241; F-143 to V-241; P-144 to V-241; G-145 to V-241; N-146 to V-241; K-147 to V-241; T-148 to V-241; H-149 to V-241; N-150 to V-241; A-151 to V-241; V-152 to V-241; C-153 to V-241; V-154 to V-241; P-155 to V-241; G-156 to V-241; S-157 to V-241; P-158 to V-241; P-159 to V-241; A-160 to V-241; E-161 to V-241; P-162 to V-241; L-163 to V-241; G-164 to V-241; W-165 to V-241; L-166 to V-241; T-167 to V-241; V-168 to V-241; V-169 to V-241; L-170 to V-241; L-171 to V-241; A-172 to V-241; V-173 to V-241; A-174 to V-241; A-175 to V-241; C-176 to V-241; V-177 to V-241; L-178 to V-241; L-179 to V-241; L-180 to V-241; T-181 to V-241; S-182 to V-241; A-183 to V-241; Q-184 to V-241; L-185 to V-241; G-186 to V-241; L-187 to V-241; H-188 to V-241; I-189 to V-241; W-190 to V-241; Q-191 to V-241; L-192 to V-241; R-193 to V-241; S-194 to V-241; Q-195 to V-241; C-196 to V-241; M-197 to V-241; W-198 to V-241; P-199 to V-241; R-200 to V-241; E-201 to V-241; T-202 to V-241; Q-203 to V-241; L-204 to V-241; L-205 to V-241; L-206 to V-241; E-207 to V-241; V-208 to V-241; P-209 to V-241; P-210 to V-241; S-211 to V-241; T-212 to V-241; E-213 to V-241; D-214 to V-241; A-215 to V-241; R-216 to V-241; S-217 to V-241; C-218 to V-241; Q-219 to V-241; F-220 to V-241; P-221 to V-241; E-222 to V-241; E-223 to V-241; E-224 to V-241; R-225 to V-241; G-226 to V-241; E-227 to V-241; R-228 to V-241; S-229 to V-241; A-230 to V-241; E-231 to V-241; E-232 to V-241; K-233 to V-241; G-234 to V-241; R-235 to V-241; and L-236 to V-241 of the TR11SV1 amino acid sequence shown in FIGS. 2A and 2B (which is identical to the sequence shown as SEQ ID NO:4). Polynucleotides encoding these polypeptides are also encompassed by the invention.

As mentioned above, even if deletion of one or more amino acids from the C-terminus of a protein results in modification of loss of one or more biological functions of the protein, other biological activities may still be retained. Thus, the ability of the shortened TR11SV1 mutein to induce and/or bind to antibodies which recognize the complete or mature of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art. It is not unlikely that a TR11SV1 mutein with a large number of deleted C-terminal amino acid residues may retain some biological or immungenic activities. In fact, peptides composed of as few as six TR11SV1 amino acid residues may often evoke an immune response.

Accordingly, the present invention further provides polypeptides having one or more residues deleted from the carboxy terminus of the amino acid sequence of the TR11SV1 shown in SEQ ID NO:4, up to the arginine residue at position number 6, and polynucleotides encoding such polypeptides. In particular, the present invention provides polypeptides comprising the amino acid sequence of residues 1–$m^2$ of FIGS. 2A and 2B (SEQ ID NO:4), where $m^2$ is an integer in the range of 6 to 241, and 6 is the position of the first residue from the C-terminus of the complete TR11SV1 polypeptide believed to be required for at least immunogenic activity of the TR11SV1 protein.

More in particular, the invention provides polynucleotides encoding polypeptides comprising, or alternatively consisting of, the amino acid sequence of residues M-1 to W-240; M-1 to L-239; M-1 to D-238; M-1 to G-237; M-1 to L-236; M-1 to R-235; M-1 to G-234; M-1 to K-233; M-1 to E-232; M-1 to E-231; M-1 to A-230; M-1 to S-229; M-1 to R-228; M-1 to E-227; M-1 to G-226; M-1 to R-225; M-1 to E-224; M-1 to E-223; M-1 to E-222; M-1 to P-221; M-1 to F-220; M-1 to Q-219; M-1 to C-218; M-1 to S-217; M-1 to R-216; M-1 to A-215; M-1 to D-214; M-1 to E-213; M-1 to T-212; M-1 to S-211; M-1 to P-210; M-1 to P-209; M-1 to V-208; M-1 to E-207; M-1 to L-206; M-1 to L-205; M-1 to L-204; M-1 to Q-203; M-1 to T-202; M-1 to E-201; M-1 to R-200; M-1 to P-199; M-1 to W-198; M-1 to M-197; M-1 to C-196; M-1 to Q-195; M-1 to S-194; M-1 to R-193; M-1 to L-192; M-1 to Q-191; M-1 to W-190; M-1 to I-189; M-1 to H-188; M-1 to L-187; M-1 to G-186; M-1 to L-185; M-1 to Q-184; M-1 to A-183; M-1 to S-182; M-1 to T-181; M-1 to L-180; M-1 to L-179; M-1 to L-178; M-1 to V-177; M-1 to C-176; M-1 to A-175; M-1 to A-174; M-1 to V-173; M-1 to A-172; M-1 to L-171; M-1 to L-170; M-1 to V-169; M-1 to V-168; M-1 to T-167; M-1 to L-166; M-1 to W-165; M-1 to G-164; M-1 to L-163; M-1 to P-162; M-1 to E-161; M-1 to A-160; M-1 to P-159; M-1 to P-158; M-1 to S-157; M-1 to G-156; M-1 to P-155; M-1 to V-154; M-1 to C-153; M-1 to V-152; M-1 to A-151; M-1 to N-150; M-1 to H-149; M-1 to T-148; M-1 to K-147; M-1 to N-146; M-1 to G-145; M-1 to P-144; M-1 to F-143; M-1 to V-142; M-1 to T-141; M-1 to L-140; M-1 to F-139; M-1 to G-138; M-1 to F-137; M-1 to Q-136; M-1 to T-135; M-1 to C-134; M-1 to D-133; M-1 to T-132; M-1 to W-131; M-1 to P-130; M-1 to K-129; M-1 to C-128; M-1 to H-127; M-1 to G-126; M-1 to E-125; M-1 to H-124; M-1 to G-123; M-1 to G-122; M-1 to S-121; M-1 to F-120; M-1 to T-119; M-1 to G-118; M-1 to S-117; M-1 to A-116; M-1 to C-115; M-1 to D-114; M-1 to I-113; M-1 to C-112; M-1 to Q-111; M-1 to F-110; M-1 to G-109; M-1 to F-108; M-1 to S-107; M-1 to F-106; M-1 to K-105; M-1 to G-104; M-1 to Q-103; M-1 to S-102; M-1 to Q-101; M-1 to V-100; M-1 to G-99; M-1 to Q-98; M-1 to G-97; M-1 to P-96; M-1 to P-95; M-1 to C-94; M-1 to P-93; M-1 to H-92; M-1 to H-91; M-1 to R-90; M-1 to C-89; M-1 to T-88; M-1 to T-87; M-1 to C-86; M-1 to C-85; M-1 to P-84; M-1 to D-83; M-1 to O-82; M-1 to C-81; M-1 to H-80; M-1 to F-79; M-1 to E-78; M-1 to P-77; M-1 to Q-76; M-1 to V-75; M-1 to C-74; M-1 to M-73; M-1 to C-72; M-1 to D-71; M-1 to W-70; M-1 to E-69; M-1 to S-68; M-1 to C-67; M-1 to C-66; M-1 to E-65; M-1 to E-64; M-1 to G-63; M-1 P-62; M-1 to C-61; M-1 to S-60; M-1 to V-59; M-1 to P-58; M-1 to W-57; M-1 to G-56; M-1 to G-55; M-1 to L-54; M-1 to L-53; M-1 to Q-52; M-1 to A-51; M-1 to S-50; M-1 to A-49; M-1 to G-48; M-1 to E-47; M-1 to E-46; M-1 to G-45; M-1 to P-44; M-1 to R-43; M-1 to G-42; M-1 to E-41; M-1 to A-40; M-1 to R-39; M-1 to W-38; M-1 to P-37; M-1 to L-36; M-1 to S-35; M-1 to T-34; M-1 to T-33; M-1 to R-32; M-1 to E-31; M-1 to G-30; M-1 to G-29; M-1 to V-28; M-1 to T-27; M-1 to P-26; M-1 to E-25; M-1 to L-24; M-1 to S-23; M-1 to C-22; M-1 to L-21; M-1 to A-20; M-1 to G-19; M-1 to P-18; M-1 to Q-17; M-1 to S-16; M-1 to D-15; M-1 to P-14; M-1 to G-13; M-1 to P-12; M-1 to N-11; M-1 to I-10; M-1 to W-9; M-1 to S-8; M-1 to D-7; and M-1 to R-6 of the sequence of the TR11SV1 sequence shown in FIGS. 2A and 2B (which is identical to the sequence shown as SEQ ID NO:4). Polynucleotides encoding these polypeptides also are provided.

The invention also provides polypeptides having one or more amino acids deleted from both the amino and the carboxyl termini of a TR11SV1 polypeptide, which may be described generally as having residues $n^2$–$m^2$ of FIGS. 2A and 2B (SEQ ID NO:4), where $n^2$ and $m^2$ are integers as described above.

In addition, the present invention further provides polypeptides having one or more residues deleted from the amino terminus of the TR11SV2 amino acid sequence shown in FIGS. 3A and 3B (SEQ ID NO:6), up to the leucine residue at position number 235 and polynucleotides encoding such polypeptides. In particular, the present invention provides polypeptides comprising the amino acid sequence of residues $n^3$-240 of FIGS. 3A and 3B (SEQ ID NO:6), where $n^3$ is an integer in the range of 2 to 235, and 236 is the position of the first residue from the N-terminus of the complete TR11SV2 polypeptide believed to be required for at least immunogenic activity of the TR11SV2 protein.

More in particular, the invention provides polynucleotides encoding polypeptides comprising, or alternatively consisting of, the amino acid sequence of residues of G-2 to V-240; A-3 to V-240; F-4 to V-240; R-5 to V-240; A-6 to V-240; L-7 to V-240; C-8 to V-240; G-9 to V-240; L-10 to V-240; A-11 to V-240; L-12 to V-240; L-13 to V-240; C-14 to V-240; A-15 to V-240; L-16 to V-240; S-17 to V-240; L-18 to V-240; G-19 to V-240; Q-20 to V-240; R-21 to V-240; P-22 to V-240; T-23 to V-240; G-24 to V-240; G-25 to V-240; P-26 to V-240; G-27 to V-240; C-28 to V-240; G-29 to V-240; G-31 to V-240; R-32 to V-240; L-33 to V-240; L-34 to V-240; L-35 to V-240; G-36 to V-240; T-37 to V-240; G-38 to V-240; T-39 to V-240; D-40 to V-240; A-41 to V-240; R-42 to V-240; C-43 to V-240; C-44 to V-240; R-45 to V-240; V-46 to V-240; H-47 to V-240; T-48 to V-240; T-49 to V-240; R-50 to V-240; C-51 to V-240; C-52 to V-240; R-53 to V-240; D-54 to V-240; Y-55 to V-240; P-56 to V-240; A-57 to V-240; Q-58 to V-240; L-59 to V-240; L-60 to V-240; G-61 to V-240; G-62 to V-240; W-63 to V-240; P-64 to V-240; V-65 to V-240; S-66 to V-240; C-67 to V-240; P-68 to V-240; G-69 to V-240; E-70 to V-240; E-71 to V-240; C-72 to V-240; C-73 to V-240; S-74 to V-240; E-75 to V-240; W-76 to V-240; D-77 to V-240; C-78 to V-240; M-79 to V-240; C-80 to V-240; V-81 to V-240; Q-82 to V-240; P-83 to V-240; E-84 to V-240; F-85 to V-240; H-86 to V-240; C-87 to V-240; G-88 to V-240; D-89 to V-240; P-90 to V-240; C-91 to V-240; C-92 to V-240; T-93 to V-240; T-94 to V-240; C-95 to V-240; R-96 to V-240; H-97 to V-240; H-98 to V-240; P-99 to V-240; C-100 to V-240; P-101 to V-240; P-102 to V-240; G-103 to V-240; Q-104 to V-240; G-105 to V-240; V-106 to V-240; Q-107 to V-240; S-108 to V-240; Q-109 to V-240; G-110 to V-240; K-111 to V-240; F-112 to V-240; S-113 to V-240; F-114 to V-240; G-115 to V-240; F-116 to V-240; Q-117 to V-240; C-118 to V-240; I-119 to V-240; D-120 to V-240; C-121 to V-240; A-122 to V-240; S-123 to V-240; G-124 to V-240; T-125 to V-240; F-126 to V-240; S-127 to V-240; G-128 to V-240; G-129 to V-240; H-130 to V-240; E-131 to V-240; G-132 to V-240; H-133 to V-240; C-134 to V-240; K-135 to V-240; P-136 to V-240; W-137 to V-240; T-138 to V-240; D-139 to V-240; C-140 to V-240; T-141 to V-240; Q-142 to V-240; F-143 to V-240; G-144 to V-240; F-145 to V-240; L-146 to V-240; T-147 to V-240; V-148 to V-240; F-149 to V-240; P-150 to V-240; G-151 to V-240; N-152 to V-240; K-153 to V-240; T-154 to V-240; H-155 to V-240; N-156 to V-240; A-157 to V-240; V-158 to V-240; C-159 to V-240; V-160 to V-240; P-161 to V-240; G-162 to V-240; S-163 to V-240; P-164 to V-240; P-165 to V-240; A-166 to V-240; E-167 to V-240; P-168 to V-240; L-169 to V-240; G-170 to V-240; W-171 to V-240; L-172 to V-240; T-173 to V-240; V-174 to V-240; V-175 to V-240; L-176 to V-240; L-177 to V-240; A-178 to V-240; V-179 to V-240; A-180 to V-240; A-181 to V-240; C-182 to V-240; V-183 to V-240; L-184 to V-240; L-185 to V-240; L-186 to V-240; T-187 to V-240; S-188 to V-240; A-189 to V-240; Q-190 to V-240; L-191 to V-240; G-192 to V-240; L-193 to V-240; H-194 to V-240; I-195 to V-240; W-196 to V-240; Q-197 to V-240; L-198 to V-240; R-199 to V-240; K-200 to V-240; T-201 to V-240; Q-202 to V-240; L-203 to V-240; L-204 to V-240; L-205 to V-240; E-206 to V-240; V-207 to V-240; P-208 to V-240; P-209 to V-240; S-210 to V-240; T-211 to V-240; E-212 to V-240; D-213 to V-240; A-214 to V-240; R-215 to V-240; S-216 to V-240; C-217 to V-240; Q-218 to V-240; F-219 to V-240; P-220 to V-240; E-221 to V-240; E-222 to V-240; E-223 to V-240; R-224 to V-240; G-225 to V-240; E-226 to V-240; R-227 to V-240; S-228 to V-240; A-229 to V-240; E-230 to V-240; E-231 to V-240; K-232 to V-240; G-233 to V-240; R-234 to V-240; and L-235 to V-240 of the TR11SV2 amino acid sequence shown in FIGS. 3A and 3B (which is identical to the sequence shown as SEQ ID NO:6, with the exception that the amino acid residues in FIGS. 3A and 3B are numbered consecutively from 1 through 240 from the N-terminus to the C-terminus, while the amino acid residues in SEQ ID NO:6 are numbered consecutively from −19 through 221 to reflect the position of the predicted signal peptide). Polynucleotides encoding these polypeptides are also encompassed by the invention.

Also as mentioned above, even if deletion of one or more amino acids from the C-terminus of a protein results in modification of loss of one or more biological functions of the protein, other biological activities may still be retained. Thus, the ability of the shortened TR11SV2 mutein to induce and/or bind to antibodies which recognize the complete or mature of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art. It is not unlikely that a TR11SV2 mutein with a large number of deleted C-terminal amino acid residues may retain some biological or immunogenic activities. In fact, peptides composed of as few as six TR11SV2 amino acid residues may often evoke an immune response.

Accordingly, the present invention further provides polypeptides having one or more residues deleted from the carboxy terminus of the amino acid sequence of the TR11SV2 shown in FIGS. 3A and 3B (SEQ ID NO:6), up to the alanine residue at position number 6, and polynucleotides encoding such polypeptides. In particular, the present invention provides polypeptides comprising the amino acid sequence of residues 1–$m^3$ of FIGS. 3A and 3B (SEQ ID NO:6), where $m^3$ is an integer in the range of 6 to 240, and 6 is the position of the first residue from the C-terminus of the complete TR11SV2 polypeptide believed to be required for at least immunogenic activity of the TR11SV2 protein.

More in particular, the invention provides polynucleotides encoding polypeptides comprising, or alternatively consisting of, the amino acid sequence of residues M-1 to W-239; M-1 to L-238; M-1 to D-237; M-1 to G-236; M-1 to L-235; M-1 to R-234; M-1 to G-233; M-1 to K-232; M-1 to E-231; M-1 to E-230; M-1 to A-229; M-1 to S-228; M-1 to R-227; M-1 to E-226; M-1 to G-225; M-1 to R-224; M-1 to E-223; M-1 to E-222; M-1 to E-221; M-1 to P-220; M-1 to F-219; M-1 to Q-218; M-1 to C-217; M-1 to S-216; M-1 to R-215; M-1 to A-214; M-1 to D-213; M-1 to E-212; M-1 to T-211; M-1 to S-210; M-1 to P-209; M-1 to P-208; M-1 to V-207; M-1 to E-206; M-1 to L-205; M-1 to L-204; M-1 to L-203; M-1 to Q-202; M-1 to T-201; M-1 to K-200; M-1 to R-199; M-1 to L-198; M-1 to Q-197; M-1 to W-196; M-1 to I-195; M-1 to H-194; M-1 to L-193; M-1 to G-192; M-1 to L-191; M-1 to Q-190; M-1 to A-189; M-1 to S-188; M-1 to T-187; M-1 to L-186; M-1 to L-185; M-1 to L-184; M-1 to V-183; M-1 to C-182; M-1 to A-181; M-1 to A-180; M-1 to V-179; M-1 to A-178; M-1 to L-177; M-1 to L-176; M-1 to V-175; M-1 to V-174; M-1 to T-173; M-1 to L-172; M-1 to W-171; M-1 to G-170; M-1 to L-169; M-1 to P-168; M-1 to E-167; M-1 to A-166; M-1 to P-165; M-1 to P-164; M-1 to S-163; M-1 to G-162; M-1 to P-161; M-1 to V-160; M-1 to C-159; M-1 to V-158; M-1 to A-157; M-1 to N-156; M-1 to H-155; M-1 to T-154; M-1 to K-153; M-1 to N-152; M-1 to G-151; M-1 to P-150; M-1 to F-149; M-1 to V-148; M-1 to T-147; M-1 to L-146; M-1 to F-145; M-1 to G-144; M-1 to F-143; M-1 to Q-142; M-1 to T-141; M-1 to C-140; M-1 to D-139; M-1 to T-138; M-1 to W-137; M-1 to P-136; M-1 to K-135; M-1 to C-134; M-1 to H-133; M-1 to G-132; M-1 to E-131; M-1 to H-130; M-1 to G-129; M-1 to G-128; M-1 to S-127; M-1 to F-126; M-1 to T-125; M-1 to G-124; M-1 to S-123; M-1 to A-122; M-1 to C-121; M-1 to D-120; M-1 to I-119; M-1 to C-118; M-1 to Q-117; M-1 to F-116; M-1 to G-115; M-1 to F-114; M-1 to S-113; M-1 to F-112; M-1 to K-111; M-1 to G-110; M-1 to Q-109; M-1 to S-108; M-1 to Q-107; M-1 to V-106; M-1 to G-105; M-1 to Q-104; M-1 to G-103; M-1 to P-102; M-1 to P-101; M-1 to C-100; M-1 to P-99; M-1 to H-98; M-1 to H-97; M-1 to R-96; M-1 to C-95; M-1 to T-94; M-1 to T-93; M-1 to C-92; M-1 to C-91; M-1 to P-90; M-1 to D-89; M-1 to G-88; M-1 to C-87; M-1 to H-86; M-1 to F-85; M-1 to E-84; M-1 to P-83; M-1 to Q-82; M-1 to V-81; M-1 to C-80; M-1 to M-79; M-1 to C-78; M-1 to D-77; M-1 to W-76; M-1 to E-75; M-1 to S-74; M-1 to C-73; M-1 to C-72; M-1 to E-71; M-1 to E-70; M-1 to G-69; M-1 to P-68; M-1 to C-67; M-1 to S-66; M-1 to V-65; M-1 to P-64; M-1 to W-63; M-1 to G-62; M-1 to G-61; M-1 to L-60; M-1 to L-59; M-1 to Q-58; M-1 to A-57; M-1 to P-56; M-1 to Y-55; M-1 to D-54; M-1 to R-53; M-1 to C-52; M-1 to C-51; M-1 to R-50; M-1 to T-49; M-1 to T-48; M-1 to H-47; M-1 to V-46; M-1 to R-45; M-1 to C-44; M-1 to C-43; M-1 to R-42; M-1 to A-41; M-1 to D-40; M-1 to T-39; M-1 to G-38; M-1 to T-37; M-1 to G-36; M-1 to L-35; M-1 to L-34; M-1 to L-33; M-1 to R-32; M-1 to G-31; M-1 to P-30; M-1 to G-29; M-1 to C-28; M-1 to G-27; M-1 to P-26; M-1 to G-25; M-1 to G-24; M-1 to T-23; M-1 to P-22; M-1 to R-21; M-1 to Q-20; M-1 to G-19; M-1 to L-18; M-1 to S-17; M-1 to L-16; M-1 to A-15; M-1 to C-14; M-1 to L-13; M-1 to L-12; M-1 to A-11; M-1 to L-10; M-1 to G-9; M-1 to C-8; M-1 to L-7; and M-1 to A-6 of the sequence of the TR11SV2 sequence shown in FIGS. 3A and 3B (which is identical to the sequence shown as SEQ ID NO:6, with the exception that the amino acid residues in FIGS. 3A and 3B are numbered consecutively from 1 through 240 from the N-terminus to the C-terminus, while the amino acid residues in SEQ ID NO:6 are numbered consecutively from −19 through 221 to reflect the position of the predicted signal peptide). Polynucleotides encoding these polypeptides also are provided.

The invention also provides polypeptides having one or more amino acids deleted from both the amino and the carboxyl termini of a TR11SV2 polypeptide, which may be described generally as having residues $n^3$–$m^3$ of FIGS. 3A and 3B (SEQ ID NO:6), where $n^3$ and $m^3$ are integers as described above.

In addition, the present invention further provides polypeptides having one or more residues deleted from the amino terminus of the predicted extracellular domain of the TR11 amino acid sequence shown in FIGS. 1A and 1B (SEQ ID NO:2), up to the glycine residue at position number 156 and polynucleotides encoding such polypeptides. In particular, the present invention provides polypeptides comprising the amino acid sequence of residues $n^4$–162 of FIGS. 1A and 1B (SEQ ID NO:2), where $n^4$ is an integer in the range of 25 to 156, and 157 is the position of the first residue from the N-terminus of the predicted extracellular domain of the TR11 polypeptide believed to be required for at least immunogenic activity of the predicted extracellular domain of the TR11 protein.

More in particular, the invention provides polynucleotides encoding polypeptides comprising, or alternatively consisting of, the amino acid sequence of residues of G-25 to P-162; Q-26 to P-162; R-27 to P-162; P-28 to P-162; T-29 to P-162; G-30 to P-162; G-31 to P-162; P-32 to P-162; G-33 to P-162; C-34 to P-162; G-35 to P-162; P-36 to P-162; G-37 to P-162; R-38 to P-162; L-39 to P-162; L-40 to P-162; L-41 to P-162; G-42 to P-162; T-43 to P-162; G-44 to P-162; T-45 to P-162; D-46 to P-162; A-47 to P-162; R-48 to P-162; C-49 to P-162; C-50 to P-162; R-51 to P-162; V-52 to P-162; H-53 to P-162; T-54 to P-162; T-55 to P-162; R-56 to P-162; C-57 to P-162; C-58 to P-162; R-59 to P-162; D-60 to P-162; Y-61 to P-162; P-62 to P-162; G-63 to P-162; E-64 to P-162; E-65 to P-162; C-66 to P-162; C-67 to P-162; S-68 to P-162; E-69 to P-162; W-70 to P-162; D-71 to P-162; C-72 to P-162; M-73 to P-162; C-74 to P-162; V-75 to P-162; Q-76 to P-162; P-77 to P-162; E-78 to P-162; F-79 to P-162; H-80 to P-162; C-81 to P-162; G-82 to P-162; D-83 to P-162; P-84 to P-162; C-85 to P-162; C-86 to P-162; T-87 to P-162; T-88 to P-162; C-89 to P-162; R-90 to P-162; H-91 to P-162; H-92 to P-162; P-93 to P-162; C-94 to P-162; P-95 to P-162; P-96 to P-162; G-97 to P-162; Q-98 to P-162; G-99 to P-162; V-100 to P-162; Q-101 to P-162; S-102 to P-162; Q-103 to P-162; G-104 to P-162; K-105 to P-162; F-106 to P-162; S-107 to P-162; F-108 to P-162; G-109 to P-162; F-110 to P-162; Q-111 to P-162; C-112 to P-162; I-113 to P-162; D-114 to P-162; C-115 to P-162; A-116 to P-162; S-117 to P-162; G-118 to P-162; T-119 to P-162; F-120 to P-162; S-121 to P-162; G-122 to P-162; G-123 to P-162; H-124 to P-162; E-125 to P-162; G-126 to P-162; H-127 to P-162; C-128 to P-162; K-129 to P-162; P-130 to P-162; W-131 to P-162; T-132 to P-162; D-133 to P-162; C-134 to P-162; T-135 to P-162; Q-136 to P-162; F-137 to P-162; G-138 to P-162; F-139 to P-162; L-140 to P-162; T-141 to P-162; V-142 to P-162; F-143 to P-162; P-144 to P-162; G-145 to P-162; N-146 to P-162; K-147 to P-162; T-148 to P-162; H-149 to P-162; N-150 to P-162; A-151 to P-162; V-152 to P-162; C-153 to P-162; V-154 to P-162; P-155 to P-162; and G-156 to P-162 of the TR11 amino acid sequence shown in FIGS. 1A and 1B (which is identical to the sequence shown as SEQ ID NO:2, with the exception that the amino acid residues in FIGS. 1A and 1B are numbered consecutively from 1 through 234 from the N-terminus to the C-terminus, while the amino acid residues in SEQ ID NO:2 are numbered consecutively from –25 through 209 to reflect the position of the predicted signal peptide). Polynucleotides encoding these polypeptides are also encompassed by the invention.

The present invention further provides polypeptides having one or more residues deleted from the carboxy terminus of the predicted extracellular domain of the amino acid sequence of the TR11 shown in FIGS. 1A and 1B (SEQ ID NO:2), up to the glycine residue at position number 31, and polynucleotides encoding such polypeptides. In particular, the present invention provides polypeptides comprising the amino acid sequence of residues 25–$m^4$ of FIGS. 1A and 1B (SEQ ID NO:2), where $m^4$ is an integer in the range of 31 to 162, and 30 is the position of the first residue from the C-terminus of the predicted extracellular domain of the TR11 polypeptide believed to be required for at least immunogenic activity of the TR11 protein.

More in particular, the invention provides polynucleotides encoding polypeptides comprising, or alternatively consisting of, the amino acid sequence of residues G-25 to P-162; G-25 to E-161; G-25 to A-160; G-25 to P-159; G-25 to P-158; G-25 to S-157; G-25 to G-156; G-25 to P-155; G-25 to V-154; G-25 to C-153; G-25 to V-152; G-25 to A-151; G-25 to N-150; G-25 to H-149; G-25 to T-148; G-25 to K-147; G-25 to N-146; G-25 to G-145; G-25 to P-144; G-25 to F-143; G-25 to V-142; G-25 to T-141; G-25 to L-140; G-25 to F-139; G-25 to G-138; G-25 to F-137; G-25 to Q-136; G-25 to T-135; G-25 to C-134; G-25 to D-133; G-25 to T-132; G-25 to W-131; G-25 to P-130; G-25 to K-129; G-25 to C-128; G-25 to H-127; G-25 to G-126; G-25 to E-125; G-25 to H-124; G-25 to G-123; G-25 to G-122; G-25 to S-121; G-25 to F-120; G-25 to T-119; G-25 to G-118; G-25 to S-117; G-25 to A-116; G-25 to C-115; G-25 to D-114; G-25 to I-113; G-25 to C-112; G-25 to Q-111; G-25 to F-110; G-25 to G-109; G-25 to F-108; G-25 to S-107; G-25 to F-106; G-25 to K-105; G-25 to G-104; G-25 to Q-103; G-25 to S-102; G-25 to Q-101; G-25 to V-100; G-25 to G-99; G-25 to Q-98; G-25 to G-97; G-25 to P-96; G-25 to P-95; G-25 to C-94; G-25 to P-93; G-25 to H-92; G-25 to H-91; G-25 to R-90; G-25 to C-89; G-25 to T-88; G-25 to T-87; G-25 to C-86; G-25 to C-85; G-25 to P-84; G-25 to D-83; G-25 to G-82; G-25 to C-81; G-25 to H-80; G-25 to F-79; G-25 to E-78; G-25 to P-77; G-25 to Q-76; G-25 to V-75; G-25 to C-74; G-25 to M-73; G-25 to C-72; G-25 to D-71; G-25 to W-70; G-25 to E-69; G-25 to S-68; G-25 to C-67; G-25 to C-66; G-25 to E-65; G-25 to E-64; G-25 to G-63; G-25 to P-62; G-25 to Y-61; G-25 to D-60; G-25 to R-59; G-25 to C-58; G-25 to C-57; G-25 to R-56; G-25 to T-55; G-25 to T-54; G-25 to H-53; G-25 to V-52; G-25 to R-51; G-25 to C-50; G-25 to C-49; G-25 to R-48; G-25 to A-47; G-25 to D-46; G-25 to T-45; G-25 to G-44; G-25 to T-43; G-25 to G-42; G-25 to L-41; G-25 to L-40; G-25 to L-39; G-25 to R-38; G-25 to G-37; G-25 to P-36; G-25 to G-35; G-25 to C-34; G-25 to G-33; G-25 to P-32; and G-25 to G-31 of the sequence of the TR11 sequence shown in FIGS. 1A and 1B (which is identical to the sequence shown as SEQ ID NO:2, with the exception that the amino acid residues in FIGS. 1A and 1B are numbered consecutively from 1 through 234 from the N-terminus to the C-terminus, while the amino acid residues in SEQ ID NO:2 are numbered consecutively from –25 through 209 to reflect the position of the predicted signal peptide). Polynucleotides encoding these polypeptides also are provided.

The invention also provides polypeptides having one or more amino acids deleted from both the amino and the carboxyl termini of a soluble TR11 polypeptide, which may be described generally as having residues $n^4$–$m^4$ of FIGS. 1A and 1B (SEQ ID NO:2), where $n^4$ and $m^4$ are integers as described above.

In addition, the present invention further provides polypeptides having one or more residues deleted from the amino terminus of the predicted extracellular domain of the TR11SV1 amino acid sequence shown in FIGS. 2A and 2B (SEQ ID NO:4), up to the glycine residue at position number 156 and polynucleotides encoding such polypeptides. In particular, the present invention provides polypeptides comprising the amino acid sequence of residues $n^5$–162 of FIGS. 2A and 2B (SEQ ID NO:4), where $n^5$ is an integer in the range of 1 to 156, and 157 is the position of the first residue from the N-terminus of the predicted extracellular domain of the TR11SV1 polypeptide believed to be required for at least immunogenic activity of the predicted extracellular domain of the TR11SV1 protein.

More in particular, the invention provides polynucleotides encoding polypeptides comprising, or alternatively consisting of, the amino acid sequence of residues of M-1 to P-162; A-2 to P-162; P-3 to P-162; G-4 to P-162; E-5 to P-162; R-6 to P-162; D-7 to P-162; S-8 to P-162; W-9 to P-162; I-10 to P-162; N-11 to P-162; P-12 to P-162; G-13 to P-162; P-14 to P-162; D-15 to P-162; S-16 to P-162; Q-17 to P-162; P-18 to P-162; G-19 to P-162; A-20 to P-162; L-21 to P-162; C-22 to P-162; S-23 to P-162; L-24 to P-162; E-25 to P-162; P-26 to P-162; T-27 to P-162; V-28 to P-162; G-29 to P-162; G-30 to P-162; E-31 to P-162; R-32 to P-162; T-33 to P-162; T-34 to P-162; S-35 to P-162; L-36 to P-162; P-37 to P-162; W-38 to P-162; R-39 to P-162; A-40 to P-162; E-41 to P-162; G-42 to P-162; R-43 to P-162; P-44 to P-162; G-45 to P-162; E-46 to P-162; E-47 to P-162; G-48 to P-162; A-49 to P-162; S-50 to P-162; A-51 to P-162; Q-52 to P-162; L-53 to P-162; L-54 to P-162; G-55 to P-162; G-56 to P-162; W-57 to P-162; P-58 to P-162; V-59 to P-162; S-60 to P-162; C-61 to P-162; P-62 to P-162; G-63 to P-162; E-64 to P-162; E-65 to P-162; C-66 to P-162; C-67 to P-162; S-68 to P-162; E-69 to P-162; W-70 to P-162; D-71 to P-162; C-72 to P-162; M-73 to P-162; C-74 to P-162; V-75 to P-162; Q-76 to P-162; P-77 to P-162; E-78 to P-162; F-79 to P-162; H-80 to P-162; C-81 to P-162; G-82 to P-162; D-83 to P-162; P-84 to P-162; C-85 to P-162; C-86 to P-162; T-87 to P-162; T-88 to P-162; C-89 to P-162; R-90 to P-162; H-91 to P-162; H-92 to P-162; P-93 to P-162; C-94 to P-162; P-95 to P-162; P-96 to P-162; G-97 to P-162; Q-98 to P-162; G-99 to P-162; V-100 to P-162; Q-101 to P-162; S-102 to P-162; Q-103 to P-162; G-104 to P-162; K-105 to P-162; F-106 to P-162; S-107 to P-162; F-108 to P-162; G-109 to P-162; F-110 to P-162; Q-111 to P-162; C-112 to P-162; I-113 to P-162; D-114 to P-162; C-115 to P-162; A-116 to P-162; S-117 to P-162; G-118 to P-162; T-119 to P-162; F-120 to P-162; S-121 to P-162; G-122 to P-162; G-123 to P-162; H-124 to P-162; E-125 to P-162; G-126 to P-162; H-127 to P-162; C-128 to P-162; K-129 to P-162; P-130 to P-162; W-131 to P-162; T-132 to P-162; D-133 to P-162; C-134 to P-162; T-135 to P-162; Q-136 to P-162; F-137 to P-162; G-138 to P-162; F-139 to P-162; L-140 to P-162; T-141 to P-162; V-142 to P-162; F-143 to P-162; P-144 to P-162; G-145 to P-162; N-146 to P-162; K-147 to P-162; T-148 to P-162; H-149 to P-162; N-150 to P-162; A-151 to P-162; V-152 to P-162; C-153 to P-162; V-154 to P-162; P-155 to P-162; and G-156 to P-162 of the TR11SV1 amino acid sequence shown in FIGS. 2A and 2B (SEQ ID NO:4). Polynucleotides encoding these polypeptides are also encompassed by the invention.

The present invention further provides polypeptides having one or more residues deleted from the carboxy terminus of the predicted extracellular domain of the amino acid sequence of the TR11SV1 shown in FIGS. 2A and 2B (SEQ ID NO:4), up to the arginine residue at position number 6, and polynucleotides encoding such polypeptides. In particular, the present invention provides polypeptides comprising the amino acid sequence of residues 1–m$^5$ of FIGS. 2A and 2B (SEQ ID NO:4), where m$^5$ is an integer in the range of 6 to 162, and 6 is the position of the first residue from the C-terminus of the predicted extracellular domain of the TR11SV1 polypeptide believed to be required for at least immunogenic activity of the TR11SV1 protein.

More in particular, the invention provides polynucleotides encoding polypeptides comprising, or alternatively consisting of, the amino acid sequence of residues M-1 to P-162; M-1 to E-161; M-1 to A-160; M-1 to P-159; M-1 to P-158; M-1 to S-157; M-1 to G-156; M-1 to P-155; M-1 to V-154; M-1 to C-153; M-1 to V-152; M-1 to A-151; M-1 to N-150; M-1 to H-149; M-1 to T-148; M-1 to K-147; M-1 to N-146; M-1 to G-145; M-1 to P-144; M-1 to F-143; M-1 to V-142; M-1 to T-141; M-1 to L-140; M-1 to F-139; M-1 to G-138; M-1 to F-137; M-1 to Q-136; M-1 to T-135; M-1 to C-134; M-1 to D-133; M-1 to T-132; M-1 to W-131; M-1 to P-130; M-1 to K-129; M-1 to C-128; M-1 to H-127; M-1 to G-126; M-1 to E-125; M-1 to H-124; M-1 to G-123; M-1 to G-122; M-1 to S-121; M-1 to F-120; M-1 to T-119; M-1 to G-118; M-1 to S-117; M-1 to A-116; M-1 to C-115; M-1 to D-114; M-1 to I-113; M-1 to C-112; M-1 to Q-111; M-1 to F-110; M-1 to G-109; M-1 to F-108; M-1 to S-107; M-1 to F-106; M-1 to K-105; M-1 to G-104; M-1 to Q-103; M-1 to S-102; M-1 to Q-101; M-1 to V-100; M-1 to G-99; M-1 to Q-98; M-1 to G-97; M-1 to P-96; M-1 to P-95; M-1 to C-94; M-1 to P-93; M-1 to H-92; M-1 to H-91; M-1 to R-90; M-1 to C-89; M-1 to T-88; M-1 to T-87; M-1 to C-86; M-1 to C-85; M-1 to P-84; M-1 to D-83; M-1 to G-82; M-1 to C-81; M-1 to H-80; M-1 to F-79; M-1 to E-78; M-1 to P-77; M-1 to Q-76; M-1 to V-75; M-1 to C-74; M-1 to M-73; M-1 to C-72; M-1 to D-71; M-1 to W-70; M-1 to E-69; M-1 to S-68; M-1 to C-67; M-1 to C-66; M-1 to E-65; M-1 to E-64; M-1 to G-63; M-1 to P-62; M-1 to C-61; M-1 to S-60; M-1 to V-59; M-1 to P-58; M-1 to W-57; M-1 to G-56; M-1 to G-55; M-1 to L-54; M-1 to L-53; M-1 to Q-52; M-1 to A-51; M-1 to S-50; M-1 to A-49; M-1 to G-48; M-1 to E-47; M-1 to E-46; M-1 to G-45; M-1 to P-44; M-1 to R-43; M-1 to G-42; M-1 to E-41; M-1 to A-40; M-1 to R-39; M-1 to W-38; M-1 to P-37; M-1 to L-36; M-1 to S-35; M-1 to T-34; M-1 to T-33; M-1 to R-32; M-1 to E-31; M-1 to G-30; M-1 to G-29; M-1 to V-28; M-1 to T-27; M-1 to P-26; M-1 to E-25; M-1 to L-24; M-1 to S-23; M-1 to C-22; M-1 to L-21; M-1 to A-20; M-1 to G-19; M-1 to P-18; M-1 to Q-17; M-1 to S-16; M-1 to D-15; M-1 to P-14; M-1 to G-13; M-1 to P-12; M-1 to N-11; M-1 to 1-10; M-1 to W-9; M-1 to D-7; and M-1 to R-6 of the sequence of the TR11SV1 sequence shown in FIGS. 2A and 2B (SEQ ID NO:4). Polynucleotides encoding these polypeptides also are provided.

The invention also provides polypeptides having one or more amino acids deleted from both the amino and the carboxyl termini of a soluble TR11SV1 polypeptide, which may be described generally as having residues n$^5$–m$^5$ of FIGS. 2A and 2B (SEQ ID NO:4), where n$^5$ and m$^5$ are integers as described above.

In addition, the present invention further provides polypeptides having one or more residues deleted from the amino terminus of the predicted extracellular domain of the TR11SV2 amino acid sequence shown in FIGS. 3A and 3B (SEQ ID NO:6), up to the glycine residue at position number 162 and polynucleotides encoding such polypeptides. In particular, the present invention provides polypeptides comprising the amino acid sequence of residues n$^5$–168 of FIGS. 3A and 3B (SEQ ID NO:6), where n$^6$ is an integer in the range of 20 to 162, and 163 is the position of the first residue from the N-terminus of the predicted extracellular domain of the TR11SV2 polypeptide believed to be required for at least immunogenic activity of the predicted extracellular domain of the TR11SV2 protein.

More in particular, the invention provides polynucleotides encoding polypeptides comprising, or alternatively consisting of, the amino acid sequence of residues of Q-20 to P-168; R-21 to P-168; P-22 to P-168; T-23 to P-168; G-24 to P-168; G-25 to P-168; P-26 to P-168; G-27 to P-168; C-28 to P-168; G-29 to P-168; P-30 to P-168; G-31 to P-168; R-32 to P-168; L-33 to P-168; L-34 to P-168; L-35 to P-168; G-36 to P-168; T-37 to P-168; G-38 to P-168; T-39 to P-168; D-40 to P-168; A-41 to P-168; R-42 to P-168; C-43 to P-168; C-44 to P-168; R-45 to P-168; V-46 to P-168; H-47 to P-168; T-48 to P-168; T-49 to P-168; R-50 to P-168; C-51 to P-168; C-52 to P-168; R-53 to P-168; D-54 to P-168; Y-55 to P-168; P-56 to P-168; A-57 to P-168; Q-58 to P-168; L-59 to P-168; L-60 to P-168; G-61 to P-168; G-62 to P-168; W-63 to P-168; P-64 to P-168; V-65 to P-168; S-66 to P-168; C-67 to P-168; P-68 to P-168; G-69 to P-168; E-70 to P-168; E-71 to P-168; C-72 to P-168; C-73 to P-168; S-74 to P-168; E-75 to P-168; W-76 to P-168; D-77 to P-168; C-78 to P-168; M-79 to P-168; C-80 to P-168; V-81 to P-168; Q-82 to P-168; P-83 to P-168; E-84 to P-168; F-85 to P-168; H-86 to P-168; C-87 to P-168; G-88 to P-168; D-89 to P-168; P-90 to P-168; C-91 to P-168; C-92 to P-168; T-93 to P-168; T-94 to P-168; C-95 to P-168; R-96 to P-168; H-97 to P-168; H-98 to P-168; P-99 to P-168; C-100 to P-168; P-100 to P-168; P-102 to P-168; G-103 to P-168; Q-104 to P-168; G-105 to P-168; V-106 to P-168; Q-107 to P-168; S-108 to P-168; Q-109 to P-168; G-110 to P-168; K-111 to P-168; F-112 to P-168; S-113 to P-168; F-114 to P-168; G-115 to P-168; F-116 to P-168; Q-117 to P-168; C-118 to P-168; I-119 to P-168; D-120 to P-168; C-121 to P-168; A-122 to P-168; S-123 to P-168; G-124 to P-168; T-125 to P-168; F-126 to P-168; S-127 to P-168; G-128 to P-168; G-129 to P-168; H-130 to P-168; E-131 to P-168; G-132 to P-168; H-133 to P-168; C-134 to P-168; K-135 to P-168; P-136 to P-168; W-137 to P-168; T-138 to P-168; D-139 to P-168; C-140 to P-168; T-141 to P-168; Q-142 to P-168; F-143 to P-168; G-144 to P-168; F-145 to P-168; L-146 to P-168; T-147 to P-168; V-148 to P-168; F-149 to P-168; P-150 to P-168; G-151 to P-168; N-152 to P-168; K-153 to P-168; T-154 to P-168; H-155 to P-168; N-156 to P-168; A-157 to P-168; V-158 to P-168; C-159 to P-168; V-160 to P-168; P-161 to P-168; and G-162 to P-168 of the TR11SV2 amino acid sequence shown in FIGS. 3A and 3B (which is identical to the sequence shown as SEQ ID NO:6, with the exception that the amino acid residues in FIGS. 3A and 3B are numbered consecutively from 1 through 240 from the N-terminus to the C-terminus, while the amino acid residues in SEQ ID NO:6 are numbered consecutively from −19 through 221 to reflect the position of the predicted signal peptide). Polynucleotides encoding these polypeptides are also encompassed by the invention.

The present invention further provides polypeptides having one or more residues deleted from the carboxy terminus of the predicted extracellular domain of the amino acid sequence of the TR11SV2 shown in FIGS. 3A and 3B (SEQ ID NO:6), up to the proline residue at position number 26, and polynucleotides encoding such polypeptides. In particular, the present invention provides polypeptides comprising the amino acid sequence of residues 20–$m^6$ of FIGS. 3A and 3B (SEQ ID NO:6), where $m^6$ is an integer in the range of 26 to 168, and 26 is the position of the first residue from the C-terminus of the predicted extracellular domain of the TR11SV2 polypeptide believed to be required for at least immunogenic activity of the TR11SV2 protein.

More in particular, the invention provides polynucleotides encoding polypeptides comprising, or alternatively consisting of, the amino acid sequence of residues Q-20 to P-168; Q-20 to E-167; Q-20 to A-166; Q-20 to P-165; Q-20 to P-164; Q-20 to S-163; Q-20 to G-162; Q-20 to P-161; Q-20 to V-160; Q-20 to C-159; Q-20 to V-158; Q-20 to A-157; Q-20 to N-156; Q-20 to H-155; Q-20 to T-154; Q-20 to K-153; Q-20 to N-152; Q-20 to G-151; Q-20 to P-150; Q-20 to F-149; Q-20 to V-148; Q-20 to T-147; Q-20 to L-146; Q-20 to F-145; Q-20 to G-144; Q-20 to F-143; Q-20 to Q-142; Q-20 to T-141; Q-20 to C-140; Q-20 to D-139; Q-20 to T-138; Q-20 to W-137; Q-20 to P-136; Q-20 to K-135; Q-20 to C-134; Q-20 to H-133; Q-20 to G-132; Q-20 to E-131; Q-20 to H-130; Q-20 to G-129; Q-20 to G-128; Q-20 to S-127; Q-20 to F-126; Q-20 to T-125; Q-20 to G-124; Q-20 to S-123; Q-20 to A-122; Q-20 to C-121; Q-20 to D-120; Q-20 to I-119; Q-20 to C-118; Q-20 to Q-117; Q-20 to F-116; Q-20 to G-115; Q-20 to F-114; Q-20 to S-113; Q-20 to F-112; Q-20 to K-111; Q-20 to G-110; Q-20 to Q-109; Q-20 to S-108; Q-20 to Q-107; Q-20 to V-106; Q-20 to G-105; Q-20 to Q-104; Q-20 to G-103; Q-20 to P-102; Q-20 to P-101; Q-20 to C-100; Q-20 to P-99; Q-20 to H-98; Q-20 to H-97; Q-20 to R-96; Q-20 to C-95; Q-20 to T-94; Q-20 to T-93; Q-20 to C-92; Q-20 to C-91; Q-20 to P-90; Q-20 to D-89; Q-20 to G-88; Q-20 to C-87; Q-20 to H-86; Q-20 to F-85; Q-20 to E-84; Q-20 to P-83; Q-20 to Q-82; Q-20 to V-81; Q-20 to C-80; Q-20 to M-79; Q-20 to C-78; Q-20 to D-77; Q-20 to W-76; Q-20 to E-75; Q-20 to S-74; Q-20 to C-73; Q-20 to C-72; Q-20 to E-71; Q-20 to E-70; Q-20 to G-69; Q-20 to P-68; Q-20 to C-67; Q-20 to S-66; Q-20 to V-65; Q-20 to P-64; Q-20 to W-63; Q-20 to G-62; Q-20 to G-61; Q-20 to L-60; Q-20 to L-59; Q-20 to Q-58; Q-20 to A-57; Q-20 to P-56; Q-20 to Y-55; Q-20 to D-54; Q-20 to R-53; Q-20 to C-52; Q-20 to C-51; Q-20 to R-50; Q-20 to T-49; Q-20 to T-48; Q-20 to H-47; Q-20 to V-46; Q-20 to R-45; Q-20 to C-44; Q-20 to C-43; Q-20 to R-42; Q-20 to A-41; Q-20 to D-40; Q-20 to T-39; Q-20 to G-38; Q-20 to T-37; Q-20 to G-36; Q-20 to L-35; Q-20 to L-34; Q-20 to L-33; Q-20 to R-32; Q-20 to G-31; Q-20 to P-30; Q-20 to G-29; Q-20 to C-28; Q-20 to G-27; Q-20 to P-26; and Q20 to P-26 of the sequence of the TR11SV2 sequence shown in FIGS. 3A and 3B (which is identical to the sequence shown as SEQ ID NO:6, with the exception that the amino acid residues in FIGS. 3A and 3B are numbered consecutively from 1 through 240 from the N-terminus to the C-terminus, while the amino acid residues in SEQ ID NO:6 are numbered consecutively from −19 through 221 to reflect the position of the predicted signal peptide). Polynucleotides encoding these polypeptides also are provided.

The invention also provides polypeptides having one or more amino acids deleted from both the amino and the carboxyl termini of a TR11SV2 polypeptide, which may be described generally as having residues $n^6$–$m^6$ of FIGS. 3A and 3B (SEQ ID NO:6), where $n^6$ and $m^6$ are integers as described above.

The polypeptides of this invention may be membrane bound or may be in a soluble circulating form. Soluble peptides are defined by amino acid sequence wherein the sequence comprises the polypeptide sequence lacking the transmembrane domain.

The polypeptides of the present invention may exist as a membrane bound receptor having a transmembrane region and an intra- and extracellular region or they may exist in soluble form wherein the transmembrane domain is lacking. One example of such a form of the TR11, TR11SV1, and TR11SV2 receptors is the TR11, TR11SV1, and TR11SV2 receptors shown in FIGS. 1A and 1B, 2A and 2B, and 3A and 3B (SEQ ID NO:2, SEQ ID NO:4, and SEQ ID NO:6, respectively) which contain transmembrane, intracellular and extracellular domains. Thus, these forms of the TR11, TR11SV1, and TR11SV2 receptors appear to be localized in the cytoplasmic membrane of cells which express these proteins.

It will be recognized in the art that some amino acid sequences of the TR11, TR11SV1, and TR11SV2 receptors can be varied without significant effect to the structure or function of the protein. If such differences in sequence are contemplated, it should be remembered that there will be critical areas on the protein which determine activity. Thus, the invention further includes variations of the TR11, TR11SV1, and TR11SV2 receptors which show substantial TR11, TR11SV1 or TR11SV2 receptor activities or which include regions of TR11, TR11SV1, and TR11SV2 proteins such as the protein portions discussed below. Such mutants include deletions, insertions, inversions, repeats, and type substitutions. As indicated above, guidance concerning which amino acid changes are likely to be phenotypically silent can be found in the publication authored by Bowie and coworkers ("Deciphering the Message in Protein Sequences: Tolerance to Amino Acid Substitutions," *Science* 247:1306–1310 (1990)).

Thus, the fragments, derivatives or analogs of the polypeptides of FIGS. 1A and 1B, 2A and 2B, and 3A and 3B (SEQ ID NO:2, SEQ ID NO:4, and SEQ ID NO:6, respectively), or those encoded by the deposited cDNAs, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the TR11, TR11SV1 or TR11SV2 proteins. The prevention of aggregation is highly desirable. Aggregation of proteins not only results in a loss of activity but can also be problematic when preparing pharmaceutical formulations, because they can be immunogenic (Pinckard, et al., *Clin Exp. Immunol.* 2:331–340 (1967); Robbins, et al., *Diabetes* 36:838–845 (1987); Cleland, et al. *Crit. Rev. Therapeutic Drug Carrier Systems* 10:307–377 (1993)).

The replacement of amino acids can also change the selectivity of binding to cell surface receptors. Ostade and colleagues (*Nature* 361:266–268 (1993)) describe certain mutations resulting in selective binding of TNF-α to only one of the two previously described types of TNF receptors. Thus, the TR11, TR11SV1, and TR11SV2 receptors of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table I).

TABLE I

CONSERVATIVE AMINO ACID SUBSTITUTIONS.

| | |
|---|---|
| Aromatic | Phenylalanine |
| | Tryptophan |
| | Tyrosine |
| Hydrophobic | Leucine |

TABLE I-continued

CONSERVATIVE AMINO ACID SUBSTITUTIONS.

| | |
|---|---|
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Embodiments of the invention are directed to polypeptides which comprise the amino acid sequence of a TR11, TR11SV1, and/or TR11SV2 polypeptide described herein, but having an amino acid sequence which contains at least one conservative amino acid substitution, but not more than 50 conservative amino acid substitutions, even more preferably, not more than 40 conservative amino acid substitutions, still more preferably, not more than 30 conservative amino acid substitutions, and still even more preferably, not more than 20 conservative amino acid substitutions, when compared with the TR11, TR11SV1, and/or TR11SV2 polynucleotide sequence described herein. Of course, in order of ever-increasing preference, it is highly preferable for a peptide or polypeptide to have an amino acid sequence which comprises the amino acid sequence of a TR11, TR11SV1, and/or TR11SV2 polypeptide, which contains at least one, but not more than 10, 9, 8, 7, 6, 5, 4, 3, 2 or 1 conservative amino acid substitutions.

Amino acids in the TR11, TR11SV1 and TR11SV2 proteins of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

The polypeptides of the present invention are preferably provided in an isolated form. By "isolated polypeptide", is intended a polypeptide removed from its native environment. Thus, a polypeptide produced and contained within a recombinant host cell would be considered "isolated" for purposes of the present invention. Also intended as an "isolated polypeptide" are polypeptides that have been purified, partially or substantially, from a recombinant host. For example, recombinantly produced versions of the TR11, TR11SV1, and TR11SV2 receptors can be substantially purified by the one-step method described in Smith and Johnson, *Gene* 67: 31–40 (1988).

The polypeptides of the present invention also include: (a) the TR11 polypeptide encoded by the deposited cDNA including the leader; (b) the TR11SV1 polypeptide encoded by the deposited cDNA including the leader; (c) the TR11SV2 polypeptide encoded by the deposited cDNA including the leader; (d) the TR11 polypeptide encoded by the deposited the cDNA minus the leader (i.e., the mature protein); (e) the TR11SV1 polypeptide encoded by the deposited the cDNA minus the leader (i.e., the mature protein); (f) the TR11SV2 polypeptide encoded by the deposited the cDNA minus the leader (i.e., the mature protein); (g) the TR11 polypeptide of FIGS. 1A and 1B (SEQ ID NO:2) including the leader; (h) the TR11SV1 polypeptide of FIGS. 2A and 2B (SEQ ID NO:4) including the leader; (i) the TR11SV2 polypeptide of FIGS. 3A and 3B (SEQ ID NO:6) including the leader; (j) the TR11 polypeptide of FIGS. 1A and 1B (SEQ ID NO:2) including the leader but minus the N-terminal methionine; (k) the TR11SV1 polypeptide of FIGS. 2A and 2B (SEQ ID NO:4) including the leader but minus the N-terminal methionine; (l) the TR11SV2 polypeptide of FIGS. 3A and 3B (SEQ ID NO:6) including the leader but minus the N-terminal methionine; (m) the polypeptide of FIGS. 1A and 1B (SEQ ID NO:2) minus the leader; (n) the polypeptide of FIGS. 2A and 2B (SEQ ID NO:4) minus the leader; (o) the polypeptide of FIGS. 3A and 3B (SEQ ID NO:6) minus the leader; (p) the extracellular domain, the transmembrane domain, and the intracellular domain of the TR11 receptor shown in FIGS. 1A and 1B (SEQ ID NO:2); (q) the extracellular domain, the transmembrane domain, and the intracellular domain of the TR11SV1 receptor shown in FIGS. 2A and 2B (SEQ ID NO:4); (r) the extracellular domain, the transmembrane domain, and the intracellular domain of the TR11SV2 receptor shown in FIGS. 3A and 3B (SEQ ID NO:6); and polypeptides which are at least 80% identical, more preferably at least 90% or 95% identical, still more preferably at least 96%, 97%, 98% or 99% identical to the polypeptides described above, and also include portions of such polypeptides with at least 30 amino acids and more preferably at least 50 amino acids.

By a polypeptide having an amino acid sequence at least, for example, 95% "identical" to a reference amino acid sequence of a TR11, TR11SV1 or TR11SV2 polypeptide is intended that the amino acid sequence of the polypeptide is identical to the reference sequence except that the polypeptide sequence may include up to five amino acid alterations per each 100 amino acids of the reference amino acid of a TR11, TR11SV1 or TR11SV2 receptor. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIGS. 1A and 1B (SEQ ID NO:2), FIGS. 2A and 2B (SEQ ID NO:4), and/or FIGS. 3A and 3B (SEQ ID NO:6), the amino acid sequence encoded by deposited cDNA clones HHEAC71, HT5EA78, and HCFAZ22, respectively, or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag and colleagues (*Comp. App. Biosci.* 6:237–245 (1990)). Preferred parameters used in a FASTDB amino acid alignment are: Matrix= PAM 0, k-tuple=2, Mismatch Penalty=1, Joining Penalty= 20, Randomization. Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The polypeptides of the present invention could be used as a molecular weight marker on SDS-PAGE gels or on molecular sieve gel filtration columns using methods well known to those of skill in the art.

In another aspect, the invention provides peptides or polypeptides comprising epitope-bearing portions of the polypeptides of the invention. The epitopes of these polypeptide portions are an immunogenic or antigenic epitopes of the polypeptides described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. Science 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777. Antigenic epitope-bearing peptides and polypeptides of the invention preferably contain a sequence of at least seven, more preferably at least nine and most preferably between at least about 15 to about 30 amino acids contained within the amino acid sequence of a polypeptide of the invention.

Non-limiting examples of antigenic polypeptides or peptides that can be used to generate TR11 receptor-specific antibodies include: a polypeptide comprising amino acid residues from about Arg-2 to about Pro-11 in SEQ ID NO:2; a polypeptide comprising amino acid residues from about Thr-18 to about Arg-26 in SEQ ID NO:2; a polypeptide comprising amino acid residues from about Arg-34 to about Cys-42 in SEQ ID NO:2; a polypeptide comprising amino acid residues from about Arg-31 to about Glu-39 in SEQ ID NO:2; a polypeptide comprising amino acid residues from about Gly-38 to about Asp-46 in SEQ ID NO:2; a polypeptide comprising amino acid residues from about Gly-74 to about Ser-82 in SEQ ID NO:2; a polypeptide comprising amino acid residues from about Glu-100 to about Asp-108 in SEQ ID NO:2; a polypeptide comprising amino acid residues from about Phe-118 to about Ala-126 in SEQ ID NO:2; a polypeptide comprising amino acid residues from about Gly-131 to about Gly-139 in SEQ ID NO:2; a polypeptide comprising amino acid residues from about Pro-178 to about Cys-186 in SEQ ID NO:2; and a polypeptide comprising amino acid residues from about Ser-197 to about Gly-205 in SEQ ID NO:2. As indicated above, the inventors have determined that the above polypeptide fragments are antigenic regions of the TR11 receptor proteins.

Non-limiting examples of antigenic polypeptides or peptides that can be used to generate TR11SV1 receptor-specific antibodies include: a polypeptide comprising amino acid residues from about Ala-2 to about Ile-10 in SEQ ID NO:4; a polypeptide comprising amino acid residues from about Asn-11 to about Gly-19 in SEQ ID NO:4; a polypeptide comprising amino acid residues from about Thr-27 to about Ser-35 in SEQ ID NO:4; a polypeptide comprising amino acid residues from about Trp-38 to about Glu-46 in SEQ ID NO:4; a polypeptide comprising amino acid residues from about Gly-42 to about Ser-50 in SEQ ID NO:4; a polypeptide comprising amino acid residues from about Glu-31 to about Glu-46 in SEQ ID NO:4; a polypeptide comprising amino acid residues from about. Cys-61 to about Glu-69 in SEQ ID NO:4; a polypeptide comprising amino acid residues from about Gly-99 to about Ser-107 in SEQ ID NO:4; a polypeptide comprising amino acid residues from about Glu-125 to about Asp-133 in SEQ ID NO:4; a polypeptide comprising amino acid residues from about Phe-143 to about Ala-151 in SEQ ID NO:4; a polypeptide comprising amino acid residues from about Gly-156 to about Gly-164 in SEQ ID NO:4; a polypeptide comprising amino acid residues from about Cys-196 to about Leu-204 in SEQ ID NO:4; a polypeptide comprising amino acid residues from about Pro-209 to about Ser-217 in SEQ ID NO:4; and a polypeptide comprising amino acid residues from about Ser-229 to about Gly-237 in SEQ ID NO:4. As indicated above, the inventors have determined that the above polypeptide fragments are antigenic regions of the TR11SV1 receptor proteins.

Non-limiting examples of antigenic polypeptides or peptides that can be used to generate TR11SV2 receptor-specific antibodies include: a polypeptide comprising amino acid residues from about Gln-1 to about Cys-9 in SEQ ID NO:6; a polypeptide comprising amino acid residues from about Gly-5 to about Arg-13 in SEQ ID NO:6; a polypeptide comprising amino acid residues from about Thr-18 to about Arg-26 in SEQ ID NO:6; a polypeptide comprising amino acid residues from about Thr-29 to about Pro-37 in SEQ ID NO:6; a polypeptide comprising amino acid residues from about Cys-48 to about Glu-56 in SEQ ID NO:6; a polypeptide comprising amino acid residues from about Val-87 to about Phe-95 in SEQ ID NO:6; a polypeptide comprising amino acid residues from about His-111 to about Thr-119 in SEQ ID NO:6; a polypeptide comprising amino acid residues from about Phe-130 to about Ala-138 in SEQ ID NO:6; a polypeptide comprising amino acid residues from about Gly-143 to about Gly-151 in SEQ ID NO:6; a polypeptide comprising amino acid residues from about Pro-190 to about Cys-198 in SEQ ID NO:6; and a polypeptide comprising amino acid residues from about Ser-209 to about Gly-217 in SEQ ID NO:6. As indicated above, the inventors have determined that the above polypeptide fragments are antigenic regions of the TR11SV2 receptor proteins.

The epitope-bearing peptides and polypeptides of the invention may be produced by any conventional means. Houghten, R. A. (1985) General method for the rapid solid-phase synthesis of large numbers of peptides: specificity of antigen-antibody interaction at the level of individual amino acids. *Proc. Natl. Acad. Sci. USA* 82:5131–5135. This "Simultaneous Multiple Peptide Synthesis (SMPS)" process is further described in U.S. Pat. No. 4,631,211 to Houghten et al. (1986).

As one of skill in the art will appreciate, TR11, TR11SV1, and TR11SV2 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394, 827; Traunecker et al., *Nature* 331:84–86 (1988)). Fusion proteins that have a disulfide-linked dimeric structure due to the IgG part can also be more efficient in binding and neutralizing other molecules than the monomeric TR11, TR11SV1, and TR11SV2 receptor proteins or protein fragments alone (Fountoulakis et al., *J Biochem* 270:3958–3964 (1995)).

Detection of Disease States

The TNF-family ligands induce various cellular responses by binding to TNF-family receptors, including the TR11, TR11SV1, and TR11SV2 receptors of the present invention. TNF-β, a potent ligand of the TNF receptor proteins, is known to be involved in a number of biological processes including lymphocyte development, tumor necrosis, induction of an antiviral state, activation of polymorphonuclear leukocytes, induction of class I major histocompatibility complex antigens on endothelial cells, induction of adhesion molecules on endothelium and growth hormone stimulation (Ruddle and Homer, *Prog. Allergy*, 40:162–182 (1988)). TNF-α, also a ligand of the TNF receptor proteins, has been reported to have a role in the rapid necrosis of tumors, immunostimulation, autoimmnune disease, graft rejection, producing an anti-viral response, septic shock, cerebral malaria, cytotoxicity, protection against deleterious effects of ionizing radiation produced during a course of chemotherapy, such as denaturation of enzymes, lipid peroxidation and DNA damage (Nata et al, *J. Immunol.* 136(7) :2483 (1987); Porter, Tibtech 9:158–162 (1991)), growth regulation, vascular endothelium effects and metabolic effects. TNF-α also triggers endothelial cells to secrete various factors, including PAI-1, IL-1, GM-CSF and IL-6 to promote cell proliferation. In addition, TNF-α up-regulates various cell adhesion molecules such as E-Selectin, ICAM-1 and VCAM-1. TNF-α and the Fas ligand have also been shown to induce programmed cell death. TRAIL (also known as Apo-2L) is a member of the tumor necrosis factor (TNF) ligand family that rapidly induces apoptosis in a variety of transformed cell lines. The human receptor for TRAIL was found to be an undescribed member of the TNF receptor family designated death receptor (DR)-4 (Pan, G., et al., *Science* 276:111–113 (1997)).

Cells which express the, TR11, TR11SV1 or TR11SV2 polypeptides and are believed to have a potent cellular response to TR11, TR11SV1 or TR11SV2 receptor ligands include activated T-cells. By "a cellular response to a TNF-family ligand" is intended any genotypic, phenotypic, and/or morphologic change to a cell, cell line, tissue, tissue culture or patient that is induced by a TNF-family ligand. As indicated, such cellular responses include not only normal physiological responses to TNF-family ligands, but also diseases associated with increased cell proliferation or the inhibition of increased cell proliferation, such as by the inhibition of apoptosis. Apoptosis-programmed cell death-is a physiological mechanism involved in the deletion of peripheral T-lymphocytes of the immune system, and its dysregulation can lead to a number of different pathogenic processes (Ameisen, J. C., *AIDS* 8:1197–1213 (1994); Krammer, P. H. et al., *Curr. Opin. Immunol.* 6:279–289 (1994)).

It is believed that certain tissues in mammals with specific disease states associated with aberrant cell survival express significantly altered levels of the TR11, TR11SV1, and TR11SV2 receptor proteins and mRNAs encoding the TR11, TR11SV1, and TR11SV2 receptor proteins when compared to a corresponding "standard" mammal, i.e., a mammal of the same species not having the disease state. Further, since some forms of these proteins are secreted, it is believed that enhanced levels of the TR11, TR11SV1 or TR11SV2 receptor proteins can be detected in certain body fluids (e.g., sera, plasma, urine, and spinal fluid) from mammals with the disease state when compared to sera from mammals of the same species not having the disease state. Thus, the invention provides a diagnostic method useful during diagnosis of disease states, which involves assaying the expression level of the gene encoding the TR11, TR11SV1, and TR11SV2 receptor proteins in mammalian cells or body fluid and comparing the gene expression level with a standard TR11, TR11SV1, and TR11SV2 receptor gene expression levels, whereby an increase or decrease in the gene expression level over the standard is indicative of certain disease states associated with aberrant cell survival.

Where diagnosis of a disease state involving the TR11, TR11SV1 or TR11SV2 receptors of the present invention has already been made according to conventional methods, the present invention is useful as a prognostic indicator, whereby patients exhibiting significantly aberrant TR11, TR11SV1 or TR11SV2 receptor gene expression will experience a worse clinical outcome relative to patients expressing the gene at a lower level.

By "assaying the expression level of the gene encoding the TR11, TR11SV1 or TR11SV2 receptor protein" is intended qualitatively or quantitatively measuring or estimating the level of the TR11, TR11SV1 or TR11SV2 receptor protein or the level of the mRNA encoding the TR11, TR11SV1 or TR11SV2 receptor protein in a first biological sample either directly (e.g., by determining or estimating absolute protein level or mRNA level) or relatively (e.g., by comparing to the TR11, TR11SV1 or TR11SV2 receptor protein level or mRNA level in a second biological sample).

Preferably, the TR11, TR11SV1 or TR11SV2 receptor protein levels or mRNA levels in the first biological sample is measured or estimated and compared to a standard TR11, TR11SV1 or TR11SV2 receptor protein level or mRNA level, the standard being taken from a second biological sample obtained from an individual not having the disease state. As will be appreciated in the art, once a standard TR11, TR11SV1 or TR11SV2 receptor protein level or mRNA level is known, it can be used repeatedly as a standard for comparison.

By "biological sample" is intended any biological sample obtained from an individual, cell line, tissue culture, or other source which contains TR11, TR11SV1 or TR11SV2 receptor protein or mRNA. Biological samples include mammalian body fluids (such as sera, plasma, urine, synovial fluid and spinal fluid) which contain secreted mature TR11, TR11SV1 or TR11SV2 receptor protein, and thymus, prostate, heart, placenta, muscle, liver, spleen, lung, kidney and other tissues. Methods for obtaining tissue biopsies and body fluids from mammals are well known in the art. Where the biological sample is to include mRNA, a tissue biopsy is the preferred source.

Diseases associated with increased cell survival, or the inhibition of apoptosis, include cancers (such as follicular lymphomas, carcinomas with p53 mutations, and hormone-dependent tumors); autoimmune disorders (such as systemic lupus erythematosus and immune-related glomerulonephritis rheumatoid arthritis) and viral infections (such as herpes viruses, pox viruses and adenoviruses), information graft v. host disease, acute graft rejection, and chronic graft rejection. Diseases associated with decreased cell survival, or increased apoptosis, include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as a plastic anemia), ischemic injury (such as that caused by myocardial infarction, stroke and reperfusion injury), toxin-induced liver disease (such as that caused by alcohol), septic shock, cachexia and anorexia.

Assays available to detect levels of soluble receptors are well known to those of skill in the art, for example, radioimmunoassays, competitive-binding assays, Western blot analysis, and preferably an ELISA assay may be employed.

TR11, TR11SV1, and TR11SV2 receptor-protein specific antibodies can be raised against the intact TR11, TR11SV1, and TR11SV2 receptor proteins or antigenic polypeptide fragments thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (mAb) is meant to include intact molecules as well as antibody fragments (such as, for example, Fab and F(ab') fragments) which are capable of specifically binding to TR11, TR11SV1 or TR11SV2 receptor proteins. Fab and F(ab') fragments lack the Fc fragment of intact antibody, clear more rapidly from the circulation, and may have less non-specific tissue binding of an intact antibody (Wahl et al., *J. Nucl. Med.* 24:316–325 (1983)). Thus, these fragments are preferred.

The antibodies of the present invention may be prepared by any of a variety of methods. For example, cells expressing the TR11, TR11SV1 or TR11SV2 receptor proteins or antigenic fragments thereof can be administered to an animal in order to induce the production of sera containing polyclonal antibodies. In a preferred method, a preparation of TR11, TR11SV1 or TR11SV2 receptor protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or TR11, TR11SV1 or TR11SV2 receptor protein binding fragments thereof). Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, N.Y., (1981) pp. 563–681). In general, such procedures involve immunizing an animal (preferably a mouse) with a TR11, TR11SV1 or TR11SV2 receptor protein antigen or, more preferably, with a TR11, TR11SV1 or TR11SV2 receptor protein-expressing cell. Suitable cells can be recognized by their capacity to bind anti-TR11, TR11SV1 or TR11SV2 receptor protein antibody. Such cells may be cultured in any suitable tissue culture medium; however, it is preferable to culture cells in Earle's modified Eagle's medium supplemented with 10% fetal bovine serum (inactivated at about 56 C), and supplemented with about 10 g/l of nonessential amino acids, about 1,000 U/ml of penicillin, and about 100 µg/ml of streptomycin. The splenocytes of such mice are extracted and fused with a suitable myeloma cell line. Any suitable myeloma cell line may be employed in accordance with the present invention; however, it is preferable to employ the parent myeloma cell line (SPO), available from the American Type Culture Collection, Rockville, Md. After fusion, the resulting hybridoma cells are selectively maintained in HAT medium, and then cloned by limiting dilution as described by Wands et al. (*Gastroenterology* 80:225–232 (1981)). The hybridoma cells obtained through such a selection are then assayed to identify clones which secrete antibodies capable of binding the TR11, TR11SV1, and TR11SV2 receptor protein antigens.

Agonists and Antagonists of TR11, TR11SV1, and TR11SV2 Receptor Function

In one aspect, the present invention is directed to a method for inhibiting an activity of TR11, TR11SV1 or TR11SV2 induced by a TNF-family ligand (e.g., cell proliferation, hematopoietic development), which involves administering to a cell which expresses a TR11, TR11SV1 or TR11SV2 polypeptide an effective amount of a TR11, TR11SV1 or TR11SV2 receptor ligand, analog or an antagonist capable of decreasing TR11, TR11SV1 or TR11SV2, receptor mediated signaling. Preferably, TR11, TR11SV1 or TR11SV2 receptor mediated signaling is decreased to treat a disease wherein increased cell proliferation is exhibited. An antagonist can include soluble forms of the TR11, TR11SV1 or TR11SV2 receptors and antibodies directed against the TR11, TR11SV1 or TR11SV2 polypeptides which block TR11, TR11SV1 or TR11SV2 receptor mediated signaling. Preferably, TR11, TR11SV1 or TR11SV2 receptor mediated signaling is decreased to treat a disease.

In a further aspect, the present invention is directed to a method for increasing cell proliferation induced by a TNF-family ligand, which involves administering to a cell which expresses a TR11, TR11SV1 or TR11SRV2 polypeptide an effective amount of an agonist capable of increasing TR11, TR11SV1 or TR11SV2 receptor mediated signaling. Preferably, TR11, TR11SV1 or TR11SV2 receptor mediated signaling is increased to treat a disease wherein decreased cell proliferation is exhibited. Agonists of the present invention include monoclonal antibodies directed against the TR11, TR11SV1 or TR11SV2 polypeptides which stimulate TR11, TR11SV1 or TR11SV2 receptor mediated signaling. Preferably, TR11, TR11SV1 or TR11SV2 receptor mediated signaling is increased to treat a disease.

By "agonist" is intended naturally occurring and synthetic compounds capable of enhancing cell proliferation and differentiation mediated by TR11, TR11SV1 or TR11SV2 polypeptides. Such agonists include agents which increase expression of TR11; TR11SV1 or TR11SV2 receptors or increase the sensitivity of the expressed receptor. By "antagonist" is intended naturally occurring and synthetic compounds capable of inhibiting TR11, TR11SV1 or TR11SV2 mediated cell proliferation and differentiation. Such antagonists include agents which decrease expression of TR11, TR11SV1 or TR11SV2 receptors or decrease the sensitivity of the expressed receptor. Whether any candidate "agonist" or "antagonist" of the present invention can enhance or inhibit cell proliferation and differentiation can be determined using art-known TNF-family ligand/receptor cellular response assays, including those described in more detail below.

One such screening technique involves the use of cells which express the receptor (for example, transfected CHO cells) in a system which measures extracellular pH changes caused by receptor activation, for example, as described in *Science* 246:181–296 (October 1989). For example, compounds may be contacted with a cell which expresses the receptor polypeptide of the present invention and a second messenger response, e.g., signal transduction or pH changes, may be measured to determine whether the potential compound activates or inhibits the receptor.

Another such screening technique involves introducing RNA encoding the receptor into Xenopus oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Soluble forms of the polypeptides of the present invention may be utilized in the ligand binding assay described above. These forms of the TR11, TR11SV1, and TR11SV2 receptors are contacted with ligands in the extracellular medium after they are secreted. A determination is then made as to whether the secreted protein will bind to TR11, TR11SV1 or TR11SV2 receptor ligands.

Further screening assays for agonist and antagonist of the present invention are described in Tartaglia, L. A., and Goeddel, D. V., *J. Biol. Chem.* 267(7): 4304–4307(1992).

Thus, in a further aspect, a screening method is provided for determining whether a candidate agonist or antagonist is capable of enhancing or inhibiting a cellular response to a TNF-family ligand. The method involves contacting cells which express TR11, TR11SV1 or TR11SV2 polypeptides with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By "assaying a cellular response" is intended qualitatively or quantitatively measuring a cellular response to a candidate compound and/or a TNF-family ligand (e.g., determining or estimating an increase or decrease in T cell proliferation or tritiated thymidine labeling). By the invention, a cell expressing a TR11, TR11SV1 or TR11SV2 polypeptide can be contacted with either an endogenous or exogenously administered TNF-family ligand.

In an additional aspect, a thymocyte proliferation assay may be employed to identify both ligands and potential drug candidates. For example, thymus cells are disaggregated from tissue and grown in culture medium. Incorporation of DNA precursors such as [$^3$H]-thymidine or 5-bromo-2'-deoxyuridine (BrdU) is monitored as a parameter for DNA synthesis and cellular proliferation. Cells which have incorporated BrdU into DNA can be detected using a monoclonal antibody against BrdU and measured by an enzyme or fluorochrome-conjugated second antibody. The reaction is quantitated by fluorimetry or by spectrophotometry. Two control wells and an experimental well are set up as above and TNF-β or cognate ligand is added to all wells while soluble receptor polypeptides of the present invention are added individually to the second control wells, with the experimental well containing a compound to be screened. The ability of the compound to be screened to stimulate or inhibit the above interaction may then be quantified.

Agonists according to the present invention include compounds such as, for example, TNF-family ligand peptide fragments, transforming growth factors, and neurotransmitters (such as glutamate, dopamine, N-methyl-D-aspartate). Preferred agonists include polyclonal and monoclonal antibodies raised against TR11, TR11SV1 or TR11SV2 polypeptides, or a fragments thereof. Such agonist antibodies raised against a TNF-family receptor are disclosed in Tartaglia, L. A., et al., *Proc. Natl. Acad. Sci. USA* 88:9292–9296 (1991); and Tartaglia, L. A., and Goeddel, D. V., *J. Biol. Chem.* 267 (7):4304–4307 (1992). See, also, PCT Application WO 94/09137. Further preferred agonists include chemotherapeutic drugs such as, for example, cisplatin, doxorubicin, bleomycin, cytosine arabinoside, nitrogen mustard, methotrexate and vincristine. Others include ethanol and amyloid peptide. (*Science* 267:1457–1458 (1995)).

Antagonists according to the present invention include soluble forms of the TR11, TR11SV1, and TR11SV2 receptors (e.g., fragments of the TR11, TR11SV1, and TR11SV2 receptors shown in FIGS. 1A and 1B, 2A and 2B, and 3A and 3B, respectively, that include the ligand binding domain from the extracellular region of the full length receptor). Such soluble forms of the receptor, which may be naturally occurring or synthetic, antagonize TR11, TR11SV1, and TR11SV2 mediated signaling by competing with the cell surface bound forms of the receptor for binding to TNF-family ligands. Antagonists of the present invention also include antibodies specific for TNF-family ligands and TR11-, TR11SV1-, and TR11SV2-Fc fusion proteins.

By a "TNF-family ligand" is intended naturally occurring, recombinant, and synthetic ligands that are capable of binding to a member of the TNF receptor family and inducing the ligand/receptor signaling pathway. Members of the TNF ligand family include, but are not limited to, TNF-α, lymphotoxin-α (LT-α, also known as TNF-β), LT-β (found in complex heterotrimer LT-α2-β), FasL, CD40L, CD27L, CD30L, 4-1BBL, OX40L and nerve growth factor (NGF).

TNF-α has been shown to protect mice from infection with herpes simplex virus type 1 (HSV-1). Rossol-Voth, R. et al., *J. Gen. Virol.* 72:143–147 (1991). The mechanism of the protective effect of TNF-α is unknown but appears to involve neither interferons not NK cell killing. One member of the TNFR family has been shown to mediate HSV-1 entry into cells. Montgomery, R. et al., *Eur. Cytokine Newt.* 7:159 (1996). Further, antibodies specific for the extracellular domain of this TNFR block HSV-1 entry into cells. Thus, TR11, TR11SV1, and TR11SV2 antagonists of the present invention include both TR11, TR11SV1, and TR11SV2 amino acid sequences and antibodies capable of preventing TNFR mediated viral entry into cells. Such sequences and antibodies can function by either competing with cell surface localized TNFR for binding to virus or by directly blocking binding of virus to cell surface receptors.

Antibodies according to the present invention may be prepared by any of a variety of methods using TR11, TR11SV1, and TR11SV2 receptor immunogens of the present invention. Such TR11, TR11SV1, and TR11SV2 receptor immunogens include the TR11, TR11SV1, and TR11SV2 receptor proteins shown in FIGS. 1A and 1B, 2A and 2B, and 3A and 3B (SEQ ID NO:2, SEQ ID NO:4, and SEQ ID NO:6, respectively; which may or may not include a leader sequence) and polypeptide fragments of the receptor comprising the ligand binding, extracellular, transmembrane, the intracellular domains of the TR11, TR11SV1, and TR11SV2 receptors, or any combination thereof.

Polyclonal and monoclonal antibody agonists or antagonists according to the present invention can be raised according to the methods disclosed in Tartaglia and Goeddel, *J. Biol. Chem.* 267(7):4304–4307(1992)); Tartaglia et al., *Cell* 73:213–216 (1993)), and PCT Application WO 94/09137. The term "antibody" (Ab) or "monoclonal antibody" (mAb) as used herein is meant to include intact molecules as well as fragments thereof (such as, for example, Fab and F(ab') fragments) which are capable of binding an antigen. Fab and F(ab') fragments lack the Fc fragment of intact antibody, clear more rapidly from the circulation, and may have less non-specific tissue binding of an intact antibody (Wahl et al., *J. Nucl. Med.* 24:316–325 (1983)).

In a preferred method, antibodies according to the present invention are mAbs. Such mAbs can be prepared using hybridoma technology (Kohler and Millstein, *Nature* 256:495–497 (1975) and U.S. Pat. No. 4,376,110; Harlow et al., *Antibodies*: A Laboratory Manual, Cold Spring Harbor Laboratory Press, Cold Spring Harbor, N.Y., 1988; *Monoclonal Antibodies and Hybridomas: A New Dimension in Biological Analyses*, Plenum Press, New York, N.Y., 1980; Campbell, "Monoclonal Antibody Technology," In: *Laboratory Techniques in Biochemistry and Molecular Biology*, Volume 13 (Burdon et al., eds.), Elsevier, Amsterdam (1984)).

Proteins and other compounds which bind the TR11, TR11SV1, and TR11SV2 receptor domains are also candidate agonist and antagonist according to the present invention. Such binding compounds can be "captured" using the yeast two-hybrid system (Fields and Song, *Nature* 340:245–246 (1989)). A modified version of the yeast two-hybrid system has been described by Roger Brent and his colleagues (Gyuris, J. et al., *Cell* 75:791–803 (1993); Zervos, A. S. et al., *Cell* 72:223–232 (1993)). Preferably, the yeast two-hybrid system is used according to the present invention to capture compounds which bind to the ligand binding, extracellular, intracellular, and transmembrane domains of the TR11, TR11SV1, and TR11SV2 receptors. Such compounds are good candidate agonist and antagonist of the present invention.

Using the two-hybrid assay described above, the intracellular domain of the TR11, TR11SV1, and TR11SV2 receptors, or portions thereof, may be used to identify cellular proteins which interact with the receptor in vivo. Such an assay may also be used to identify ligands with potential agonistic or antagonistic activity of TR11, TR11SV1, and TR11SV2 receptor function. This screening assay has previously been used to identify protein which interact with the cytoplasmic domain of the murine TNF-RII and led to the identification of two receptor associated proteins (Rothe, M. et al., *Cell* 78:681 (1994)). Such proteins and amino acid sequences which bind to the cytoplasmic domain of the TR11, TR11SV1, and TR11SV2 receptors are good candidate agonists and antagonists of the present invention.

Other screening techniques include the use of cells which express the polypeptide of the present invention (for example, transfected CHO cells) in a system which measures extracellular pH changes caused by receptor activation, for example, as described in *Science*, 246:181–296 (1989). In another example, potential agonists or antagonists may be contacted with a cell which expresses the polypeptide of the present invention and a second messenger response, e.g., signal transduction may be measured to determine whether the potential antagonist or agonist is effective.

The TR11, TR11SV1, and TR11SV2 receptor agonists may be employed to stimulate ligand activities, such as inhibition of tumor growth and necrosis of certain transplantable tumors. The agonists may also be employed to stimulate cellular differentiation, for example, T-cell, fibroblasts and hemopoietic cell differentiation. Agonists to the TR11, TR11SV1, and TR11SV2 receptors may also augment the role of TR11, TR11SV1, and TR11SV2 in the host's defense against microorganisms and prevent related diseases (infections such as that from *Listeria monocytogenes*) and Chlamidiace. The agonists may also be employed to protect against the deleterious effects of ionizing radiation produced during a course of radiotherapy, such as denaturation of enzymes, lipid peroxidation, and DNA damage.

Agonists to the receptor polypeptides of the present invention may be used to augment TNF's role in host defenses against microorganisms and prevent related diseases. The agonists may also be employed to protect against the deleterious effects of ionizing radiation produced during a course of radiotherapy, such as denaturation of enzymes, lipid peroxidation, and DNA damage.

The agonists may also be employed to mediate an antiviral response, to regulate growth, to mediate the immune response and to treat immunodeficiencies related to diseases such as HIV by increasing the rate of lymphocyte proliferation and differentiation.

The antagonists to the polypeptides of the present invention may be employed to inhibit ligand activities, such as stimulation of tumor growth and necrosis of certain transplantable tumors. The antagonists may also be employed to inhibit cellular differentiation, for example, T-cell, fibroblasts and hemopoietic cell differentiation. Antagonists may also be employed to treat autoimmune diseases, for example, graft versus host rejection and allograft rejection, and T-cell mediated autoimmune diseases such as AIDS. It has been shown that T-cell proliferation is stimulated via a type 2 TNF receptor. Accordingly, antagonizing the receptor may prevent the proliferation of T-cells and treat T-cell mediated autoimmune diseases.

The state of immunodeficiency that defines AIDS is secondary to a decrease in the number and function of $CD4^+$ T-lymphocytes. Recent reports estimate the daily loss of $CD4^+$ T cells to be between $3.5 \times 10^7$ and $2 \times 10^9$ cells (Wei X., et al., *Nature* 373:117–122 (1995)). One cause of $CD4^+$ T cell depletion in the setting of HIV infection is believed to be HIV-induced apoptosis. Indeed, HIV-induced apoptotic cell death has been demonstrated not only in vitro but also, more importantly, in infected individuals (Ameisen, J. C., *AIDS* 8:1197–1213 (1994); Finkel, T. H., and Banda, N. K., *Curr. Opin. Immunol.* 6:605–615(1995); Muro-Cacho, C. A. et al., *J. Immunol.* 154:5555–5566 (1995)). Furthermore, apoptosis and $CD4^+$ T-lymphocyte depletion is tightly correlated in different animal models of AIDS (Brunner, T., et al., *Nature* 373:441–444 (1995); Gougeon, M. L., et al., *AIDS Res. Hum. Retroviruses* 9:553–563 (1993)) and, apoptosis is not observed in those animal models in which viral replication does not result in AIDS (Gougeon, M. L. et al., *AIDS Res. Hum. Retroviruses* 9:553–563 (1993)). Further data indicates that uninfected but primed or activated T lymphocytes from HIV-infected individuals undergo apoptosis after encountering the TNF-family ligand FasL. Using monocytic cell lines that result in death following HIV infection, it has been demonstrated that infection of U937 cells with HIV results in the de novo expression of FasL and that FasL mediates HIV-induced apoptosis (Badley, A. D. et al., *J. Virol.* 70:199–206 (1996)). Further the TNF-family ligand was detectable in uninfected macrophages and its expression was upregulated following HIV infection resulting in selective killing of uninfected CD4$^+$ T-lymphocytes (Badley, A. D et al., *J. Virol.* 70:199–206 (1996)).

In rejection of an allograft, the immune system of the recipient animal has not previously been primed to respond because the immune system for the most part is only primed by environmental antigens. Tissues from other members of the same species have not been presented in the same way that, for example, viruses and bacteria have been presented. In the case of allograft rejection, immunosuppressive regimens are designed to prevent the immune system from reaching the effector stage. However, the immune profile of xenograft rejection may resemble disease recurrence more that allograft rejection. In the case of disease recurrence, the immune system has already been activated, as evidenced by destruction of the native islet cells. Therefore, in disease recurrence the immune system is already at the effector stage. Antagonists of the present invention are able to suppress the immune response to both allografts and xenografts by decreasing the rate of TR11-, TR11SV1-, and TR11SV2-mediated xenografts by decreasing the rate of TR11-, TR11SV1-, and TR11SV2-mediated lymphocyte proliferation and differentiation. Such antagonists include the TR11-, TR11SV1-, and TR11SV2-Fc fusion proteins described in Example 5. Thus, the TR11SV1-, and TR11SV2-Fc fusion proteins described in Example 5. Thus, the present invention further provides a method for suppression of immune responses.

In addition, TNF-α has been shown to prevent diabetes in strains of animals which are prone to this affliction resulting from autoimmunity. See Porter, A., *Tibtech* 9:158–162 (1991). Thus, agonists and antagonists of the present invention may be useful in the treatment of autoimmune diseases such as type 1 diabetes.

In addition, the role played by the TR11, TR11SV1, and TR11SV2 receptors in cell proliferation and differentiation indicates that agonist or antagonist of the present invention may be used to treat disease states involving aberrant cellular expression of these receptors. TR11, TR11SV1, and TR11SV2 receptors may in some circumstances induce an inflammatory response, and antagonist may be useful reagents for blocking this response. Thus, TR11, TR11SV1, and TR11SV2 receptor antagonists (e.g., soluble forms of the TR11, TR11SV1, and TR11SV2 receptors; neutralizing antibodies) may be useful for treating inflammatory diseases, such as rheumatoid arthritis, osteoarthritis, psoriasis, septicemia, and inflammatory bowel disease.

Antagonists to the TR11, TR11SV1, and TR11SV2 receptor may also be employed to treat and/or prevent septic shock, which remains a critical clinical condition. Septic shock results from an exaggerated host response, mediated by protein factors such as TNF and IL-1, rather than from a pathogen directly. For example, lipopolysaccharides have been shown to elicit the release of TNF leading to a strong and transient increase of its serum concentration. TNF causes shock and tissue injury when administered in excessive amounts. Accordingly, it is believed that antagonists to the TR11, TR11SV1, and TR11SV2 receptors will block the actions of TNF and treat/prevent septic shock. These antagonists may also be employed to treat meningococcemia in children which correlates with high serum levels of TNF.

Among other disorders which may be treated by the antagonists to TR11, TR11SV1, and TR11SV2 receptors, there are included, inflammation which is mediated by TNF receptor ligands, and the bacterial infections cachexia and cerebral malaria. The TR11, TR11SV1, and TR11SV2 receptor antagonists may also be employed to treat inflammation mediated by ligands to the receptor such as TNF.

Biological Activities of TR11, TR11SV1 or TR11SV2

TR11, TR11SV1 or TR11SV2 polynucleotides and polypeptides can be used in assays to test for one or more biological activities. If TR11, TR11SV1 or TR11SV2 polynucleotides and polypeptides do exhibit activity in a particular assay, it is likely that TR11, TR11SV1 or TR11SV2 may be involved in the diseases associated with the biological activity. Therefore, TR11, TR11SV1 or TR11SV2 could be used to treat the associated disease.

Immune Activity

TR11, TR11SV1 or TR11SV2 polypeptides or polynucleotides may be useful the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, TR11, TR11SV1 or TR11SV2 polynucleotides or polypeptides can be used as a marker or detector of a particular immune system disease or disorder.

TR11, TR11SV1 or TR11SV2 polynucleotides or polypeptides may be useful in treating or detecting deficiencies or disorders of hematopoietic cells. TR11, TR11SV1 or TR11SV2 polypeptides or polynucleotides could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. a gammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, TR11, TR11SV1 or TR11SV2 polypeptides or polynucleotides can also be used to modulate hemostatic (the stopping of bleeding) or thrombolytic activity (clot formation). For example, by increasing hemostatic or thrombolytic activity, TR11, TR11SV1 or TR11SV2 polynucleotides or polypeptides could be used to treat blood coagulation disorders (e.g., afibrinoginenemia, factor deficiencies), blood platelet disorders (e.g. thrombocytopenia), or wounds resulting from trauma, surgery, or other causes. Alternatively, TR11, TR11SV1 or TR11SV2 polynucleotides or polypeptides that can decrease hemostatic or thrombolytic activity could be used to inhibit or dissolve clotting, important in the treatment of heart attacks (infarction), strokes, or scarring.

TR11, TR11SV1 or TR11SV2 polynucleotides or polypeptides may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of TR11, TR11SV1 or TR11SV2 polypeptides or polynucleotides that can inhibit an immune response, particularly the proliferation, differentiation, or chemotaxis of T-cells, may be an effective therapy in preventing autoimmune disorders.

Examples of autoimmune disorders that can be treated or detected by TR11, TR11SV1 or TR11SV2 include, but are not limited to: Addison's Disease, hemolytic anemia, anti phospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitus, and autoimmune inflammatory eye disease.

Similarly, allergic reactions and conditions, such as asthma (particularly allergic asthma) or other respiratory problems, may also be treated by TR11, TR11SV1 or TR11SV2 polypeptides or polynucleotides. Moreover, TR11, TR11SV1 or TR11SV2 can be used to treat anaphylaxis, hypersensitivity to an antigenic molecule, or blood group incompatibility.

TR11, TR11SV1 or TR11SV2 polynucleotides or polypeptides may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of TR11, TR11SV1 or TR11SV2 polypeptides or polynucleotides that inhibits an immune response, particularly the proliferation, differentiation, or chemotaxis of T-cells, may be an effective therapy in preventing organ rejection or GVHD.

Similarly, TR11, TR11SV1 or TR11SV2 polypeptides or polynucleotides may also be used to modulate inflammation. For example, TR11, TR11SV1or TR11SV2 polypeptides or polynucleotides may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyper proliferative Disorders

TR11, TR11SV1 or TR11SV2 polypeptides or polynucleotides can be used to treat or detect hyperproliferative disorders, including neoplasms. TR11, TR11SV1 or TR11SV2 polypeptides or polynucleotides may inhibit the proliferation of the disorder through direct or indirect interactions. Alternatively, TR11, TR11SV1 or TR11SV2 polypeptides or polynucleotides may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by TR11, TR11SV1 or TR11SV2 polynucleotides or polypeptides include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by TR11, TR11SV1 or TR11SV2 polynucleotides or polypeptides. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Infectious Disease

TR11, TR11SV1 or TR11SV2 polypeptides or polynucleotides can be used to treat or detect infectious agents. For example, by increasing the immune response. particularly increasing the proliferation and differentiation of B and/or T cells, infectious diseases may be treated. The immune response may be increased by either enhancing an existing immune response, or by initiating a new immune response. Alternatively, TR11, TR11SV1 or TR11SV2 polypeptides or polynucleotides may also directly inhibit the infectious agent, without necessarily eliciting an immune response.

Viruses are one example of an infectious agent that can cause disease or symptoms that can be treated or detected by TR11, TR11SV1 or TR11SV2 polynucleotides or polypeptides. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox , hemorrhagic fever, Measles, Mumps, Parainfluenza, Rabies, the common cold, Polio, leukemia, Rubella, sexually transmitted diseases, skin diseases (e.g., Kaposi's, warts), and viremia. TR11, TR11SV1 or TR11SV2 polypeptides or polynucleotides can be used to treat or detect any of these symptoms or diseases.

Similarly, bacterial or fungal agents that can cause disease or symptoms and that can be treated or detected by TR11, TR11SV1 or TR11SV2 polynucleotides or polypeptides include, but not limited to, the following Gram-Negative and Gram-positive bacterial families and fungi: Actinomycetales (e.g., Corynebacterium, Mycobacterium, Norcardia), Aspergillosis, Bacillaceae (e.g., Anthrax, Clostridium), Bacteroidaceae, Blastomycosis, Bordetella, Borrelia, Brucellosis, Candidiasis, Campylobacter, Coccidioidomycosis, Cryptococcosis, Dermnatocycoses, Enterobacteriaceae (Klebsiella, Salmonella, Serratia, Yersinia), Erysipelothrix, Helicobacter, Legionellosis, Leptospirosis, Listeria, Mycoplasmatales, Neisseriaceae (e.g., Acinetobacter, Gonorrhea, Menigococcal), Pasteurellacea Infections (e.g., Actinobacillus, Heamophilus, Pasteurella), Pseudomonas, Rickettsiaceae, Chlamydiacae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. TR11, TR11SV1 or TR11SV2 polypeptides or polynucleotides can be used to treat or detect any of these symptoms or diseases.

Moreover, parasitic agents causing disease or symptoms that can be treated or detected by TR11, TR11SV1 or TR11SV2 polynucleotides or polypeptides include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. TR11, TR11SV1 or TR11SV2 polypeptides or polynucleotides can be used to treat or detect any of these symptoms or diseases.

Preferably, treatment using TR11, TR11SV1 or TR11SV2 polypeptides or polynucleotides could either be by administering an effective amount of TR11, TR11SV1 or TR11SV2 polypeptide to the patient, or by removing cells from the patient, supplying the cells with TR11, TR11SV1 or TR11SV2 polynucleotide, and returning the engineered cells to the patient (ex vivo therapy). Moreover, the TR11, TR11SV1 or TR11SV2 polypeptide or polynucleotide can be used as an antigen in a vaccine to raise an immune response against infectious disease.

Regeneration

TR11, TR11SV1 or TR11SV2 polynucleotides or polypeptides can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vascular (including vascular endothelium), nervous, hematopoietic, and skeletal (bone, cartilage, tendon, and ligament) tissue. Preferably, regeneration occurs without or decreased scarring. Regeneration also may include angiogenesis.

Moreover, TR11, TR11SV1 or TR11SV2 polynucleotides or polypeptides may increase regeneration of tissues difficult to heal. For example, increased tendon/ligament regeneration would quicken recovery time after damage. TR11, TR11SV1 or TR11SV2 polynucleotides or polypeptides of the present invention could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using TR11, TR11SV1 or TR11SV2 polynucleotides or polypeptides to proliferate and differentiate peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the TR11, TR11SV1 or TR11SV2 Drager syndrome), could all be treated using the TR11, TR11SV1 or TR11SV2 polynucleotides or polypeptides.

Chemotaxis

TR11, TR11SV1 or TR11SV2 polynucleotides or polypeptides may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

TR11, TR11SV1 or TR11SV2 polynucleotides or polypeptides may increase chemotaxic activity of particular cells. These chemotaxec molecules can then be used to treat inflammation, infection, hyperproliferative disorders, or any immune system disorder by increasing the number of cells targeted to a particular location in the body. For example, chemotaxic molecules can be used to treat wounds and other trauma to TR11, TR11SV1 or TR11SV2 could also attract fibroblasts, which can be used to treat wounds.

It is also contemplated that TR11, TR11SV1 or TR11SV2 polynucleotides or treat disorders. Thus, TR11, TR11SV1 or TR11SV2 polynucleotides or polypeptides could be used as an inhibitor of chemotaxis.

Modes of Administration

The agonist or antagonist described herein can be administered in vivo, ex vivo, or in vivo to cells which express the receptor of the present invention. By administration of an "effective amount" of an agonist or antagonist is intended an amount of the compound that is sufficient to enhance or inhibit a cellular response to a TNF-family ligand and include polypeptides. In particular, by administration of an "effective amount" of an agonist or antagonists is intended an amount effective to enhance or inhibit TR11, TR11SV1, and TR11SV2 receptor mediated activity. Of course, where cell proliferation and/or differentiation is to be enhanced, an agonist according to the present invention can be co-administered with a TNF-family ligand. One of ordinary skill will appreciate that effective amounts of an agonist or antagonist can be determined empirically and may be employed in pure form or in pharmaceutically acceptable salt, ester or pro-drug form. The agonist or antagonist may be administered in compositions in combination with one or more pharmaceutically acceptable excipients.

It will be understood that, when administered to a human patient, the total daily usage of the compounds and compositions of the present invention will be decided by the attending physician within the scope of sound medical judgement. The specific therapeutically effective dose level for any particular patient will depend upon factors well known in the medical arts.

As a general proposition, the total pharmaceutically effective amount of a TR11, TR11SV1 or TR11SV2 polypeptide administered parenterally per dose will be in the range of about 1 µg/kg/day to 10 mg/kg/day of patient body weight, although, as noted above, this will be subject to therapeutic discrerion. More preferably, this dose is at least 0.01 mg/kg/day, and most preferably for humans between about 0.01 and 1 mg/kg/day for the hormone. If given continuously, the TR11, TR11SV1, and TR11SV2 polypeptides are typically administered at a dose rate of about 1 µg/kg/hour to about 50 µg/kg/hour, either by 1–4 injections per day or by continuous subcutaneous infusions, for example, using a mini-pump. An intravenous bag solution may also be employed.

Pharmaceutical compositions containing the TR11, TR11SV1, and TR11SV2 receptor polypeptides of the invention may be administered orally, rectally, parenterally, intracisternally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

Having generally described the invention, the same will be more readily understood by reference to the following examples, which are provided by way of illustration and are not intended as limiting.

EXAMPLES

Example 1

Expression and Purification of TR8 in *E. coli*

The bacterial expression vector pQE60 is used for bacterial expression in this example. (QIAGEN, Inc., 9259 Eton Avenue, Chatsworth, Calif., 91311). pQE60 encodes ampicillin antibiotic resistance("Amp'") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arraigned such that a DNA fragment encoding a polypeptide may be inserted in such as way as to produce that polypeptide with the six His residues (i.e., a "6× His tag") covalently linked to the carboxyl terminus of that polypeptide. However, in this example, the polypeptide coding sequence is inserted such that translation of the six His codons is prevented and, therefore, the polypeptide is produced with no 6× His tag.

Alternatively, the novel pHE4 series of bacterial expression vectors, in particular, the pHE4-5 vector may be used for bacterial expression in this example. The pHE4-5/MPIFD23 vector plasmid DNA containing an insert which encodes another ORF (using the Nde I and Asp 718 flanking restriction sites, one of ordinary skill in the art could easily use the current molecular biological techniques to replace the irrelevent ORF in the pHE4-5 vector with the ORF of the present invention) was deposited on Sep. 30, 1997 at the American Type Culture Collection, 10801 University Boulevard, Manassas, Va. 20110-2209, and given ATCC Deposit No. 209311. The bacterial expression vector pHE4-5 includes a neomycin phosphotranferase gene for selection, an *E. coli* origin of replication, a T5 phage promoter sequence, two lac operator sequences, a ShineDelgarno sequence, and the lactose operon repressor gene (lacIq). The promoter and operator sequences of the pHE4-5 vector were made synthetically. Synthetic production of nucleic acid sequences is well known in the art (CLONETECH 95/96 Catalog, pages 215–216, CLONETECH, 1020 East Meadow Circle, Palo Alto, Calif. 94303).

The DNA sequence encoding the desired portion of the TR11 protein lacking the hydrophobic leader sequence is amplified from the deposited cDNA clone using PCR oligonucleotide primers which anneal to the amino terminal sequences of the desired portion of the TR11 protein and to sequences in the deposited construct 3' to the cDNA coding sequence. Additional nucleotides containing restriction sites to facilitate cloning in the pQE60 vector are added to the 5' and 3' sequences, respectively.

For cloning the soluble extracellular domain of the TR1 protein, the 5' primer has the sequence: 5'-CGC <u>CCA TGG</u> CAG CGC CCC ACC G-3' (SEQ ID NO:10) containing the underlined Nco I restriction site followed by 13 nucleotides TR11 sequence in FIGS. 1A and 1B (nucleotides 184–195 of SEQ ID NO:1). One of ordinary skill in the art would appreciate, of course, that the point in the protein coding sequence where the 5' primer begins may be varied to amplify a desired portion of the complete protein shorter or longer than the mature form. The 3' primer for the soluble extracellular domain has the sequence: 5' CGC <u>AAG CTT</u> GGC TCT GCC GGC G 3' (SEQ ID NO:11) containing the underlined HindIII restriction site followed by 13 nucleotides complementary to the 3' end of the extracellular domain portion of the nucleotide sequence shown in FIGS. 1A and 1B (nucleotides 590–602 in SEQ ID NO:1) encoding the extracellular domain of the TR11 receptor.

The amplified TR11 DNA fragments and the vector pQE60 are digested with Nco I and Hind III and the digested DNAs are then ligated together. Insertion of the TR11 DNA into the restricted pQE60 vector places the TR11 protein coding region downstream from the IPTG-inducible promoter and in-frame with an initiating AUG.

The ligation mixture is transformed into competent *E. coli* cells using standard procedures such as those described in Sambrook et al., *Molecular Cloning: a Laboratory Manual, 2nd Ed.*; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kan'"), is used in carrying out the illustrative example described herein. This strain, which is only one of many that are suitable for expressing TR11 protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 µg/ml) and kanamycin (25 µg/ml). The O/N culture is used to inoculate a large culture, at a dilution of approximately 1:25 to 1:250. The cells are grown to an optical density at 600 nm ("OD600") of between 0.4 and 0.6. Isopropyl-b-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6 M guanidine-HCl, pH 8. The cell debris is removed by centrifugation, and the supernatant containing the TR11 extracellular domain polypeptide is dialyzed against 50 mM Na-acetate buffer pH 6, supplemented with 200 mM NaCl. Alternatively, the protein can be successfully refolded by dialyzing it against 500 mM NaCl, 20% glycerol, 25 mM Tris/HCl pH 7.4, exchange, hydrophobic interaction and size exclusion chromatography. Alternatively, an affinity chromatography step such as an antibody column can be used to obtain pure TR11 extracellular domain polypeptide. The purified protein is stored at 4° C. or frozen at –80° C.

The skilled artisan appreciates that a similar approach could easily be designed and utilized to generate pQE60-based bacterial expression constructs for the expression of TR11SV1 and TR11SV2 in *E. coli*. This would be done by designing PCR primers containing similar restriction endonuclease recognition sequences combined with gene-specific sequences for TR11SV1 and TR11SV2 and proceeding as described above.

Example 2(a)

Cloning and Expression of a Soluble Fragment of TR11 Protein in a Baculovirus Expression System In this example, the plasmid shuttle vector pA2GP was used to insert the cloned DNA encoding the mature extracellular domain of the TR11 receptor protein shown in FIGS. 1A and 1B, lacking its naturally associated secretory signal (leader) sequence, into a baculovirus. This protein was expressed using a baculovirus leader and standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the Autographica californica nuclear polyhedrosis virus (AcMNPV) followed by the secretory signal peptide (leader) of the baculovirus gp67 protein and convenient restriction sites such as Bam HI, Xba I and Asp 718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate viable virus that expresses the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39.

The cDNA sequence encoding essentially the extracellular domain with leader (amino acids 1 to 162 shown in FIGS. 1A and 1B) of the TR11 receptor protein in the deposited clone (ATCC Deposit Number 209340) is amplified using PCR oligonucleotide primers corresponding to the relevant 5' and 3' sequences of the gene. The 5' primer for the above has the sequence: 5-CGC <u>GGA TCC</u> CAG CGC CCC ACC G-3' (SEQ ID NO:12) containing the underlined Bam HI restriction enzyme site, an efficient signal for initiation of translation in eukaryotic cells, as described by Kozak, M.,*J. Mol. Biol.* 196:947–950 (1987), followed by 13 bases of the coding sequence of the TR11 protein shown in FIGS. 1A and 1B (nucleotides 193–205 in SEQ ID NO:1). The 3' primer has the sequence: 5' CGC <u>GGT</u> ACC GGC TCT GCC GGC G-3' (SEQ ID NO:13) containing the underlined Asp 718 restriction sites followed by 13 nucleotides complementary to the coding sequence in FIGS. 1A an 1B (nucleotides 590–602 in SEQ ID NO:1).

The amplified fragment is isolated from a 1% agarose gel using a commercially available kit ("Geneclean," BIO 101 Inc., La Jolla, Calif.). The fragment was then digested with Bam HI and Asp 718 and purified on a 1% agarose gel. This fragment is designated herein "F1".

The plasmid is digested with the restriction enzymes Bam HI and Asp 718 dephsphorylated using calf intestinal phosphatase. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB101 cells are transformed with the ligation mixture and spread on culture plates. Other suitable *E. coli* hosts such as XL-1 Blue (Stratagene Cloning Systems, La Jolla, Calif.) may also be used. Bacteria are identified that contain the plasmid with the human TR11 sequences using the PCR method, in which one of the above primers is used to amplify the gene and the second primer is from well within the vector so that only those bacterial colonies containing TR11 gene fragments show amplification of the DNA. The sequence of the cloned fragment is confirmed by DNA sequencing. The plasmid is designated herein pBacTR11-T.

Five µg of pBacTR11-T is co-transfected with 1.0 µg of a commercially available linearized baculovirus DNA ("BaculoGold baculovirus DNA", Pharmingen, San Diego, Calif.), using the lipofection method described by Felgner et al., *Proc. Natl. Acad. Sci. USA* 84:7413–7417 (1987). 1 µg of BaculoGold virus DNA and 5 µg of plasmid pBacTR11-T are mixed in a sterile well of a microtiter plate containing 50 µl of serum-free Grace's medium (Life Technologies Inc. Gaithersburg, Md.). Afterwards, 10 µl Lipofectin plus 90 µl Grace's medium are added, mixed and incubated for 15 minutes at room temperature. Then the transfection mixture is added dropwise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay"

of this type can also be found in the user's guide for insect cell culture and baculovirology distributed by Life Technologies Inc., Gaithersburg, page 9–10). After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-TR11-T.

To verify the expression of the gene used, Sf9 cells are grown in Grace's medium supplemented with 10% heat inactivated FBS. The cells are infected with the recombinant baculovirus V-TR11-T at a multiplicity of infection ("MOI") of about 2. Six hours later the medium is removed and replaced with SF900 II medium minus methionine and cysteine (available from Life Technologies Inc., Rockville, Md.). Forty-two hours later, 5 µCi of $^{35}$S-methionine and 5 µCi $^{35}$S-cysteine (available from Amersham) are added to radiolabel proteins. The cells are further incubated for 16 hours and then they are harvested by centrifugation. The proteins in the supernatant as well as the intracellular proteins are analyzed by SDS-PAGE followed by autoradiography. Microsequencing of the amino acid sequence of the amino terminus of purified protein is used to determine the amino terminal sequence of the mature protein and thus the cleavage point and length of the secretory signal peptide.

Example 2(b)

Cloning and Expression of the Full-Length Gene for TR11 Protein in a Baculovirus Expression System Similarly to the cloning and expression of the truncated version of the TR11 receptor described in Example 2(a), recombinant baculoviruses were generated which express the full length TR11 receptor protein shown in FIGS. 1A and 1B (SEQ ID NO:2).

In this example, the plasmid shuttle vector pA2 is used to insert the cloned DNA encoding the complete protein, including its naturally associated secretory signal (leader) sequence, into a baculovirus to express the mature TR11 protein. Other attributes of the pA2 vector are as described for the pA2GP vector used in Example 2(a).

The cDNA sequence encoding the full length TR11 protein in the deposited clone, including the AUG initiation codon and the naturally associated secretory signal shown in FIGS. 1A and 1B (SEQ ID NO:2), is amplified using PCR oligonucleotide primers corresponding to the 5' and 3' sequences of the gene. The 5' primer for the above has the sequence: 5-CGC GGA TCC CCG CCA TCA TGG CAC AGC ACG GGG CG-3' (SEQ ID NO:14) containing the underlined Bam HI restriction enzyme site, an efficient signal for initiation of translation in eukaryotic cells (in italics), as described by Kozak, M., *J. Mol. Biol.* 196:947–950 (1987), followed by 16 bases of the coding sequence of the TR11 protein shown in FIGS. 1A and 1B (nucleotides 118–135 in SEQ ID NO:1). A suitable 3' primer for this purpose has the sequence: 5' CGC GGT ACC CAC CCA CAG GTC TCC C-3' (SEQ ID NO:15) containing the underlined Asp 718 restriction sites followed by 16 nucleotides complementary to the coding sequence in FIGS. 1A and 1B (nucleotides 804–819 in SEQ ID NO:1).

The amplified fragment is isolated and digested with restriction enzymes as described in Example 2(a) to produce plasmid pBacTR11.

5 µg of pBacTR11 is co-transfected with 1 µg of BaculoGold (Pharmingen) viral DNA and 10 µl of Lipofectin (Life Technologies, Inc.) in a total volume of 200 µl serum free media. The primary viruses are harvested at 4–5 days post-infection (pi), and used in plaque assays. Plaque purified viruses are subsequently amplified and frozen, as described in Example 2(a).

For radiolabeling of expressed proteins, Sf9 cells are seeded in 12 well dishes with 2. 0 ml of a cell suspension containing 0.5×10$^6$ cells/ml and allowed to attach for 4 hours. Recombinant baculoviruses are used to infect the cells at an MOI of 1–2. After 4 hours, the media is replaced with 1. 0 ml of serum free media depleted for methionine and cysteine (-Met/-Cys). At 3 days pi, the culture media is replaced with 0.5 ml -Met/-Cys containing 2 µCi each [$^{35}$S]-Met and [$^{35}$S]-Cys. Cells are labeled for 16 hours after which the culture media is removed and clarified by centrifugation (Supernatant). The cells are lysed in the dish by addition of 0.2 ml lysis buffer (20 mM HEPES, pH 7.9; 130 mM NaCl; 0.2 mM EDTA; 0.5 mM DTT and 0.5% vol/vol NP-40) and then diluted up to 1.0 ml with dH$_2$O (Cell Extract). 30 µl of each supernatant and cell extract are resolved by 15% SDS-PAGE. Protein gels are stained, destained, recombinant proteins are visible after 16–72 hours exposure.

The skilled artisan appreciates that a similar approach could easily be designed and utilized to generate pA2GP- and pA2-based baculovirus expression constructs for the expression of TR11SV1 and TR11SV2 in insect cells. This would be done by sequences combined with gene-specific sequences for TR11SV1 and TR11SV2 and proceeding as described above.

Example 3

Cloning and Expression of TR11 in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as PSVL and PMSG (Pharmacia, Uppsala, Sweden), pRSVcat (ATCC 37152), pSV2dhfr (ATCC 37146) and pBC12MI (ATCC 67109). Manmmalian host cells that could be used include, human HeLa 293, H9 and Jurkat cells, mouse NIH3T3 and C127 cells, Cos 1, Cos 7 and CV 1, quail QC1–3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS; Murphy et al., *Biochem J.* 227:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molecular and Cellular Biology*, 438447 (March, 1985)) plus a fragment of the CMV-enhancer (Boshart et al., *Cell* 41:521–530 (1985)). and Asp 718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pTR11 HA, is made by cloning a cDNA encoding the soluble extracellular portion of the TR11 protein into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37:767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding a TR11 protein is cloned into the polylinker region of the vector so that recombinant protein expression is directed by the CMV promoter. The plasmid construction strategy is as follows. The TR11 cDNA of the deposited clone is amplified using primers that contain convenient restriction sites, much as described above for construction of vectors for expression of TR11 in *E. coli*. Suitable primers include the following, which are used in this example. The 5' primer, containing the underlined Bam HI site, a Kozak sequence (in italics), an AUG start codon and 13 additional codons of the 5' coding region of the complete TR11 has the following sequence: 5'-CGC GGA TCC GCC ATC ATG CAG CGC CCC ACC G-3' (SEQ ID NO:16). The 3' primer has the sequence: 5' CGC TCT AGA TCA AGC GTA GTC TGG GAC GTC GTA TGG GTA TTA GGC TCT GCC GGC G-3' (SEQ ID NO:17) containing the underlined Xba I restriction site followed by a stop codon, a sequence encoding a 6× his tag, and 15 nucleotides complementary to the coding sequence in FIGS. 1A and 1B (nucleotides 590–602 in SEQ ID NO:1).

The PCR amplified DNA fragment and the vector, pcDNAI/Amp, are digested with Bam HI Xba I and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the TR11-encoding fragment.

For expression of recombinant TR11, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of TR11 by the vector.

Expression of the TR11-HA fusion protein is detected by radiolabeling and immunoprecipitation, using methods described in, for example Harlow et al., *Antibodies: A Laboratory Manual*, 2nd Ed.; Cold Spring Harbor Laboratory Press, Cold Spring Harbor, N.Y. (1988). To this end, two days after transfection, the cells are labeled by incubation in media containing [$^{35}$S]-cysteine for 8 hours. The cells and the media are collected, and the cells are washed and lysed with detergent-containing RIPA buffer: 150 mM NaCl, 1% NP-40, 0.1% SDS, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of TR11 protein. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lasking dihydrofolate activity that are transfected with these plasmids can be selected by growing the cells in a selective medium (alpha minus MEM, Life Technologies) supplemented with the chemotherapeutic agent methrexate. The amplification of the DHFR genes in cells resistant to methotrexate (MTX) has been well documented (see, e.g., Alt, F. W., Kellems, R. M., Bertino, J. R., and Schimke, R. T., 1978, *J Biol. Chem.* 253:1357–1370, Hamlin, J. L. and Ma, C. 1990, *Biochem. et Biophys. Acta*, 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., *Molecular and Cellular Biology*, March 1985:438–447) plus a fragment isolated from the enhancer of the immediate early gene of human cytomegalovirus (CMV) (Boshart et al., *Cell* 41:521–530

(1985)). Downstream of the promoter are Bam HI, Xba 1, and Asp 718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human -actin promoter, the SV40 early or late promoters or the long terminal repeats from other retroviruses, e.g., HIV and HTLVI. Clontech's Tet-Off and Tet-On gene expression systems and similar systems can be used to express the TR8 protein in a regulated way in mammalian cells (Gossen, M., & Bujard, H. 1992, *Proc. Natl. Acad. Sci. USA* 89: 5547–5551). For the polyadenylation of the mRNA other signals, from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes Bam HI and Asp 718 and then dephosphorylated using calf intestinal phosphatase by procedures known in the art. The vector is then isolated from a 1% agarose gel.

The DNA sequence encoding the complete TR11 protein including its leader sequence is amplified using PCR oligonucleotide primers corresponding to the 5' and 3' sequences of the gene having, for instance, the same sequences as the 5' and 3' primers used for cloning in baculovirus pA vectors as shown in Example 2, above.

The amplified fragment is digested with the endonucleases Bam HI and Asp 718 and then purified again on a 1% agarose gel. The isolated fragment and the dephosphorylated vector are then ligated with T4 DNA ligase. *E. coli* HB 101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. 5 μg of the expression plasmid pC4 is cotransfected with 0.5 μg of the plasmid pSV2-neo using lipofectin (Felgner et al., supra). The plasmid pSV2neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsynized and seeded in hybridoma cloning plates (Gronier, Germany) in alpha minus MEM supplemented with 10, 25, or 50 ng/ml of methotrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100–200 μM. Expression of the desired gene product is analyzed, for instance, by SDS-PAGE and Western blot or by reverse phase HPLC analysis.

The skilled artisan appreciates that a similar approach could easily be designed and utilized to generate pcDNAIII- and pC4-based bacterial expression constructs for the expression of TR11SV1 and TR11SV2 in mammalian cells. This would be done by designing PCR primers containing similar restriction endonuclease recognition sequences combined with gene-specific sequences for TR11SV1 and TR11SV2 and proceeding as described above.

Example 4

Tissue Distribution of TR11, TR11SV1, and TR11SV2 mRNA Expression

Northern blot analysis is carried out to examine TR11, TR11SV1, and TR11SV2 gene expression in human tissues, using methods described by, among others, Sambrook et al., cited above. cDNA probes containing the entire nucleotide sequences of the TR11, TR11SV1, and TR11SV2 proteins (SEQ ID) NO:1, SEQ ID NO:3, and SEQ ID NO:5, respectively) are labeled with $^{32}$P using the rediprime DNA After labeling, the probe is purified using a CHROMA SPIN-100 column (Clontech Laboratories, Inc.), according to manufacturer's protocol number PT1200-1. The purified labeled probe is then used to examine various human tissues for TR11, TR11SV1, and TR11SV2 mRNA.

Multiple Tissue Northern (MTN) blots containing various human tissues (H) or human immune system tissues (IM) are obtained from Clontech and are examined with the labeled probe using ExpressHyb hybridization solution (Clontech) according to manufacturer's protocol number PT1190-1. Following hybridization and washing, the blots are mounted and exposed to film at −70° C. overnight, and films developed according to standard procedures.

Example 5(a)

Expression and Purification of TR11-Fc(TR11-Ig Fusion Example 5(a): Expression and Purification of TR11-Fc(TR11-Ig Fusion Protein) and Cleaved TR11

The putative transmembrane domain of translated TR11 receptor is determined by hydrophobicity using the method of Goldman et al. (*Ann. Rev. of Biophys. Biophys. Chem.* 15:321–353 (1986)) for identifying nonpolar transbilayer helices. The region upstream of this transmembrane domain, encoding the putative leader peptide and extracellular domain, is selected for the production of an Fc fusion protein. Primers are designed to amplify the corresponding coding region from the deposited clone by PCR with the addition of a BglII site, a Factor Xa protease site, and an Asp 718 site at the 3' end. This is cloned into COSFclink to give the TR11-Fclink plasmid. The PCR product is digested with Eco RI and Asp 718 and ligated into the COSFclink plasmid (Johansen, et al., *J. Biol. Chem.* 270:9459–9471 (1995)) to produce TR11-Fclink.

COS cells are transiently transfected with TR11-Fclink and the resulting supernatant is immunoprecipitated with protein A agarose. Western blot analysis of the immunoprecipitate using goat anti-human Fc antibodies reveals a strong band consistent with the expected size for glycosylated TR11-Fc (greater than 65,940 kD). A 15L transient COS transfection is performed and the resulting supernatant is purified. The purified protein is used to immunize mice following DNA injection for the production of mAbs.

CHO cells are transfected with TR11-Fclink to produce stable cell lines. Five lines are chosen by dot blot analysis for expansion and are adapted to shaker flasks. The line with the highest level of TR11-Fc protein expression is identified by Western blot analysis. TR11-Fc protein purified from the supernatant of this line is used for cell binding studies by flow cytometry, either as intact protein or after factor Xa cleavage and biotinylation.

The skilled artisan appreciates that a similar approach could easily be designed and utilized to generate expression constructs for the expression of TR11SV1 and TR11SV2 as Fc fusion proteins. This would be done by designing PCR primers containing similar restriction endonuclease recognition sequences combined with gene-specific sequences for TR11SV1 and TR11SV2 and proceeding as described above.

Example 5(b)

Purification of TR11-Fc from CHO E1A Conditioned Media Followed by Cleavage and Biotinylation of TR11

Assays

Product purity through the purification is monitored on 15% Laemmli SDS-PAGE gels run under reducing and non-reducing conditions. Protein concentration is monitored by $A_{280}$ assuming extinction coefficients for the receptor and the chimera calculated from the sequences.

Protein G Chromatography of the TR11-Fc Fusion Protein

All steps described below are carried out at 4° C. 15L of CHO conditioned media (CM; 0.2μ filtered following harvest in cell culture) is applied to a 5×10 cm column of Protein G at a linear flow rate of 199 cm/h. The column is previously washed with 100 mM glycine, pH 2.5 and equilibrated in 20 mM sodium phosphate, 150 mM sodium chloride, pH 7 prior to sample application. After the CM is loaded the column is washed with 5 column volumes of 20 mM sodium phosphate, 150 mM sodium chloride, pH 7 and eluted with 100 mM glycine, pH 2.5. The eluate is immediately neutralized with 3 M Tris, pH 8.5 and 0.2 μ filtered.

Concentration/Dialysis

Protein G eluate is concentrated about 10 fold in an Amicon stirred cell fitted with a 30K membrane. The concentrate is dialyzed against buffer.

Factor Xa Cleavage and Purification to Generate Free Receptor

TR11-Fc is added to 50 μg of Factor Xa resulting in a 1:200 e:s ratio. The mixture is incubated overnight at 4° C.

Protein G Chromotography of the Free TR11 Receptor

A 1 ml column of Protein G is equilibrated in 20 mM sodium phosphate, 150 mM sodium chloride, pH 6.5 in a disposable column using gravity flow. The cleaved receptor is passed over the column 3 times after which the column is washed with 20 mM sodium phosphate, 150 mM sodium chloride, pH 6.5 until no $A_{280}$ absorbance is seen. The column is eluted with 2. 5 ml of 100 mM glycine, pH 2. 5 neutralized with 83 μl of 3 M Tris, pH 8.5. TR8 elutes in the nonbound fraction.

Concentration

The nonbound fraction from the Protein G column is concentrated in a Centricon 10K cell (Amicon) to about a final concentration of 3.5 mg/ml estimated by $A_{280}$ extinction coefficient 0.7.

Mono S Chromotography

The concentrated sample is diluted to 5 ml with 20 mM sodium phosphate, pH 6 and applied to a 0.5×5 cm Mono S column equilibrated in 20 mM sodium phosphate, pH 6 at a linear flow rate of 300 cm/h. The column is washed with 20 mM sodium phosphate, pH 6 and eluted with a 20 column volume linear gradient of 20 mM sodium phosphate, pH 6 to 20 mM sodium phosphate, 1 M sodium chloride, pH 6. TR11 protein elutes in the nonbound fraction.

Concentration/Dialysis

The nonbound fraction from the Mono S column is concentrated to 1 ml as above using a Centricon 10K cell and is dialyzed against 20 mM sodium phosphate, 150 mM sodium chloride, pH 7.

Biotinylation 0.5 mg of TR11 at about 1–2 mg/ml is dialyzed against 100 mM borate, pH 8.5. A 20-fold molar excess of NHS-LC Biotin is added and the mixture is left on a rotator overnight at 4° C. The biotinylated TR11 is dialyzed against 20 mM sodium phosphate, 150 mM sodium chloride, pH 7, sterile filtered and stored at −70° C. Biotinylation is demonstrated on a Western blot probed with strepavidin HRP and subsequently developed with ECL reagent.

Example 6

Chromosomal Mapping of TR11, TR11SV1, or TR11SV2

An oligonucleotide primer set is designed according to the sequence at the 5' end of SEQ ID NO:1, SEQ ID NO:3, or SEQ ID NO:5. This primer preferably spans about 100 nucleotides. This primer set is then used in a polymerase chain reaction under the following set of conditions: 30 seconds, 95 degree C.; 1 minute, 56 degree C.; 1 minute, 70 degree C. This cycle is repeated 32 times followed by one 5 minute cycle at 70 degree C. Human, mouse, and hamster DNA is used as template in addition to a (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 7

Construction of N-Terminal and/or C-Terminal Deletion Mutants

The following general approach may be used to clone an N-terminal or C-terminal deletion TR11, TR11SV1 or TR11SV2 deletion mutant. Generally, two oligonucleotide primers of about 15–25 nucleotides are derived from the desired 5' and 3' positions of a polynucleotide of SEQ ID NO:1 (or from SEQ ID NOs:3 and 5, if constructing an N- or C-terminal deletion of TR11SV1 or TR11SV2, respectively). One of skill in the art will recognize that the procedures outlined in this example may also easily be used to generate TR11SV1 and TR11SV2 N- and C-terminal deletions in place of TR11 deletions. The 5' and 3' positions of the primers are determined based on the desired TR11 polynucleotide fragment. An initiation and stop codon are added to the 5' and 3' primers respectively, if necessary, to express the TR11 polypeptide fragment encoded by the polynucleotide fragment. Preferred TR11 polynucleotide fragments are those encoding the N-terminal and C-terminal deletion mutants disclosed above in the "Polynucleotide and Polypeptide Fragments" section of the Specification.

Additional nucleotides containing restriction sites to facilitate cloning of the TR11 polynucleotide fragment in a desired vector may also be added to the 5' and 3' or from the deposited cDNA clone using the appropriate PCR oligonucleotide primers and conditions discussed herein or known in the art. The TR11 polypeptide fragments encoded by the TR11 polynucleotide fragments of the present invention may be expressed and purified in the same general manner as the full length polypeptides, although routine modifications may be necessary due to the differences in chemical and physical properties between a particular fragment and full length polypeptide.

As a means of exemplifying but not limiting the present invention, the polynucleotide encoding the TR11 polypeptide fragment R-59 to P-162 is amplified and cloned as follows: A 5' primer is generated comprising a restriction enzyme site followed by an initiation codon in frame with the polynucleotide sequence encoding the N-terminal portion of the polypeptide fragment beginning with R-59. A complementary 3' primer is generated comprising a restriction enzyme site followed by a stop codon in frame with the polynucleotide sequence encoding C-terminal portion of the TR11 polypeptide fragment ending with P-162.

The amplified polynucleotide fragment and the expression vector are digested with restriction enzymes which recognize the sites in the primers. The digested polynucleotides are then ligated together. The TR11 polynucleotide fragment is inserted into the restricted expression vector, preferably in a manner which places the TR11 polypeptide fragment coding region downstream from the promoter. The ligation mixture is transformed into competent *E. coli* cells using standard procedures and as described in the Examples herein. Plasmid DNA is isolated from resistant colonies and the identity of the cloned DNA confirmed by restriction analysis, PCR and DNA sequencing.

Example 8

Protein Fusions of TR11, TR11SV1 or TR11SV2

TR11, TR11SV1 or TR11SV2 polypeptides are preferably fused to other proteins. These fusion proteins can be used for a variety of applications. For example, fusion of TR11, TR11SV1 or TR11SV2 polypeptides to His-tag, HA-tag, protein A, IgG domains, and maltose binding protein facilitates purification. (See Example 1; see also EP A 394,827; Traunecker, et al., Nature 331:84–86 (1988).) Similarly, fusion to IgG-1, IgG-3, and albumin increases the halflife time in vivo. Nuclear localization signals fused to TR11, TR11SV1 or TR11SV2 polypeptides can target the protein to a specific subcellular localization, while covalent heterodimer or homedimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 1.

Briefly, the human Fc portion of the IgG molecule can be PCR amplified, using primers that span the 5' and 3' ends of the sequence described below. These primers also should have convenient restriction enzyme sites that will facillitate cloning into an expression vector, preferably a mammalian expression vector.

For example, if pC4 (Accession No. 209646) is used, the human Fc portion can be ligated into the Bam HI cloning site. Note that the 3' Bam HI site should be destroyed. Next, the vector containing the human Fc portion is restricted with Bam HI, linearizing the vector, and TR11, TR11SV1 or TR11SV2 polynucleotide is ligated into this Bam HI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occuring signal sequence is not used, the vector can be modified to include a heterologous signal sequence. (See, e.g., WO 96/34891.) Human IgG Fc region:

GGGATCCGGAGCCCAAATCTTCTGA-
CAAAACTCACACATGCCCACCGTGCC CAG-
CACCTGAATTCGAGGGTGCACCGT-
CAGTCTTCCTCTTCCCCCCAAAACC
CAAGGACACCCTCATGATCTCCCG-
GACTCCTGAGGTCACATGCGTGGTGGT
GGACGTAAGCCACGAAGACCCTGAGGT-
CAAGTTCAACTGGTACGTGGACG GCGTGGAG-
GTGCATAATGCCAAGACAAAGCCGCGG-
GAGGAGCAGTACAAC
AGCACGTACCGTGTGGTCAGCGTCCT-
CACCGTCCTGCACCAGGACTGGCTG AATG-
GCAAGGAGTACAAGTGCAAGGTCTCCAA-
CAAAGCCCTCCCAACCCCC
ATCGAGAAAACCATCTCCAAAGC-
CAAAGGGCAGCCCCGAGAACCACAGGT GTA-
CACCCTGCCCCCATCCCGGGATGAGCT-
GACCAAGAACCAGGTCAGCCT
GACCTGCCTGGTCAAAGGCTTCTATC-
CAAGCGACATCGCCGTGGAGTGGGA GAG-
CAATGGGCAGCCGGAGAACAACTACAA-
GACCACGCCTCCCGTGCTGG
ACTCCGACGGCTCCTTCTTCCTCTACAG-
CAAGCTCACCGTGGACAAGAGCA GGTG-
GCAGCAGGGGAACGTCTTCTCATGCTC-
CGTGATGCATGAGGCTCTGC
ACAACCACTACACGCAGAAGAGCCTCTC-
CCTGTCTCCGGGTAAATGAGTGC GACGGC-
CGCGACTCTAGAGGAT (SEQ ID NO:18).

Example 9

Production of an Antibody

The antibodies of the present invention can be prepared by a variety of methods. (See, Current Protocols, Chapter 2.) For example, cells expressing TR11, TR11SV1 or TR11SV2 is administered to an animal to induce the production of sera containing polyclonal antibodies. In a preferred method, a preparation of TR11, TR11SV1 or TR11SV2 protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with TR11, TR11SV1 or TR11SV2 polypeptide or, more preferably, with a secreted TR11, TR11SV1 or TR11SV2 polypeptide-expressing cell. Such cells may be cultured in any suitable tissue culture medium; however, it is preferable to culture cells in Earle's modified Eagle's medium supplemented with 10% fetal bovine serum (inactivated at about 56 degree C.), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify cloned which secrete antibodies capable of binding the TR11, TR11SV1 or TR11SV2 polypeptide.

Alternatively, additional antibodies capable of binding to TR11, TR11SV1 or TR11SV2 polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the TR11, TR11SV1 or TR11SV2 protein-specific antibody can be blocked by TR11, TR11SV1 or TR11SV2. Such antibodies comprise anti-idiotypic antibodies to the TR11, TR11SV1 or TR11SV2 protein-specific antibody and can be used to immunize an animal to induce formation of further TR11, TR11SV1 or TR11SV2 protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted TR11, TR11SV1 or TR11SV2 protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., Bio-Techniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Example 10

Production of TR11, TR11SV1 or TR11SV2 Protein for High-Throughput Screening Assays The following protocol produces a supernatant containing the soluble or extracellular portion of TR11, TR11SV1 or TR11SV2 polypeptides, constructed in Examples 1 and 7, to be tested. This supernatant can then be used in the Screening Assays described in the following Examples.

First, dilute Poly-D-Lysine (644 587 Boehringer-Mannheim) stock solution (1 mg/ml in PBS) 1:20 in PBS (w/o calcium or magnesium 17–516F Biowhittaker) for a working solution of 50ug/ml. Add 200 ul of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2 \times 10^5$ cells/well in 0.5ml DMEM(Dulbecco's Modified Eagle Medium)(with 4.5 G/L glucose and L-glutamine (12–604F Biowhittaker))/10% heat inactivated FBS(14–503F Biowhittaker)/1×Penstrep(17–602E Biowhittaker). Let the cells grow overnight.

The next day, mix together in a sterile solution basin: 300 ul Lipofectarrtine (18324-012 Gibco/BRL) and 5ml Optimem I (31985070 Gibco/BRL)/96-well plate. With a small volume multi-channel pipetter, aliquot approximately 2ug of an expression Examples 8–10, into an appropriately labeled 96-well round bottom plate. With a multi-channel pipetter, add 50 ul of the Lipofectamine/Optimem I mixture to each well. Pipette up and down gently to mix. Incubate at RT 15–45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using a 12-channel pipetter with tips on every other channel, adds the 200 ul of DNA/Lipofectamine/Optimem I complex to the odd wells first, then to the even wells, to each row on the 24-well plates. Incubate at 37 degree C. for 6 hours.

While cells are incubating, prepare appropriate media, either 1%BSA in DMEM with 1×penstrep, or HGS CHO-5 media (116.6 mg/L of CaCl2 (anhyd); 0.00130 mg/L $CuSO_4$-$5H_2O$; 0.050 mg/L of $Fe(NO_3)_3$-$9H_2O$; 0.417 mg/L of $FeSO_4$-$7H_2O$; 311.80 mg/L of Kcl; 28.64 mg/L of $MgCl_2$; 48.84 mg/L of $MgSO_4$; 6995.50 mg/L of NaCl; 2400.0 mg/L of $NaHCO_3$; 62.50 mg/L of $NaH_2PO_4$-$H_2O$; 71.02 mg/L of $Na_2HPO_4$; 0.4320 mg/L of $ZnSO_4$-$7H_2O$; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmittic Acid; 0.010 mg/L of Pamitic Acid; 100 mg/L of Pluronic F-68; 0.010 mg/L of Stearic Acid; 2.20 mg/L of Tween 80; 4551 mg/L of D-Glucose; 130.85 mg/ml of L-Alanine; 147.50 mg/ml of L-Arginine-HCL; 7.50 mg/ml of L-Asparagine-$H_2O$; 6.65 mg/ml of L-Aspartic Acid; 29.56 mg/ml of L-Cystine-2HCL-$H_2O$; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL-$H_2O$; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-$2H_2O$; and 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; 0.680 mg/L of Vitamin $B_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 2OuM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; 10 mg/L of Methyl-B-Cyclodextrin complexed with Retinal Acetate. Adjust osmolarity to 327 mOsm) with 2 mm glutamine and 1×penstrep. (BSA (81-068-3 Bayer) 100 gm dissolved in 1L DMEM for a 10% BSA stock solution). Filter the media and collect 50 ul for endotoxin assay in 15 ml polystyrene conical.

The transfection reaction is terminated, preferably by tag-teaming, at the end of adds 1.5 ml appropriate media to each well. Incubate at 37 degree C. for 45 or 72 hours depending on the media used: 1%BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in the following Examples.

It is specifically understood that when activity is obtained in any of the assays described below using a supernatant, the activity originates from either the TR11, TR11SV1 or TR11SV2 polypeptide directly (e.g., as a soluble protein) or by TR11, TR11SV1 or TR11SV2 inducing expression of other proteins, which are then secreted into the supernatant. Thus, the invention further provides a method of identifying the protein in the supernatant characterized by an activity in a particular assay.

Example 11

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resulting cells.

The Jaks are activated by a wide range of receptors summarized in the Table below. (Adapted from review by Schidler and Darnell, Ann. Rev. Biochem. 64:621–51 (1995).) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a WSXWS motif (a membrane proxial region encoding Trp-Ser-Xxx-Trp-Ser (SEQ ID NO:5)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

| ISRE Ligand | JAKs | | | | STATS | GAS (elements) or |
|---|---|---|---|---|---|---|
| | tyk2 | Jak1 | Jak2 | Jak3 | | |
| IFN family | | | | | | |
| IFN-a/B | + | + | − | − | 1,2,3 | ISRE |
| IFN-g | | + | + | − | 1 | GAS |
| (IRF1 > Lys6 > IFP) | | | | | | |
| Il-10 | + | ? | ? | − | 1,3 | |
| gp130 family | | | | | | |
| IL-6 (Pleiotrohic) | + | + | + | ? | 1,3 | GAS |
| (IRF1 > Lys6 > IFP) | | | | | | |
| Il-11(Pleiotrohic) | ? | + | ? | ? | 1,3 | |
| OnM(Pleiotrohic) | ? | + | + | ? | 1,3 | |
| LIF(Pleiotrohic) | ? | + | + | ? | 1,3 | |
| CNTF(Pleiotrohic) | −/+ | + | + | ? | 1,3 | |
| G-CSF(Pleiotrohic) | ? | + | ? | ? | 1,3 | |
| IL-12(Pleiotrohic) | + | − | + | + | 1,3 | |
| g-C family | | | | | | |
| IL-2 (lymphocytes) | − | + | − | + | 1,3,5 | GAS |
| IL-4 (lymph/myeloid) >> Ly6)(IgH) | − | + | − | + | 6 | GAS (IRF1 = IFP |
| IL-7 (lymphocytes) | − | + | − | + | 5 | GAS |
| IL-9 (lymphocytes) | − | + | − | + | 5 | GAS |
| IL-13 (lymphocyte) | − | + | ? | ? | 6 | GAS |
| IL-15 | ? | + | ? | + | 5 | GAS |
| gp140 family | | | | | | |
| IL-3 (myeloid) (IRF1 > IFP >> Ly6) | − | − | + | − | 5 | GAS |
| IL-5 (myeloid) | − | − | + | − | 5 | GAS |
| GM-CSF (myeloid) | − | − | + | − | 5 | GAS |
| Growth hormone family | | | | | | |
| GH | ? | − | + | − | 5 | |
| PRL | ? | +/− | + | − | 1,3,5 | |
| EPO | ? | − | + | − | 5 | GAS(B- CAS > IRF1 = IFP >> Ly6) |
| Receptor Tyrosine Kinases | | | | | | |
| EGF | ? | + | + | − | 1,3 | GAS(IRF1) |
| PDGF | ? | + | + | − | 1,3 | |
| CSF-1 | ? | + | + | − | 1,3 | GAS (not IRF1) |

To construct a synthetic GAS containing promoter element, which is used in the Biological Assays described in Examples 14–15, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457–468 (1994).), although other GAS or ISRE elements can be used instead. The 5' primer also contains 18 bp of sequence complementary to the SV40 early promoter sequence and is flanked with an XhoI site. The sequence of the 5' primer is:

5': GCGCCTCGAGATTTCCCCGAAATCTA-GATTTCCCCGAAATGATTTCCCCG AAAT-GATTTCCCCGAAATATCTGCCATCTCAATTAG:3' (SEQ ID NO:19)

The downstream primer is complementary to the SV40 promoter and is flanked with a HindIII site: 5':GCG-GCAAGCTTTTTGCAAAGCCTAGGC:3' (SEQ ID NO:20)

PCR amplification is performed using the SV40 promoter template present in the B-Gal:promoter plasmid obtained from Clontech. The resulting PCR fragment is digested with XhoI/HindIII and subcloned into BLSK2-. (Stratagene.) Sequencing with forward and reverse primers confirms that the insert contains the following sequence:

5':CTCGAGATTTCCCCGAAATCTAGATTTCCCCG AAATGATTTCCCCGAAATG ATTTC-CCCGAAATATCTGCCATCTCAATTAGT-CAGCAACCATAGTCCCGCCC CTAACTCCGC-CCATCCCGCCCCTAACTCCGCCCAGTTCCGCC CATTCTCCGC CCCATGGCTGACTAATTTTTT-TATTTATGCAGAGGCCGAGGCCGCCTCGGC CTCTGAGCTATTCCAGAAGTAGTGAG-GAGGCTTTTTTGGAGGCCTAGGCTTT TGCAAA AAGCTT:3' (SEQ ID NO:21)

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is sub-cloned into the pSEAP-Promoter vector obtained from the Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in the following Examples.

Other constructs can be made using the above description and replacing GAS with a different promoter sequence. For example, construction of reporter molecules containing NFK-B and EGR promoter sequences are described in the following Examples. However, many other promoters can be substituted using the protocols described in these Examples. For instance, SRE, IL-2, NFAT, or Osteocalcin promoters can be substituted, alone or in combination (e.g., GAS/NF-KB/EGR, GAS/NF-KB, Il-2/NFAT, or NF-KB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 12

High-Throughput Screening Assay for T-cell Activity

The following protocol is used to assess T-cell activity of TR11, TR11SV1 or TR11SV2 by determining whether TR11, TR11SV1 or TR11SV2 supernatant proliferates and/or differentiates T-cells. T-cell activity is assessed using the GAS/SEAP/Neo construct produced in previous Examples. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic $CD4^{+\ Th}1$ helper cells. In order to generate stable cell lines, approximately 2 million Jurkat cells are transfected with the GAS-SEAP/neo using DMRIE-C (Life Technologies)(transfection procedure described below). The transfected cells are seeded to a density of approximately 20,000 cells per well and transfectants resistant to 1 mg/ml genticin selected. Resistant colonies are expanded and then tested for their response to increasing concentratons of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI+10% serum with 1%Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15–45 mins.

During the incubation period, count cell concentration, spin down the required number of cells ($10^7$ per transfection), and resuspend in OPTI-MEM to a final concentration of $10^7$ cells/ml. Then add 1 ml of $1 \times 10^7$ cells in OPTI-MEM to T25 flask and incubate at 37 degree C. for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing TR11, TR11SV1 or TR11SV2 polypeptides or TR11, TR11SV1 or TR11SV2 induced polypeptides as produced by the protocol described in the previous Examples.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100,000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using sellophene covers) and stored at −20 degree C. until SEAP assays are performed according to the following Examples. The plates containing the remaining treated cells are placed at 4 degree C. and serve as a source of material for repeating the assay on a specific well if desired.

As a positive control, 100 Unit/ml interferon gamma can be used which is known to activate Jurkat T cells. Over 30 fold induction is typically observed in the positive control wells.

Example 13

High-Throughput Screening Assay Identifying Myeloid Activity

The following protocol is used to assess myeloid activity of TR11, TR11SV1 or TR11SV2 by determining whether TR11, TR11SV1 or TR11SV2 proliferates and/or differentiates myeloid cells. Myeloid cell activity is assessed using the GAS/SEAP/Neo construct produced in the Examples. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 13, a DEAE-Dextran method (Kharbanda et. al., 1994, Cell Growth & Differentiation, 5:259–265) is used. First, harvest $2 \times 10e^7$ U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4.7H_2O$, 1 mM $MgCl_2$, and 675 uM $CaCl_2$. Incubate at 37 degree C. for 45 min.

Wash the cells with RPMI 1640 medium containing 10% FBS and then resuspend in 10 ml complete medium and incubate at 37 degree C. for 36 hr.

The GAS-SEAPlU937 stable cells are obtained by growing the cells in 400 ug/ml G418. The G418-free medium is used for routine growth but every one to two months, the cells should be re-grown in 400 ug/ml G418 for couple of passages.

These cells are tested by harvesting $1 \times 10^8$ cells (this is enough for ten 96-well plates assay) and wash with PBS. Suspend the cells in 200 ml above described growth medium, with a final density of $5 \times 10^5$ cells/ml. Plate 200 ul cells per well in the 96-well plate (or $1 \times 10^5$ cells/well).

Add 50 ul of the supernatant prepared by the protocol described in Example 12. Incubate at 37 degee C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in the Examples.

Example 14

High-Throughput Screening Assay Identifying Neuronal Activity

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed by TR11, TR11SV1 or TR11SV2.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC 12 cells by TR11, TR11SV1 or TR11SV2 can be assessed.

The EGR/SEAP reporter construct can be assembled by the following protocol. The EGR-1 promoter sequence (−633 to +1)(Sakamoto K et al., Oncogene 6:867–871 (1991)) can be PCR amplified from human genomic DNA using the following primers:

5' GCGCTCGAGGGATGACAGCGATAGAACCCCGG -3' (SEQ ID NO:22)

5' GCGAAGCTTCGCGACTCCCCGGATCCGCCTC-3' (SEQ ID NO:23)

Using the GAS:SEAP/Neo vector produced in Example 13, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat. #08-115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. #12449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 12. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5 \times 10^5$ cells/ml.

Add 200 ul of the cell suspension to each well of 96-well plate (equivalent to $1 \times 10^5$ cells/well). Add 50 ul supernatant produced by Example 10, 37 degree C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to the Examples.

Example 15

High-Throughput Screening Assay for T-cell Activity

NF-KB (Nuclear Factor KB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-KB regulates the expression of genes involved in immune cell activation, control of apoptosis (NF-KB appears to shield cells from apoptosis), B and T-cell development, anti-viral and antimicrobial responses, and multiple stress responses.

In non-stimulated conditions, NF-KB is retained in the cytoplasm with I-KB (Inhibitor KB). However, upon stimulation, I-KB is phosphorylated and degraded, causing NF-KB to shuttle to the nucleus, thereby activating transcription of target genes. Target genes activated by NF-KB include IL-2, IL-6, GM-CSF, ICAM-1 and class 1 MHC.

Due to its central role and ability to respond to a range of stimuli, reporter constructs utilizing the NF-KB promoter element are used to screen the supernatants produced in Example 12. Activators or inhibitors of NF-KB would be useful in treating diseases. For example, inhibitors of NF-KB could be used to treat those diseases related to the acute or chronic activation of NF-KB, such as rheumatoid arthritis.

To construct a vector containing the NF-KB promoter element, a PCR based strategy is employed. The upstream primer contains four tandem copies of the NF-KB binding site (GGGGACTTTCCC) (SEQ ID NO:24), 18 bp of sequence complementary to the 5' end of the SV40 early promoter sequence, and is flanked with an XhoI site:

5': G C G G C C T C G A G G G G A C T T T C C C G G G-GACTTTCCGGGGACTTTCCGGGAC TTTCCATC-CTGCCATCTCAATTAG:3' (SEQ ID NO:25)

The downstream primer is complementary to the 3' end of the SV40 promoter and is flanked with a HindIII site:

5':GCGGCAAGCTTTTTGCAAAGCCTAGGC:3' (SEQ ID NO:26)

PCR amplification is performed using the SV40 promoter template present in the pB-gal:promoter plasmid obtained from Clontech. The resulting PCR fragment is digested with XhoI and HindIII and subcloned into BLSK2-. (Stratagene) Sequencing with the T7 and T3 primers confirms the insert contains the following sequence:

5':CTCGAGGGGACTTTCCCGGGGACTTTC-CGGGGACTTTCCGGGACTTTCC ATCTGC-CATCTCAATTAGTCAGCAACCATAGTC-CCGCCCCTAACTCCGCCCA TCCCGCCCCTAACTCCGCCCAGTTCCGC-CCATTCTCCGCCCCATGGCTGACT AATTTTTT-TATTTATGCAGAGGCCGAGGCCGCCTCG-GCCTCTGAGCTATTC CAGAAGTAGTGAGGAGGCTTTTTTGGAG-GCCTAGGCTTTTGCAAAAAGCTT: 3' (SEQ ID NO:27)

Next, replace the SV40 minimal promoter element present in the pSEAP2-promoter plasmid (Clontech) with this NF-KB/SV40 fragment using XhoI and HindIII. However, this vector does not contain a neomycin resistance gene, and therefore, is not preferred for mammalian expression systems.

In order to generate stable mammalian cell lines, the NF-KB/SV40/SEAP cassette is removed from the above NF-KB/SEAP vector using restriction enzymes SalI and NotI, and inserted into a vector containing neomycin resistance. Particularly, the NF-KB/SV40/SEAP cassette was inserted into pGFP-1 (Clontech), replacing the GFP gene, after restricting pGFP-1 with SalI and NotI.

Once NF-KB/SV40/SEAP/Neo vector is created, stable Jurkat T-cells are created and maintained according to the protocol described in the Examples. Similarly, the method for assaying supernatants with these stable Jurkat T-cells is also described in the Examples. As a positive control, exogenous TNF alpha (0.1, 1, 10 ng) is added to wells H9, H10, and H11, with a 5–10 fold activation typically observed.

Example 16

Assay for SEAP Activity

As a reporter molecule for the assays described in the Examples, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5×Dilution Buffer and dispense 15 ul of 2.5×dilution buffer into Optiplates containing 35 ul of a supernatant. Seal the plates with a plastic sealer and incubate at 65 degree C. for 30 min. Separate the Optiplates to avoid uneven heating.

Cool the samples to room temperature for 15 minutes. Empty the dispenser and prime with the Assay Buffer. Add 50 ml Assay Buffer and incubate at room temperature 5 min. Empty the dispenser and prime with the Reaction Buffer (see the table below). Add 50 ul Reaction Buffer and incubate at room temperature for 20 minutes. Since the intensity of the chemiluminescent signal is time dependant, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

| Reaction Buffer Formulation: | | |
|---|---|---|
| # of plates | Rxn buffer diluent (ml) | CSPD (ml) |
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |

-continued

Reaction Buffer Formulation:

| # of plates | Rxn buffer diluent (ml) | CSPD (ml) |
| --- | --- | --- |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 17

High-Throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-3, used here.

For adherent cells, seed the cells at 10,000–20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-3 is made in 10% pluronic acid DMSO. To load the cells with fluo-3, 50 ul of 12 ug/ml fluo-3 is added to each well. The plate is incubated at 37 degree C. in a $CO_2$ incubator for 60 min. The plate is washed four times in the Biotek washer with HBSS leaving 100 ul of buffer.

For non-adherent cells, the cells are spun down from the culture media. Cells are re-suspended to $2-5 \times 10^6$ cells/ml with HBSS in a 50-ml conical tube. 4 ul of 1 mg/ml fluo-3 solution in 10% pluronic acid DMSO is added to each ml of cell suspension. The tube is then placed in a 37 degree C. water bath for 30–60 min. The cells are washed twice with HBSS, resuspended to $1 \times 10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-3. The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3) Camera F/stop is F/2; (4) Excitation is 488 nm; (5) Emission is 530 nm; and (6) Sample addition is 50 ul. Increased emission at 530 nm indicates an extracellular signaling event caused by the a molecule, either TR11, TR11SV1, or TR11SV2 or a molecule induced by TR11, TR11SV1, or TR11SV2, which has resulted in an increase in the intracellular $Ca^{++}$ concentration.

Example 18

High-Throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of, known factors capable of stimulating tyrosine kinase activity, identifying whether TR11, TR11SV1 or TR11SV2 or a molecule induced by TR11, TR11SV1 or TR11SV2 is capable of activating tyrosine kinase signal transduction pathways is of interest. Therefore, the following protocol is designed to identify such molecules capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 4 degree C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5–20 minutes treatment with EGF (60 ng/ml) or 50 ul of the supernatant produced in Example 10, the medium was removed and 100 ml of extraction buffer ((20 mM HEPES pH 7.5, 0.15 M NaCl, 1% Triton X-100, 0.1% SDS, 2 mM Na3VO4, 2 mM Na4P2O7 and a cocktail of protease inhibitors (#1836170) obtained from Boeheringer Mannheim (Indianapolis, Ind.) is added to each well and the plate is shaken on a rotating shaker for 5 minutes at 4° C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4 degree C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/Mg$_{2+}$ (5 mM ATP/50 mM MgCl$_2$), then 10 ul of 5×Assay Buffer (40 mM imidazole hydrochloride, pH7.3, 40 mM beta-glycerophosphate, 1 mM EGTA, 100 mM MgCl$_2$, 5 mM MnCl$_2$, 0.5 mg/ml BSA), then 5 ul of Sodium Vanadate (1 mM), and then 5 ul of water. Mix the components gently and preincubate the reaction mix at 30 degree C. for 2 min. Initial the reaction by adding 10 ul of the control enzyme of the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37 degree C. for 20 min. This allows the streptavadin coated 96 well plate to associate with the biotinylated peptide. Wash the MTP module with 300 ul/well of PBS four times. Next add 75 ul of anti-phophotyrosine antibody conjugated to horse radish peroxidase (anti-P-Tyr-POD (0.5 u/ml)) to each well and incubate at 37 degree C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 19

High-Throughput Screening Assay Identifying Phosphorylation Activity

As a potential alternative and/or compliment to the assay of protein tyrosine kinase activity described in the Examples, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4 degree C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 12 for 5–20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallace DELFIA instrument (time resolved fluorescence). An increased fluorescent signal over background indicates a phosphorylation by TR11, TR11SV1, or TR11SV2 or a molecule induced by TR11, TR11SV1, or TR11SV2.

Example 20

Method of Determining Alterations in the TR11, TR11SV1, or TR11SV2 Gene

RNA isolated from entire families or individual patients presenting with a phenotype of interest (such as a disease) is to be isolated. cDNA is then generated from these RNA samples using protocols known in the art. (See, Sambrook.) The cDNA is then used as a template for PCR, employing primers surrounding regions of interest in SEQ ID NO:1, SEQ ID NO:3, or SEQ ID NO:5. Suggested PCR conditions consist of 35 cycles at 95 degree C. for 30 seconds; 60–120 seconds at 52–58 degree C.; and 60–120 seconds at 70 degree C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons of TR11, TR11SV1 or TR11SV2 is also determined and genomic PCR products analyzed to confirm the results. PCR products harboring suspected mutations in TR11, TR11SV1 or TR11SV2 is then cloned and sequenced to validate the results of the direct sequencing.

PCR products of TR11, TR11SV1 or TR11SV2 are cloned into T-tailed vectors as described in Holton, T. A. and Graham, M. W., Nucleic Acids Research, 19:1156 (1991) and sequenced with T7 polymerase (United States Biochemical). Affected individuals are identified by mutations in TR11, TR11SV1, or TR11SV2 not present in unaffected individuals.

Genomic rearrangements are also observed as a method of determining alterations in the TR11 gene. Genomic clones isolated according to Example 2 are nick-translated with digoxigenindeoxy-uridine 5'-triphosphate (Boehringer Manheim), and FISH performed as described in Johnson, Cg. et al., Methods Cell Biol. 35:73–99 (1991). Hybridization with the labeled probe is carried out using a vast excess of human cot-1 DNA for specific hybridization to the TR11 genomis locus.

Chromosomes are counterstained with 4, 6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region of TR11, TR11SV1 or TR11SV2 (hybridized by the probe) are identified as insertions, deletions, and translocations. These TR11, TR11SV1, or TR11SV2 alterations are used as a diagnostic marker for an associated disease.

Example 21

Method of Detecting Abnormal Levels of TR11, TR11SV1, or TR11SV2 in a Biological Sample TR11, TR11SV1 or TR11SV2 polypeptides can be detected in a biological sample, and if an increased or decreased level of TR11, TR11SV1 or TR11SV2 is detected, this polypeptide is a marker for a particular phenotype. Methods of detection are numerous, and thus, it is understood that one skilled in the art can modify the following assay to fit their particular needs.

For example, antibody-sandwich ELISAs are used to detect TR11, TR11SV1 or TR11SV2 in a sample, preferably a biological sample. Wells of a microtiter plate are coated with specific antibodies to TR11, TR11SV1 or TR11SV2, at a final concentration of 0.2 to 10 ug/ml. The antibodies are either monoclonal or polyclonal and are produced by the method described in the Examples. The wells are blocked so that non-specific binding of TR11, TR11SV1 or TR11SV2 to the well is reduced.

The coated wells are then incubated for >2 hours at RT with a sample containing TR11, TR11SV1 or TR11SV2. Preferably, serial dilutions of the sample should be used to validate results. The plates are then washed three times with deionized or distilled water to remove unbounded TR11, TR11SV1 or TR11SV2.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot TR11, TR11SV1 or TR11SV2 polypeptide concentration on the X-axis (log scale) and fluorescence or absorbance of the Y-axis (linear scale). Interpolate the concentration of the TR11, TR11SV1 or TR11SV2 in the sample using the standard curve.

Example 22

Formulating a Polypeptide

The TR11, TR11SV1 or TR11SV2 composition will be formulated and dosed in a fashion consistent with good medical practice, taking into account the clinical condition of the individual patient (especially the side effects of treatment with the TR11, TR11SV1 or TR11SV2 polypeptide alone), the site of delivery, the method of administration, the scheduling of administration, and other factors known to practitioners. The "effective amount" for purposes herein is thus determined by such considerations.

As a general proposition, the total pharmaceutically effective amount of TR11, TR11SV1 or TR11SV2 administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, TR11, TR11SV1 or TR11SV2 is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing TR11, TR11SV1 or TR11SV2 are administered orally, rectally, parenterally, intracistemally, intravaginally, intraperitoneally, topically (as powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

TR11, TR11SV1 or TR11SV2 is also suitably administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman, U et al., Biopolymers 22:547–556 (1983)), poly (2-hydroxyethyl methacrylate) (R. Langer et al., J. Biomed. Mater. Res. 15:167–277 (1981), and R. Langer, Chem. Tech. 12:98–105 (1982)), ethylene vinyl acetate (R. Langer et al.) or poly-D-(-)-3-hydroxybutyric acid (EP 133,988). Sustained-release compositions also include liposomally entrapped TR11, TR11SV1 or TR11SV2 polypeptides. Liposomes containing the TR11, TR11SV1 or TR11SV2 are prepared by methods known per se: DE 3,218,121; Epstein et al., Proc. Natl. Acad. Sci. USA 82:3688–3692 (1985); Hwang et al., Proc. Natl. Acad. Sci. USA 77:4030–4034

(1980); EP 52,322; EP 36,676; EP 88,046; EP 143,949; EP 142, 641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, TR11, TR11SV1 or TR11SV2 is formulated generally by mixing it at the desired degree of purity, in a unit dosage in injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting TR11, TR11SV1 or TR11SV2 uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

TR11, TR11SV1 or TR11SV2 is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

TR11, TR11SV1 or TR11SV2 used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper piercable by a hypodermic injection needle.

TR11, TR11SV1 or TR11SV2 polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous TR11, TR11SV1 or TR11SV2 polypeptide solution, and the resulting mixture is lyophilized. The infusion solution is prepared by reconstituting the lyophilized TR11, TR11SV1 or TR11SV2 polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, TR11, TR11SV1 or TR11SV2 may be employed in conjunction with other therapeutic compounds.

Example 23

Method of Treating Decreased Levels of TR11, TR11SV1 or TR11SV2

The present invention relates to a method for treating an individual in need of a decreased level of TR11, TR11SV1 or TR11SV2 activity in the body comprising, administering to such an individual a composition comprising a therapeutically effective amount of TR11, TR11SV1 or TR11SV2 antagonist. Preferred antagonists for use in the present invention are TR11, TR11SV1 or TR11SV2-specific antibodies.

Moreover, it will be appreciated that conditions caused by a decrease in the standard or normal expression level of TR11, TR11SV1 or TR11SV2 in an individual can be treated by administering TR11, TR11SV1 or TR11SV2, preferably in the secreted form. Thus, the invention also provides a method of treatment of an individual in need of an increased level of TR11, TR11SV1 or TR11SV2 polypeptide comprising administering to such an individual a pharmaceutical composition comprising an amount of TR11, TR11SV1 or TR11SV2 to increase the activity level of TR11, TR11SV1 or TR11SV2 in such an individual.

For example, a patient with decreased levels of TR11, TR11SV1 or TR11SV2 polypeptide receives a daily dose 0.1–100 ug/kg of the polypeptide for six consecutive days. Preferably, the polypeptide is in the secreted form. The exact details of the dosing scheme, based on administration and formulation, are provided in Example 22.

Example 24

Method of Treating Increased Levels of TR11, TR11SV1 or TR11SV2

The present invention also relates to a method for treating an individual in need of an increased level of TR11, TR11SV1 or TR11SV2 activity in the body comprising administering to such an individual a composition comprising a therapeutically effective amount of TR11, TR11SV1 or TR11SV2 or an agonist thereof.

Antisense technology is used to inhibit production of TR11, TR11SV1 or TR11SV2. This technology is one example of a method of decreasing levels of TR11, TR11SV1 or TR11SV2 polypeptide, preferably a secreted form, due to a variety of etiologies, such as cancer.

For example, a patient diagnosed with abnormally increased levels of TR11, TR11SV1 or TR11SV2 is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 22.

Example 25

Method of Treatment Using Gene Therapy—Ex Vivo

One method of gene therapy transplants fibroblasts, which are capable of expressing TR11, TR11SV1 or TR11SV2 polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, am monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphotase. The linear vector is fractionated on agarose gel and purified, using glass beads.

The cDNA encoding TR11, TR11SV1 or TR11SV2 can be amplified using PCR primers which correspond to the 5' and 3' end sequences respectively as set forth in the Examples. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector contains properly inserted TR11, TR11SV1 or TR11SV2.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the TR11, TR11SV1 or TR11SV2 gene is then added to the media and the packaging cells transduced with the vector. The packaging cells now produce infectious viral particles containing the TR11, TR11SV1 or TR11SV2 gene (the packaging cells are now referred to as producer cells).

Fresh media is added to the transduced producer cells, and subsequently, the media is harvested from a 10 cm plate of confluent producer cells. The spent media, containing the infectious viral particles, is filtered through the a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether TR11, TR11SV1 or TR11SV2 protein is produced.

The engineered fibroblasts are then transplanted onto the host, either alone or after having been grown to confluence on cytodex 3 microcarrier beads.

Example 26

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) TR11, TR11SV1 or TR11SV2 sequences into an animal to increase or decrease the expression of the TR11, TR11SV1 or TR11SV2 polypeptide. The TR11, TR11SV1 or TR11SV2 necessary for the expression of the TR11, TR11SV1 or TR11SV2 polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H. et al. (1997) Cardiovasc. Res. 35(3):470–479, Chao J et al. (1997) Pharmacol. Res. 35(6):517–522, Wolff J. A. (1997) Neuromuscul. Disord. 7(5):314–318, Schwartz B. et al. (1996) Gene Ther. 3(5):405–411, Tsurumi Y. et al. (1996) Circulation 94(12):3281–3290 (incorporated herein by reference).

The TR11, TR11SV1 or TR11SV2 polynucleotide constructs may be delivered by any method that delivers injectable materials to the cells of an animal, such as, injection into the interstitial space of tissues (heart, muscle, skin, lung, liver, intestine and the like). The TR11, TR11SV1 or TR11SV2 polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the TR11, TR11SV1 or TR11SV2 polynucleotides may also be delivered in lipsome formulations (such as those taught in Felgner P. L. et al. (1995) Ann. NY Acad. Sci. 772:126–139 and Abdallah B. et al. (1995) Biol. Cell 85(1):1–7) which can be prepared by methods well known to those skilled in the art.

The TR11, TR11SV1 or TR11SV2 polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for a period of up to six months.

The TR11, TR11SV1 or TR11SV2 polynucleotide construct can be delivered to the intestinal space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked TR11, TR11SV1 or TR11SV2 polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked TR11, TR11SV1 or TR11SV2 polynucleotides constructs can be delivered to arteries during angioplasty by the catheter used in the procedure.

The dose response effects of injected TR11, TR11SV1 or TR11SV2 polynucleotide in muscle in vivo is determined as follows. Suitable TR11, TR11SV1 or TR11SV2 template DNA for production of mRNA coding for TR11, TR11SV1 or TR11SV2 polypeptide is prepared in accordance with a standard recombinant DNA methodology. The template DNA, which may be either circular or linear, is either as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The TR11, TR11SV1 or TR11SV2 template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for TR11, TR11SV1 or TR11SV2 protein expression. A time course for TR11, TR11SV1 or TR11SV2 protein expression may be done in a similar fashion except that quadriceps from different mice are harvested at different times. Persistence of TR11, TR11SV1 or TR11SV2 DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using TR11, TR11SV1 or TR11SV2 naked DNA.

It will be clear that the invention may be practiced otherwise than as particularly described in the foregoing description and examples.

Numerous modifications and variations of the present invention are possible in light of the above teachings and, therefore, are within the the scope of the appended claims.

The entire disclosure of all publications (including patents, patent applications, journal articles, laboratory manuals, books, or other documents) cited herein are hereby incorporated by reference.

Further, the Sequence Listing submitted herewith, and the Sequence Listing and FIG. 4A submitted with U.S. Provisional Application Serial No. 60/063 212, filed on Oct. 21, 1997 (to which the present application claims benefit of the filing date under 35 U.S.C. §119(e)), in both computer and paper forms are each hereby incorporated by reference in their entireties.

What is claimed is:

1. An isolated nucleic acid molecule comprising a polynucleotide sequence selected from the group consisting of:
   (a) a polynucleotide sequence encoding amino acid residues −25 to 209 of SEQ ID NO:2;
   (b) a polynucleotide sequence encoding amino acid residues −24 to 209 of SEQ ID NO:2;
   (c) a polynucleotide sequence encoding amino acid residues 1 to 241 of SEQ ID NO:4;
   (d) a polynucleotide sequence encoding amino acid residues 2 to 241 of SEQ ID NO:4;
   (e) a polynucleotide sequence encoding amino acid residues 1 to 162 of SEQ ID NO:4;
   (f) a polynuclelotide sequence encoding amino acid residues −19 to 221 of SEQ ID NO:6;
   (g) a polynucleotide sequence encoding amino acid residues −18 to 221 of SEQ ID NO:6;
   (h) a polynucleotide sequence encoding amino acid residues 1 to 221 of SEQ ID NO:6; and
   (i) a polynucleotide sequence encoding amino acid residues 1 to 148 of SEQ ID NO:6.

2. An isolated nucleic acid molecule comprising a polynucleotide sequence that is fully complementary to the polynucleotide sequence of claim 1.

3. The isolated nucleic acid molecule of claim 1, wherein said polynucleotide sequence is (a).

4. The isolated nucleic acid molecule of claim 3, comprising nucleotides 118 to 820 of SEQ ID NO:1.

5. The isolated nucleic acid molecule of claim 1, wherein said polynucleotide sequence is (b).

6. The isolated nucleic acid molecule of claim 5, comprising nucleotides 121 to 820 of SEQ ID NO:1.

7. The isolated nucleic acid molecule of claim 1, wherein said polynucleotide sequence is (c).

8. The isolated nucleic acid molecule of claim 7, comprising nucleotides 121 to 843 of SEQ ID NO:3.

9. The isolated nucleic acid molecule of claim 1, wherein said polynucleotide sequence is (d).

10. The isolated nucleic acid molecule of claim 9, comprising nucleotides 124 to 843 of SEQ ID NO:3.

11. The isolated nucleic acid molecule of claim 1, wherein said polynucleotide sequence is (e).

12. The isolated nucleic acid molecule of claim 11, comprising nucleotides 121 to 606 of SEQ ID NO:3.

13. The isolated nucleic acid molecule of claim 1, wherein said polynucleotide sequence is (f).

14. The isolated nucleic acid molecule of claim 13, comprising nucleotides 1 to 720 of SEQ ID NO:5.

15. The isolated nucleic acid molecule of claim 1, wherein said polynucleotide sequence is (g).

16. The isolated nucleic acid molecule of claim 15, comprising nucleotides 4 to 720 of SEQ ID NO:5.

17. The isolated nucleic acid molecule of claim 1, wherein said polynucleotide sequence is (h).

18. The isolated nucleic acid molecule of claim 17, comprising nucleotides 58 to 720 of SEQ ID NO:5.

19. The isolated nucleic acid molecule of claim 1, wherein said polynucleotide sequence is (i).

20. The isolated nucleic acid molecule of claim 19, comprising nucleotides 58 to 504 of SEQ ID NO:5.

21. The isolated nucleic acid molecule of claim 1, wherein said isolated nucleic acid molecule also comprises a heterologous polynucleotide sequence.

22. The isolated nucleic acid molecule of claim 21, wherein the heterologous polynucleotide sequence encodes a heterologous polypeptide.

23. A vector comprising the isolated nucleic acid molecule of claim 1.

24. A isolated host cell comprising the nucleic acid molecule of claim 1 operably associated with a heterologous regulatory sequence.

25. A method of producing a polypeptide comprising:
   (a) culturing the host cell of claim 24 under conditions such that the polypeptide encoded by said polynucleotide sequence is expressed; and
   (b) recovering said polypeptide.

26. An isolated nucleic acid molecule comprising a polynucleotide sequence selected from the group consisting of:
   (a) a polynucleotide sequence encoding the full-length polypeptide encoded by the cDNA contained in ATCC Deposit Number 209341;
   (b) a polynucleotide sequence encoding the full-length polypeptide minus the N-terminal methionine residue encoded by the cDNA contained in ATCC Deposit Number 209341;
   (c) a polynucleotide sequence encoding the full-length polypeptide encoded by the cDNA contained in ATCC Deposit Number 209343;
   (d) a polynucleotide sequence encoding the full-length polypeptide minus the N-terminal methionine residue encoded by the cDNA contained in ATCC Deposit Number 209343;
   (e) a polynucleotide sequence encoding the extracellular domain of the polypeptide encoded by the cDNA contained in ATCC Deposit Number 209343;
   (f) a polynucleotide sequence encoding the full-length polypeptide encoded by the cDNA contained in ATCC Deposit Number 209342;
   (g) a polynucleotide sequence encoding the full-length polypeptide minus the N-terminal methionine residue encoded by the cDNA contained in ATCC Deposit Number 209342;
   (h) a polynucleotide sequence encoding the mature form of the polypeptide encoded by the cDNA contained in ATCC Deposit Number 209342; and
   (i) a polynucleotide sequence encoding the extracellular domain of the polypeptide encoded by the cDNA contained in ATCC Deposit Number 209342.

27. An isolated nucleic acid molecule comprising a polynucleotide sequence that is fully complementary to the polynucleotide sequence of claim 26.

28. The isolated nucleic acid molecule of claim 26, wherein said polynucleotide sequence is (a).

29. The isolated nucleic acid molecule of claim 26, wherein said polynucleotide sequence is (b).

30. The isolated nucleic acid molecule of claim 26, wherein said polynucleotide sequence is (c).

31. The isolated nucleic acid molecule of claim 26, wherein said polynucleotide sequence is (d).

32. The isolated nucleic acid molecule of claim 26, wherein said polynucleotide sequence is (e).

33. The isolated nucleic acid molecule of claim 26, wherein said polynucleotide sequence is (f).

34. The isolated nucleic acid molecule of claim 26, wherein said polynucleotide sequence is (g).

35. The isolated nucleic acid molecule of claim 26, wherein said polynucleotide sequence is (h).

36. The isolated nucleic acid molecule of claim 26, wherein said polynucleotide sequence is (i).

37. The isolated nucleic acid molecule of claim 26, wherein said isolated nucleic acid molecule also comprises a heterologous polynucleotide sequence.

38. The isolated nucleic acid molecule of claim 37, wherein the heterologous polynucleotide sequence encodes a heterologous polypeptide.

39. A vector comprising the isolated nucleic acid molecule of claim 26.

40. A isolated host cell comprising the nucleic acid molecule of claim 26 operably associated with a heterologous regulatory sequence.

41. A method of producing a polypeptide comprising:

culturing the host cell of claim 40 under conditions such that the polypeptide encoded by said polynucleotide sequence is expressed; and (b) recovering said polypeptide.

* * * * *